(12) United States Patent
Kshirsagar et al.

(10) Patent No.: US 7,888,349 B2
(45) Date of Patent: Feb. 15, 2011

(54) PIPERAZINE, [1,4]DIAZEPANE, [1,4]DIAZOCANE, AND [1,5]DIAZOCANE FUSED IMIDAZO RING COMPOUNDS

(75) Inventors: Tushar A. Kshirsagar, Woodbury, MN (US); George W. Griesgraber, Eagan, MN (US); Azim A. Celebi, Clark, NJ (US); Philip D. Heppner, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 260 days.

(21) Appl. No.: 10/596,895

(22) PCT Filed: Dec. 22, 2004

(86) PCT No.: PCT/US2004/043474

§ 371 (c)(1),
(2), (4) Date: Jan. 16, 2007

(87) PCT Pub. No.: WO2005/066172

PCT Pub. Date: Jul. 21, 2005

(65) Prior Publication Data

US 2007/0167476 A1    Jul. 19, 2007

Related U.S. Application Data

(60) Provisional application No. 60/533,024, filed on Dec. 29, 2003.

(51) Int. Cl.
    A61K 31/55       (2006.01)
    C07D 243/14      (2006.01)
    C07D 487/22      (2006.01)
    A01N 43/62       (2006.01)

(52) U.S. Cl. ...................................... 514/219; 540/555

(58) Field of Classification Search ........................ None
    See application file for complete search history.

(56) References Cited

U.S. PATENT DOCUMENTS

| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |

(Continued)

FOREIGN PATENT DOCUMENTS

| EP | 0 394 026 | 10/1990 |
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | 95/02597 A1 | 1/1995 |

(Continued)

OTHER PUBLICATIONS

Regan et al. Virology, 2009, 135-143.*

(Continued)

*Primary Examiner*—Noble Jarrell

(57) ABSTRACT

Piperazine, [1,4]diazepane, [1,4]diazocane, and [1,5]diazocane fused imidazo ring compounds (i.e., imidazoquinolines, tetrahydroimidazoquinolines, imidazonaphthyridines, tetrahydroimidazonaphthyridines, and imidazopyridines), pharmaceutical compositions containing the compounds, intermediates, methods of making, and methods of use of these compounds as immunomodulators, for inducing or inhibiting cytokine biosynthesis in animals and in the treatment of diseases including viral and neoplastic diseases are disclosed.

12 Claims, No Drawings

U.S. PATENT DOCUMENTS

| | | |
|---|---|---|
| 6,677,349 B1 | 1/2004 | Griesgraber |
| 6,683,088 B2 | 1/2004 | Crooks et al. |
| 6,696,465 B2 | 2/2004 | Dellaria et al. |
| 6,706,728 B2 | 3/2004 | Hedenstrom et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,818,650 B2 | 11/2004 | Griesgraber |
| 6,841,678 B2 | 1/2005 | Merli et al. |
| 6,852,861 B2 | 2/2005 | Merli et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2003/0096835 A1 | 5/2003 | Crooks et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0144286 A1 | 7/2003 | Frenkel et al. |
| 2003/0161797 A1 | 8/2003 | Miller et al. |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2005/0054590 A1 | 3/2005 | Averett |
| 2005/0085500 A1 | 4/2005 | Gutman et al. |
| 2005/0165236 A1 | 7/2005 | Colombo et al. |
| 2005/0245562 A1 | 11/2005 | Garcia-Echeverria et al. |
| 2008/0269192 A1* | 10/2008 | Griesgraber et al. ... 514/211.09 |

FOREIGN PATENT DOCUMENTS

| | | |
|---|---|---|
| WO | 96/21663 A1 | 7/1996 |
| WO | WO 99/18105 | 10/1998 |
| WO | WO 02/36592 | 5/2002 |
| WO | 02/46194 A2 | 6/2002 |
| WO | 03/103584 A2 | 12/2003 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO 2006/065280 | 6/2006 |
| WO | WO 2006/074003 | 7/2006 |
| WO | WO 2006/004737 | 8/2006 |
| WO | WO 2006/083400 | 8/2006 |
| WO | WO 2006/083440 | 8/2006 |
| WO | WO 2006/086449 | 8/2006 |
| WO | WO 2006/086633 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO 2006/098862 | 9/2006 |

OTHER PUBLICATIONS

Wozniak et al., "The Amination of 3-nitro-1, 5-naphthyridines by Liquid Ammonia/Potassium Permanganate[1,2], A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.*, 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", (1976). *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation." *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

International Search Report and Written Opinion for PCT/US2004/043474 mailed Jun. 20, 2005.

International Preliminary Report on Patentability for PCT/US2004/043474 mailed Jul. 3, 2006.

Li et al., An improved protocol for the preparation of 3-pyridyl- and some arylboronic acids. J Org Chem. Jul. 26, 2002;67(15):5394-7.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Stillings et al., Substituted 1,3,4-thiadiazoles with anticonvulsant activity. 2. Aminoalkyl derivatives. J Med Chem. Nov. 1986;29(11):2280-4.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

* cited by examiner

PIPERAZINE, [1,4]DIAZEPANE, [1,4]DIAZOCANE, AND [1,5]DIAZOCANE FUSED IMIDAZO RING COMPOUNDS

RELATED APPLICATIONS

This application is the National Stage of International Application No. PCT/US2004/043474, filed Dec. 22, 2004, which claims priority to U.S. Provisional Application Ser. No. 60/533,024, filed Dec. 29, 2003, which is incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction and/or inhibition of cytokine biosynthesis or other mechanisms.

SUMMARY

The present invention provides a new class of compounds that are useful in inducing cytokine biosynthesis in animals. Such compounds are of the following Formula I:

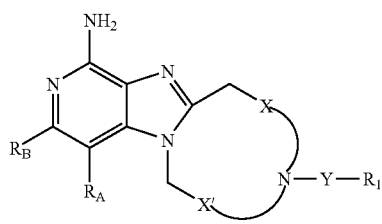

I and, more particularly, compounds are of the following Formula II:

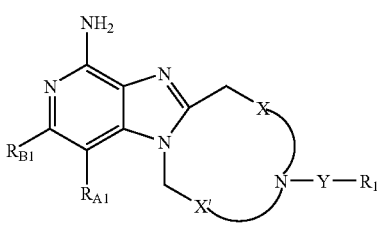

II wherein $R_1$, $R_A$, $R_B$, $R_{A1}$, $R_{B1}$, X, X', and Y are as defined below.

The compounds of Formula I and more particularly Formula II are useful as immune response modifiers (IRMs) due to their ability to induce and/or inhibit cytokine biosynthesis (e.g., induce and/or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human peripheral blood mononuclear cells (PBMC) in a culture with the compound(s) at a concentration range of 30 to 0.014 µM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 µM and analyzing for tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

The invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and Formula II and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through VII:

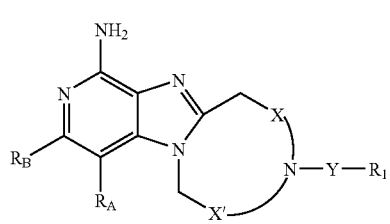

I

-continued

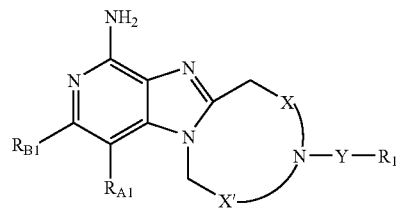

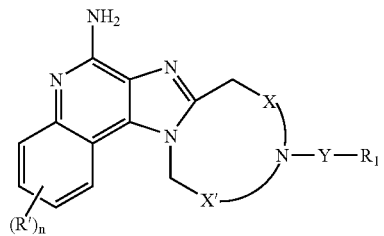

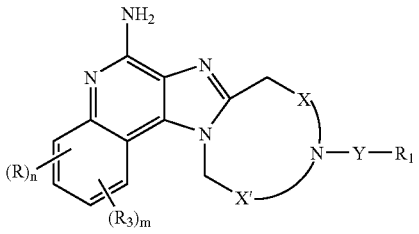

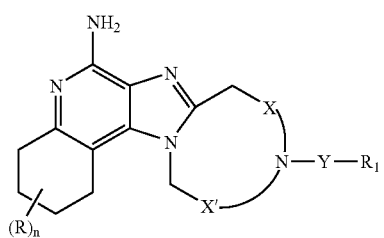

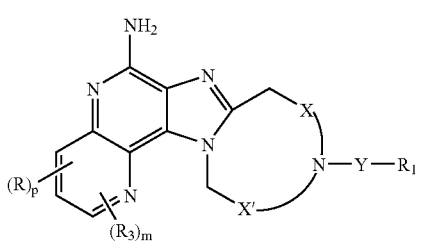

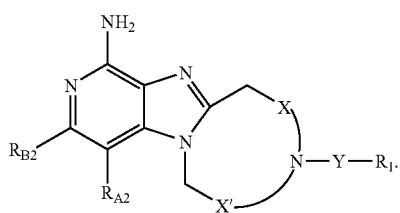

wherein $R_1$, $R_3$, R, R', $R_A$, $R_B$, $R_{A1}$, $R_{B1}$, $R_{A2}$, $R_{B2}$, X, X', Y, m, n, and p are as defined below.

In one embodiment, the present invention provides a compound of Formula I:

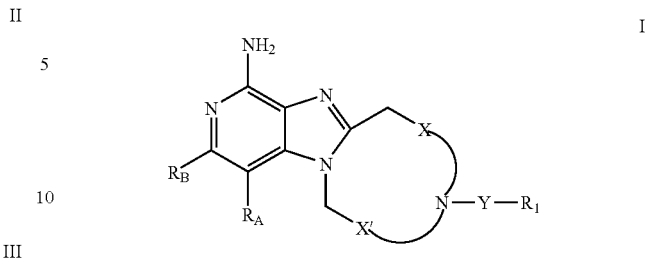

wherein:

$R_A$ and $R_B$ are each independently selected from the group consisting of:
  hydrogen,
  halogen,
  alkyl,
  alkenyl,
  alkoxy,
  alkylthio, and
  —$N(R_9)_2$;

or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R' groups;

or when taken together, $R_A$ and $R_B$ form a fused 5 to 7 membered saturated ring, optionally containing one heteroatom selected from the group consisting of N and S, and unsubstituted or substituted by one or more R groups;

X is a bond or a straight or branched chain $C_{1-2}$ alkylene;

X' is a straight or branched chain $C_{1-8}$ alkylene optionally substituted with hydroxy, —O—$R_{11}$, or one or more halogen atoms wherein the hydroxy, —O—$R_{11}$, or one or more halogen atoms are bonded to a carbon atom other than a carbon atom adjacent to a nitrogen atom;

X and X' are further characterized in that the total number of ring carbon atoms contributed by X and X' is 1 to 3;

Y is selected from the group consisting of:
  a bond,
  —$S(O)_2$—,
  —$S(O)_2$—$N(R_8)$—,
  —$C(R_6)$—,
  —$C(R_6)$—O—,
  —$(R_6)$—$N(R_8)$—,
  —$C(R_6)$—$N(R_8)$—$C(R_6)$—, and
  —$C(R_6)$—$N(R_8)$—$S(O)_2$—;

R is selected from the group consisting of:
  halogen,
  hydroxy,
  alkyl,
  alkenyl,
  haloalkyl,
  alkoxy,
  alkylthio, and
  —$N(R_9)_2$;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy, further with the proviso that when $R_A$ and $R_B$ together form a fused benzene ring that is unsubstituted or substituted by $C_{1-4}$ alkyl, $C_{1-4}$ alkoxy, or halogen, and Y is a bond, $R_1$ is not hydrogen or $C_{1-4}$ alkyl;

$R_6$ is selected from the group consisting of =O and =S;

$R_8$ is selected from the group-consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{11}$ is selected from the group consisting of $C_{1-6}$ alkyl and —Si($C_{1-6}$ alky)$_3$; and R' is a non-interfering substituent;

or a pharmaceutically acceptable salt thereof.

In one embodiment, the present invention provides a compound of Formula II:

wherein:

$R_{A1}$ and $R_{B1}$, are each independently selected from the group consisting of:
hydrogen,
halogen,
alkenyl,
alkoxy,
alkylthio, and
—N($R_9$)$_2$;

or when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;

or when taken together, $R_{A1}$ and $R_{B1}$ form a fused 5 to 7 membered saturated ring, optionally containing one heteroatom selected from the group consisting of N and S, and unsubstituted or substituted by one or more R groups;

X is a bond or a straight or branched chain $C_{1-2}$ alkylene;

X' is a straight or branched chain $C_{1-8}$ alkylene optionally substituted with hydroxy, —O—$R_{11}$, or one or more halogen atoms wherein the hydroxy, —O—$R_{11}$, or one or more halogen atoms are bonded to a carbon atom other than a carbon atom adjacent to a nitrogen atom;

X and X' are further characterized in that the total number of ring carbon atoms contributed by X and X' is 1 to 3;

Y is selected from the group consisting of:
a bond,
—S(O)$_2$—,
—S(O)$_2$—N($R_8$)—,
—C($R_6$)—,
—C($R_6$)—O—,
—C($R_6$)—N($R_8$)—,
—C($R_6$)—N($R_8$)—C($R_6$)—, and
—C($R_6$)—N($R_8$)—S(O)$_2$—;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methyleneoxy; fuirther with the proviso that when $R_{A1}$ and $R_{B1}$ together form a fused benzene ring that is unsubstituted or substituted by $C_{1-4}$ alkyl, $C_{1-4}$ alkoxy, or halogen, and Y is a bond, $R_1$ is not hydrogen or $C_{1-4}$ alkyl;

R is selected from the group consisting of:
halogen,
hydroxy,
alkyl,
alkenyl,
haloalkyl,
alkoxy,
alkylthio, and
—N($R_9$)$_2$;

$R_3$ is selected from the group consisting of:
—Z—$R_4$,
—Z—X"—$R_4$,
—Z—X"—Y'—$R_4$,
—Z—X"—Y'—X"—Y'—$R_4$, and
—Z—X"—$R_5$;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—, -continued

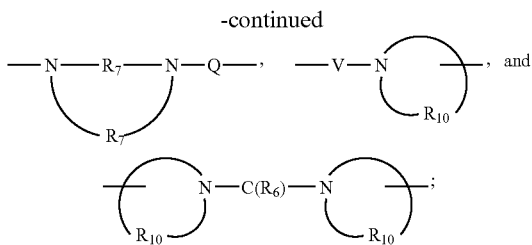

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

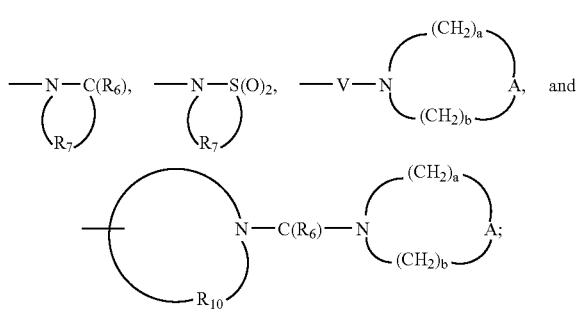

R$_6$ is selected from the group consisting of =O and =S;

R$_7$ is C$_{2-7}$ alkylene;

R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

R$_9$ is selected from the group consisting of hydrogen and alkyl;

R$_{10}$ is C$_{3-8}$ alkylene;

R$_{11}$ is selected from the group consisting of C$_{1-6}$ alkyl and —Si(C$_{1-6}$ alkyl)$_3$;

A is selected from the group consisting of —CH$_2$—, —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In one embodiment, the present invention provides a compound of Formula III:

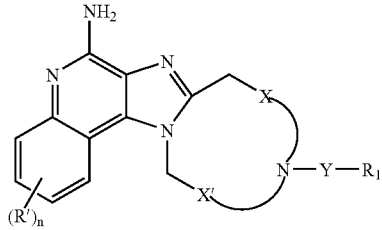

wherein:

X is a bond or a straight or branched chain C$_{1-2}$ alkylene;

X' is a straight or branched chain C$_{1-8}$ alkylene optionally substituted with hydroxy wherein the hydroxy is bonded to a carbon atom other than a carbon atom adjacent a nitrogen atom;

X and X' are further characterized in that the total number of ring carbon atoms contributed by X and X' is 1 to 3;

Y is selected from the group consisting of:

a bond,

—S(O)$_2$—,

—S(O)$_2$—N(R$_8$)—,

—C(R$_6$)—,

—C(R$_6$)—N(R$_8$)—,

—C(R$_6$)—N(R$_8$)—C(R$_6$)—, and

—C(R$_6$)—N(R$_8$)—S(O)$_2$—;

R$_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy; further with the proviso that when Y is a bond, R$_1$ is not hydrogen or C$_{1-4}$ alkyl;

R$_6$ is selected from the group consisting of =O and =S;

R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

R' is a non-interfering substituent; and n is an integer from 0 to 4;

or a pharmaceutically acceptable salt thereof

In one embodiment, the present invention provides a compound of Formula IV:

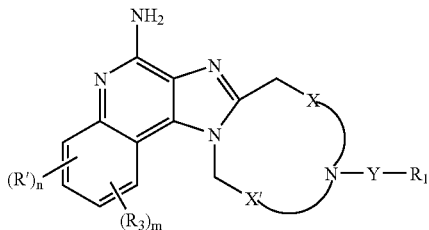

wherein:

X is a bond or a straight or branched chain $C_{1-2}$ alkylene;

X' is a straight or branched chain $C_{1-8}$ alkylene optionally substituted with hydroxy, —O—$R_{11}$, or one or more halogen atoms wherein the hydroxy, —O—$R_{11}$, or one or more halogen atoms are bonded to a carbon atom other than a carbon atom adjacent to a nitrogen atom;

X and X' are further characterized in that the total number of ring carbon atoms contributed by X and X' is 1 to 3;

Y is selected from the group consisting of:
a bond,
—S(O)$_2$—,
—S(O)$_2$—N($R_8$)—,
—C($R_6$)—,
—C($R_6$)—O—,
—C($R_6$)—N($R_8$)—,
—C($R_6$)—N($R_8$)—C($R_6$)—, and
—C($R_6$)—N($R_8$)—S(O)$_2$—;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy;

R is selected from the group consisting of:
halogen,
hydroxy,
alkyl,
alkenyl,
haloalkyl,
alkoxy,
alkylthio, and
—N($R_9$)$_2$;

$R_3$ is selected from the group consisting of:
—Z—$R_4$,
—Z—X"—$R_4$,
—Z—X"—Y'—$R_4$,
—Z—X"—Y'—X"—Y'—$R_4$, and
—Z—X"—$R_5$;

m is 0 or 1; with the proviso that when m is 1, then n is 0 or 1;

n is an integer from 0 to 4;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

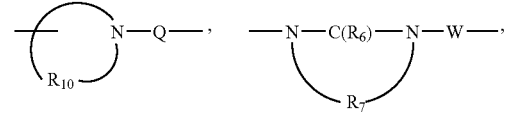

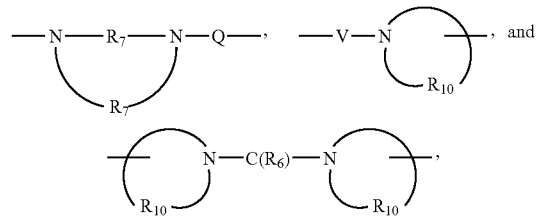

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

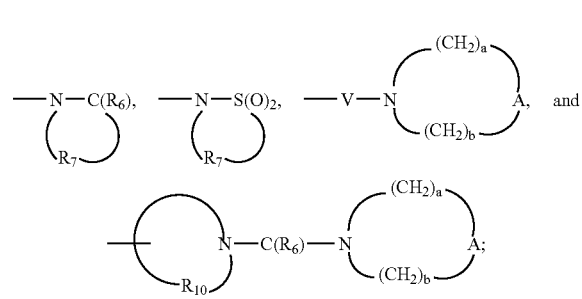

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is selected from the group consisting of $C_{1-6}$ alkyl and —Si($C_{1-6}$ alkyl)$_3$;

A is selected from the group consisting of —CH$_2$—, —O—, —C(O)—, —S(O)$_{0-2}$—, and Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_8$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that $R_1$ is not hydrogen or $C_{1-4}$ alkyl when Y is a bond, and:

n and m are both 0, or m is 0, n is 1, and R is selected from the group consisting of $C_{1-4}$ alkyl, $C_{1-4}$ alkoxy, and halogen;

or a pharmaceutically acceptable salt thereof.

In one embodiment, the present invention provides a compound of Formula IV:

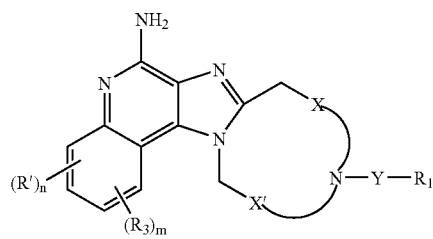

IV wherein:

X is a bond or a straight or branched chain $C_{1-2}$ alkylene;

X' is a straight or branched chain $C_{1-8}$ alkylene optionally substituted with hydroxy wherein the hydroxy is bonded to a carbon atom other than a carbon atom adjacent a nitrogen atom;

X and X' are further characterized in that the total number of ring carbon atoms contributed by X and X' is 1 to 3;

Y is selected from the group consisting of:
a bond,
—S(O)$_2$—,
—S(O)$_2$—N(R$_8$)—,
—C(R$_6$)—,
—C(R$_6$)—N(R$_8$)—,
—C(R$_6$)—N(R$_8$)—C(R$_6$)—, and
—C(R$_6$)—N(R$_8$)—S(O)$_2$—;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy; further with the proviso that when Y is a bond, $R_1$ is not hydrogen or $C_{1-4}$ alkyl;

R is selected from the group consisting of:
halogen,
hydroxy,
alkyl,
alkenyl,
haloalkyl,
alkoxy,
alkylthio, and
—N(R$_9$)$_2$;

$R_3$ is selected from the group consisting of:
—Z—R$_4$,
—Z—X"—R$_4$,
—Z—X"—Y'—R$_4$,
—Z—X"—Y'—X"—Y'—R$_4$, and
—Z—X"—R$_5$;

m is 0 or 1; with the proviso that when m is 1, then n is 0 or 1;

n is an integer from 0 to 4;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

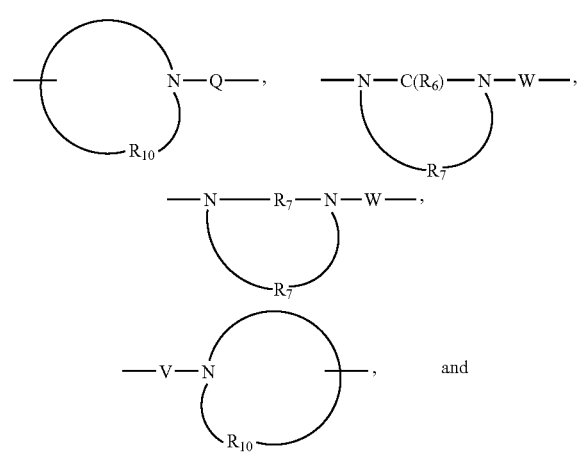

-continued

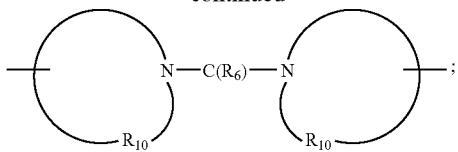

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

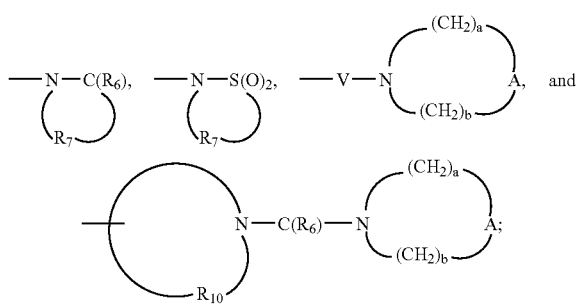

R$_6$ is selected from the group consisting of =O and =S;

R$_7$ is C$_{2-7}$ alkylene;

R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

R$_9$ is selected from the group consisting of hydrogen and alkyl;

R$_{10}$ is C$_{3-8}$ alkylene;

A is selected from the group consisting of —CH$_2$—, —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In one embodiment, the present invention provides a compound of Formula V:

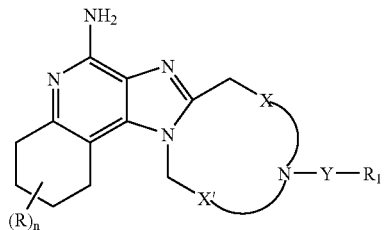

V wherein:

X is a bond or a straight or branched chain C$_{1-2}$ alkylene;

X' is a straight or branched chain C$_{1-8}$ alkylene optionally substituted with hydroxy, —O—R$_{11}$, or one or more halogen atoms wherein the hydroxy, —O—R$_{11}$, or one or more halogen atoms are bonded to a carbon atom other than a carbon atom adjacent to a nitrogen atom;

X and X' are further characterized in that the total number of ring carbon atoms contributed by X and X' is 1 to 3;

Y is selected from the group consisting of:
a bond,
—S(O)$_2$—,
—S(O)$_2$—N(R$_8$)—,
—C(R$_6$)—,
—C(R$_6$)—O—,
—C(R$_6$)—N(R$_8$)—,
—C(R$_6$)—N(R$_8$)—C(R$_6$)—, and
—C(R$_6$)—N(R$_8$)—S(O)$_2$—;

R is selected from the group consisting of:
halogen,
hydroxy,
alkyl,
alkenyl,
haloalkyl,
alkoxy,
alkylthio, and
—N(R$_9$)$_2$;

R$_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy;

R$_6$ is selected from the group consisting of =O and =S;

R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

R$_9$ is selected from the group consisting of hydrogen and alkyl;

R$_{11}$ is selected from the group consisting of C$_{1-6}$ alkyl and —Si(C$_{1-6}$ alkyl)$_3$; and n is an integer from 0 to 4;

or a pharmaceutically acceptable salt thereof.

In one embodiment, the present invention provides a compound of Formula VI:

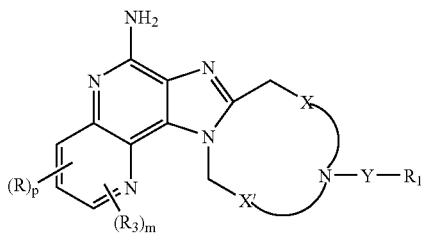

wherein:

X is a bond or a straight or branched chain $C_{1-2}$ alkylene;

X' is a straight or branched chain $C_{1-8}$ alkylene optionally substituted with hydroxy, —O—$R_{11}$, or one or more halogen atoms wherein the hydroxy, —O—$R_{11}$, or one or more halogen atoms are bonded to a carbon atom other than a carbon atom adjacent to a nitrogen atom;

X and X' are further characterized in that the total number of ring carbon atoms contributed by X and X' is 1 to 3;

Y is selected from the group consisting of:
a bond,
—S(O)$_2$—,
—S(O)$_2$—N($R_8$)—,
—C($R_6$)—,
—C($R_6$)—O—,
—C($R_6$)—N($R_8$)—,
—C($R_6$)—N($R_8$)—C($R_6$)—, and
—C($R_6$)—N($R_8$)—S(O)$_2$—;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy;

R is selected from the group consisting of:
halogen,
hydroxy,
alkyl,
alkenyl,
haloalkyl,
alkoxy,
alkylthio, and
—N($R_9$)$_2$;

$R_3$ is selected from the group consisting of:
—Z—$R_4$,
—Z—X"—$R_4$,
—Z—X"—Y'—$R_4$,
—Z—X"—Y'—X"—Y'—$R_4$, and
—Z—X"—$R_5$;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

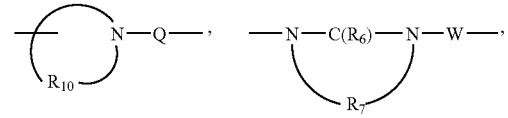

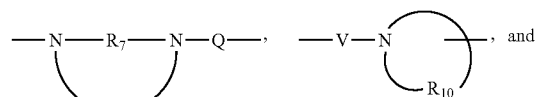

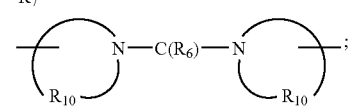

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

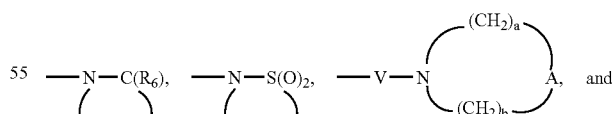

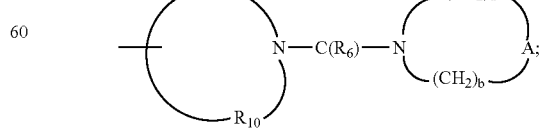

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is selected from the group consisting of $C_{1-6}$ alkyl and —Si($C_{1-6}$ alkyl)$_3$;

A is selected from the group consisting of —CH$_2$—, —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

m is 0 or 1; with the proviso that when m is 1, then p is 0 or 1;

p is an integer from 0 to 3; and a and b are independently integers from 1 to 6 with the proviso that a+b is ≦7;

or a pharmaceutically acceptable salt thereof.

In one embodiment, the present invention provides a compound of Formula VII:

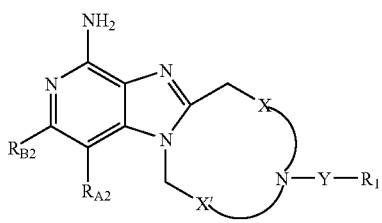

VII wherein:

$R_{A2}$ and $R_{B2}$ are each independently selected from the group consisting of:
hydrogen,
halogen,
alkyl,
alkenyl,
alkoxy,
alkylthio, and
—N(R$_9$)$_2$;

X is a bond or a straight or branched chain $C_{1-2}$ alkylene;

X' is a straight or branched chain $C_{1-8}$ alkylene optionally substituted with hydroxy, —O—R$_{11}$, or one or more halogen atoms wherein the hydroxy, —O—R$_{11}$, or one or more halogen atoms are bonded to a carbon atom other than a carbon atom adjacent to a nitrogen atom;

X and X' are further characterized in that the total number of ring carbon atoms contributed by X and X' is 1 to 3;

Y is selected from the group consisting of:
a bond,
—S(O)$_2$—,
—S(O)$_2$—N(R$_8$)—,
—C(R$_6$)—,
—C(R$_6$)—O—,
—C(R$_6$)—N(R$_8$)—,
—C(R$_6$)—N(R$_8$)—C(R$_6$)—, and
—C(R$_6$)—N(R$_8$)—S(O)$_2$—;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy;

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl; and $R_{11}$ is selected from the group consisting of $C_{1-6}$ alkyl and —Si($C_{1-6}$ alkyl)$_3$;

or a pharmaceutically acceptable salt thereof.

In one embodiment, the present invention provides 9-(methylsulfonyl)-9,10,11,12-tetrahydro-8H-[1,4]diazepino[1',2':1,2]imidazo[4,5-c]quinolin-6-amine or a pharmaceutically acceptable salt thereof.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

Herein, "non-interfering" means that the ability of the compound or salt, which includes a non-interfering substituent, to modulate the biosynthesis of one or more cytokines is not destroyed by the non-interfering substitutent. For certain embodiments, R' is a non-interfering substituent. Illustrative R' groups include those described herein for R and $R_3$.

When a group (or substituent or variable) is present more than once in any Formula described herein, each group (or substituent or variable) is independently selected, whether explicitly stated or not. For example, for the formula —$N(R_9)_2$ each $R_9$ group is independently selected. In another example, when a Y and a Y' group both contain an $R_8$ group, each $R_8$ group is independently selected. In a further example, when more than one Y' group is present (i.e., —Z—X'—Y'—X'—Y'—$R_4$) and each Y' group contains one or more $R_6$ groups, then each Y' group is independently selected, and each $R_6$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., $R_1$, $R_3$, R, R', $R_A$, $R_B$, $R_{A1}$, $R_{B1}$, $R_{A2}$, $R_{B2}$, A, V, X, X', Y, m, n, and p and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments, compounds of Formulas I-VII induce the biosynthesis of one or more cytokines.

In some embodiments, compounds of Formulas I-VU inhibit the biosynthesis of one or more cytokines (e.g., TNF-α).

In certain embodiments, compounds of Formulas I-VII induce the biosynthesis of one or more cytokines and inhibit the biosynthesis of one or more cytokines (e.g., TNF-α).

For certain embodiments, $R_A$ and $R_B$ are each independently selected from the group consisting of hydrogen, halogen, alkyl, alkenyl, alkoxy, alkylthio, and —$N(R_9)_2$; or when taken together, $R_A$ and $R_B$ form a fused aryl ring or heteroaryl ring containing one heteroatom: selected from the group consisting of N and S, wherein the aryl or heteroaryl ring is unsubstituted or substituted by one or more R' groups; or when taken together, $R_A$ and $R_B$ form a fused 5 to 7 membered saturated ring, optionally containing one heteroatom selected from the group consisting of N and S, and unsubstituted or substituted by one or more R groups.

For certain embodiments, $R_A$ and $R_B$ are each independently selected from the group consisting of: hydrogen, halogen, alkyl, alkenyl, alkoxy, alkylthio, and —$N(R_9)_2$.

For certain embodiments, when taken together, $R_A$ and $R_B$ form a fused aryl ring or heteroaryl ring containing one heteroatom selected from the group consisting of N and S, wherein the aryl or heteroaryl ring is unsubstituted or substituted by one or more R' groups.

For certain embodiments, when taken together, $R_A$ and $R_B$ form a fused 5 to 7 membered saturated ring, optionally containing one heteroatom selected from the group consisting of N and S, and unsubstituted or substituted by one or more R groups.

For certain embodiments, $R_{A1}$ and $R_{B1}$ are each independently selected from the group consisting of hydrogen, halogen, alkyl, alkenyl, alkoxy, alkylthio, and —$N(R_9)_2$; or when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group; or when taken together, $R_{A1}$ and $R_{B1}$ form a fused 5 to 7 membered saturated ring, optionally containing one heteroatom selected from the group consisting of N and S, and unsubstituted or substituted by one or more R groups.

For certain embodiments, $R_{A1}$ and $R_{B1}$ are each independently selected from the group consisting of hydrogen, halogen, alkyl, alkenyl, alkoxy, alkylthio, and —$N(R_9)_2$.

For certain embodiments, when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group.

For certain embodiments, when taken together, $R_{A1}$ and $R_{B1}$ form a fused 5 to 7 membered saturated ring, optionally containing one heteroatom selected from the group consisting of N and S, and unsubstituted or substituted by one or more R groups.

In some embodiments of Formula II, $R_{A1}$ and $R_{B1}$ form a fused benzene ring which is unsubstituted.

In some embodiments of Formula II, $R_{A1}$ and $R_{B1}$ form a fused pyridine ring which is unsubstituted.

In some embodiments of Formula II, $R_{A1}$ and $R_{B1}$ form a fused 5 to 7 membered saturated ring, optionally containing one heteroatom selected from the group consisting of N and S, wherein the ring is unsubstituted.

For certain embodiments, $R_{A2}$ is selected from the group consisting of: hydrogen, halogen, alkyl, alkenyl, alkoxy, alkylthio, and —$N(R_9)_2$.

For certain embodiments, $R_{B2}$ is selected from the group consisting of: hydrogen, halogen, alkyl, alkenyl, alkoxy, alkylthio, and —N($R_9$)$_2$.

For certain embodiments, $R_{A2}$ and $R_{B2}$ are each methyl.

For certain embodiments, X is a bond or a straight or branched chain $C_{1-2}$ alkylene. For certain embodiments, X is a bond.

For certain embodiments, X' is a straight or branched chain $C_{1-8}$ alkylene optionally substituted with hydroxy, —O—$R_{11}$, or one or more halogen atoms wherein the hydroxy, —O—$R_{11}$, or one or more halogen atoms are bonded to a carbon atom other than a carbon atom adjacent to a nitrogen atom. For certain embodiments, particularly embodiments of Formulas III and IV, X' is a straight or branched chain $C_{1-8}$ alkylene optionally substituted with hydroxy wherein the hydroxy is bonded to a carbon atom other than a carbon atom adjacent a nitrogen atom. For certain embodiments, X' is methylene. For certain embodiments, X' is ethylene. For certain embodiments, X' is —CF$_2$—CH$_2$—.

For certain embodiments, X and X' are further characterized in that the total number of ring carbon atoms contributed by X and X' is 1 to 3. For certain embodiments, the total number of ring carbon atoms contributed by X and X' is 1. For certain embodiments, the total number of ring carbon atoms contributed by X and X' is 2. For certain embodiments, X' contributes one ring carbon atom. For certain embodiments, X' contributes two ring carbon atoms.

For certain embodiments, X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups. For certain embodiments, X" is propylene. For certain embodiments, X" is methylene.

For certain embodiments, Y is selected from the group consisting of a bond, —S(O)$_2$—, —S(O)$_2$—N($R_8$)—, —C($R_6$)—, —C($R_6$)—O—, —C($R_6$)—N($R_8$)—, —C($R_6$)—N($R_8$)—C($R_6$)—, —C($R_6$)—N($R_8$)—S(O)$_2$—. For certain embodiments, particularly embodiments of Formulas III and IV, Y is selected from the group consisting of a bond, —S(O)$_2$—, —S(O)$_2$—N($R_8$)—, —C($R_6$)—, —C($R_6$)—N($R_8$)—, —C($R_6$)—N($R_8$)—C($R_6$)—, and —C($R_6$)—N($R_8$)—S(O)$_2$—. For certain embodiments, Y is selected from the group consisting of —C(O)—, —S(O)$_2$—, or —(O)—NH—. For certain embodiments, Y is —S(O)$_2$—.

For certain embodiments, Y' is selected from the group consisting of —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(OR$_9$)—,

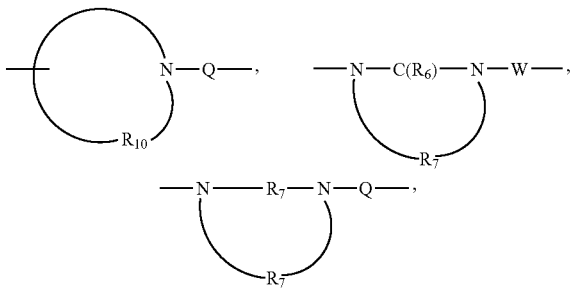

For certain embodiments, Y' is selected from the group consisting of —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(OR$_9$)—,

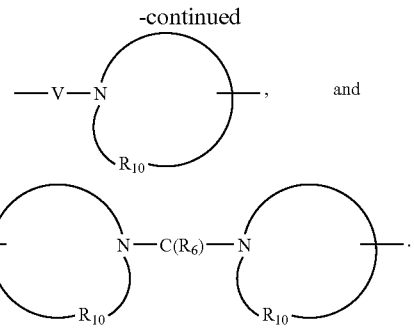

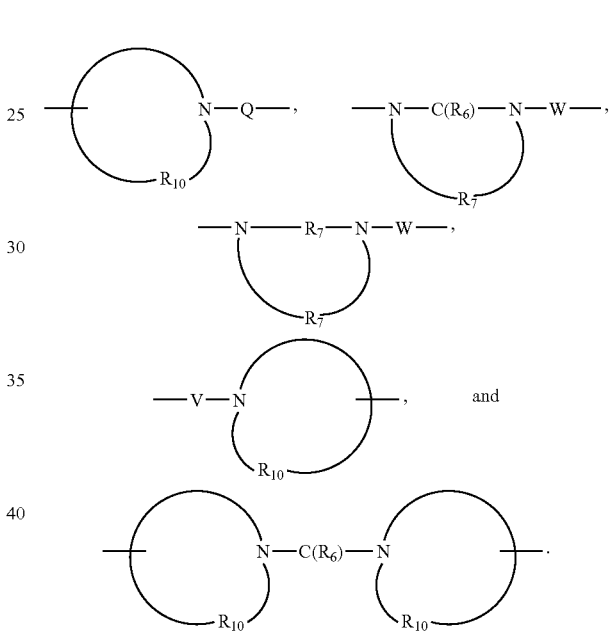

For certain embodiments, Z is a bond or —O—. For certain embodiments, Z is a bond. For certain embodiments, Z is —O—.

For certain embodiments, R is selected from the group consisting of halogen, hydroxy, alkyl, alkenyl, haloalkyl, alkoxy, alkylthio, and —N($R_9$)$_2$. For certain embodiments, R is hydroxy. For certain embodiments, R is halogen. For certain embodiments, R is fluoro. For certain embodiments, R is a substituent at the 2-position. For certain embodiments, R is a substituent at the 3-position.

For certain embodiments, $R_1$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, allylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy.

For certain embodiments, $R_1$ is not hydrogen or $C_{1-4}$ alkyl. For example, for certain embodiments of Formula I, when $R_A$ and $R_B$ together form a fused benzene ring that is unsubstituted or substituted by $C_{1-4}$ alkyl, $C_{1-4}$ alkoxy, or halogen, and Y is a bond, $R_1$ is not hydrogen or $C_{1-4}$ alkyl. For certain embodiments of Formula II, when $R_{A1}$ and $R_{B1}$ together form a fused benzene ring that is unsubstituted or substituted by $C_{1-4}$ alkyl, $C_{1-4}$ alkoxy, or halogen, and Y is a bond, $R_1$ is not hydrogen or $C_{1-4}$ alkyl. For certain embodiments of Formula IV, $R_1$ is not hydrogen or $C_{1-4}$ alkyl when Y is a bond, and either n and m are both 0, or m is 0, n is 1, and R is selected from the group consisting of $C_{1-4}$ alkyl, $C_{1-4}$ alkoxy, and halogen. For certain embodiments, particularly embodiments of Formulas III and IV, when Y is a bond, $R_1$ is not hydrogen or $C_{1-4}$ alkyl.

For certain embodiments, $R_1$ is $C_{1-3}$ alkyl. For certain embodiments, $R_1$ is methyl. For certain embodiments, $R_1$ is trifluoromethyl.

For certain embodiments, $R_3$ is selected from the group consisting of: —Z—$R_4$, —Z—X"—$R_4$, —Z—X"—Y—$R_4$, —Z—X"—Y'—X"—$R_4$, and —Z—X"—$R_5$. For certain embodiments, $R_3$ is pyridyl, benzyloxy, or 3-pyrrolylpropoxy. For certain embodiments, $R_3$ is at the 2-position. For certain embodiments, $R_3$ is at the 3-position.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. For certain embodiments, $R_4$ is aryl or heteroaryl.

For certain embodiments, $R_5$ is selected from the group consisting of

—N—C($R_6$),   —N—S(O)$_2$,   —V—N(CH$_2$)$_a$/(CH$_2$)$_b$ A, and
   $R_7$           $R_7$ —N—C($R_6$)—N(CH$_2$)$_a$/(CH$_2$)$_b$ A.
   $R_{10}$ For certain embodiments, $R_6$ is selected from the group consisting of =O and =S. For certain embodiments, $R_6$ is =O.

For certain embodiments, $R_7$ is $C_{2-7}$ alkylene.

For certain embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl.

For certain embodiments, $R_9$ is selected from the group consisting of hydrogen and alkyl.

For certain embodiments, $R_{10}$ is $C_{3-8}$ alkylene.

For certain embodiments, $R_{11}$ is selected from the group consisting of $C_{1-6}$ alkyl and —Si($C_{1-6}$ alkyl)$_3$. For certain embodiments, $R_1$, is —Si($C_{1-6}$ alkyl)$_3$. For certain embodiments, $R_{11}$ is a tert-butyldimethylsilanyl group.

For certain embodiments, R' is a non-interfering substituent. Herein, "non-interfering" means that the irnmunomodulator activity (for example, the ability to induce the biosynthesis of one or more cytokines or the ability to inhibit the biosynthesis of one or more cytokines) of the compound having a non-interfering substituent is not destroyed. Illustrative R' groups include those described herein for R and $R_3$.

For certain embodiments, A is selected from the group consisting of —CH$_2$—, —O—, —C(O)—, —S(O)$_{0-2}$—, and —N($R_4$)—.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$).

For certain embodiments, V is selected from the group consisting of —C($R_6$)—, —O—C($R_6$)—, —N($R_8$)—C($R_6$)—, and —S(O)$_2$—.

For certain embodiments, W is selected from the group consisting of a bond, —C(O)—, and —S(O)$_2$—.

For certain embodiments, a and b are independently integers from 1 to 6 with the proviso that a+b is ≦7. For certain embodiments, a and b are each 2.

For certain embodiments, m is 0 or 1; with the proviso that when m is 1, then n is 0 or 1. For certain embodiments, m is 0 or 1; with the proviso that when m is 1, then p is 0 or 1. For certain embodiments, m is 0. For certain embodiments, m is 1.

For certain embodiments, n is an integer from 0 to 4. For certain embodiments, n is 0. For certain embodiments, n is 1.

For certain embodiments, p is an integer from 0 to 3. For certain embodiments, p is 0.

For certain embodiments, particularly embodiments of Formulas III and IV, X is a bond and X' contributes one ring carbon atom. For certain embodiments, particularly embodiments of Formulas III and IV, X is a bond and X' contributes two ring carbon atoms.

For certain embodiments, Y is selected from the group consisting of —C(O)—, —S(O)$_2$—, or —C(O)—NH—, and $R_1$ is $C_{1-3}$ alkyl. For certain embodiments, particularly embodiments of Formulas III and IV, Y is —S(O)$_2$— and $R_1$ is methyl. For certain embodiments, Y is —S(O)$_2$— and $R_1$ is trifluoromethyl.

For certain embodiments, particularly embodiments of Formulas III and IV, m and n are 0.

For certain embodiments, particularly embodiments of Formulas III and IV, $R_1$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy; further with the proviso that when Y is a bond, $R_1$ is not hydrogen or $C_{1-4}$ alkyl.

In one embodiment, the present invention provides 9-(methylsulfonyl)-9,10,11,12-tetrahydro-8H-[1,4]diazepino[1',2':1,2]imidazo[4,5-c]quinolin-6-amine or a pharmaceutically acceptable salt thereof.

Preparation of the Compounds

Compounds of the invention can be prepared according to Reaction Scheme I, wherein R, $R_1$, X, X', Y, and n are as defined above, Hal is chloro, bromo, or iodo, and Boc is tert-butoxycarbonyl. Reaction Scheme I shows two routes to a 1H-imidazoquinolin-6-amine of Formula XVI; the routes are labeled Ia and Ib. In step (1) of Reaction Scheme I, a quinoline-3,4-diamine of Formula X is reacted with a carboxylic acid equivalent, which is selected such that it will provide the desired —X-Hal substituent in a 1H-imidazoquinoline of Formula XI. When the carboxylic acid equivalent is an acid halide of formula Hal-CH$_2$—X—C(O)Cl or Hal-CH$_2$—X—C(O)Br, the reaction is conveniently carried out by adding the acid halide to a solution of a quinoline-3,4-diamine of Formula X in a suitable solvent such as dichloromethane or 1,2-dichloroethane in the presence of a tertiary amine such as triethylamine. The reaction can be carried out at ambient temperature or at an elevated temperature. The product can be isolated by conventional methods.

The reaction with an acid halide of formula Hal-CH$_2$—X—C(O)Cl or Hal-CH$_2$—X—C(O)Br may be carried out in two parts, which include (i) adding the acid halide to a solution of a quinoline-3,4-diamine of Formula X in a suitable solvent such as dichloromethane or 1,2-dichloroethane optionally in the presence of a tertiary amine such as triethylamine to afford an amide intermediate and (ii) cyclizing to provide a 1H-imidazoquinoline of Formula XI. The amide intermediate from part (i) can be optionally isolated using conventional techniques. The cyclization in part (ii) may be carried out by heating the amide intermediate from part (i) in a suitable solvent such as toluene to provide a 1H-imidazo[4,5-c]quinoline of Formula XI. The cyclization in part (ii) can also be carried out in the presence of a base such as triethylamine.

Some compounds of Formula X are known; others can be made by known routes. See, for example, U.S. Pat. Nos. 6,331,539 (Crooks et al.), 6,451,485 (Crooks et al.), 6,451,810 (Coleman et al.), and 6,677,349 (Griesgraber).

In step (2) of Reaction Scheme I, a 1H-imidazoquinoline of Formula XI is cyclized by an intramolecular displacement of the halogen by the carbamate-protected amino group. The reaction is conveniently carried out by adding a base such as potassium tert-butoxide to a solution of a 1H-imidazoquinoline of Formula XI in a suitable solvent such as tetrahydrofuran. The reaction can be carried out at ambient temperature or at a sub-ambient temperature such as 0° C. The product can be isolated using conventional methods.

In step (3a) of Reaction Scheme I, a 1H-imidazo[4,5-c] quinoline of Formula XII is oxidized to provide a 1H-imidazo [4,5-c]quinoline-5N-oxide of Formula XIII using a conventional oxidizing agent capable of forming N-oxides. The reaction is conveniently carried out by adding 3-chloroperoxybenzoic acid to a solution of a compound of Formula XII in a solvent such as chloroform or dichloromethane. The reaction can be carried out at ambient temperature. The product can be isolated using conventional methods.

In step (4a) of Reaction Scheme I, a 1H-imidazo[4,5-c] quinoline-5N-oxide of Formula XIII is aminated to provide a 1H-imidazo[4,5-c]quinolin-6-amine of Formula XIV. Step (4a) involves the activation of an N-oxide of Formula XIII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XIII in a suitable solvent such as dichloromethane or chloroform and then adding p-toluenesulfonyl chloride. The reaction can be carried out at ambient temperature, and the product can be isolated from the reaction mixture using conventional methods.

In step (5a) of Reaction Scheme I, the Boc protecting group of a 1H-imidazo[4,5-c]quinolin-6-amine of Formula XIV is removed under acidic conditions to provide a 1H-imidazo[4,5-c]quinolin-6-amine of Formula XV. The deprotection is conveniently carried out by adding a solution of hydrogen chloride in 1,4-dioxane or a solution of trifluoroacetic acid in dichloromethane to the 1H-imidazo[4,5-c]quinolin-6-amine of Formula XIV. The reaction may be run in a suitable solvent such as dichloromethane. The reaction can be carried out at ambient temperature, and the product or pharmaceutically acceptable salt thereof can be isolated by conventional methods.

In step (6a) of Reaction Scheme I, the secondary amine of the 1H-imidazo[4,5-c]quinolin-6-amine of Formula XV or a salt thereof is converted to an amide, sulfonamide, sulfamide, urea, or tertiary amine of Formula XVI using conventional methods. Formula XVI represents a subgenus of Formulas I, II, III, and IV. In step (6a), a 1H-imidazo[4,5-c]quinolin-6-amine of Formula XV or a salt thereof can react with an acid chloride of Formula $R_1C(O)Cl$ to provide a compound of Formula XVI in which Y is —C(O)—. In addition, a 1H-imidazo[4,5-c]quinolin-6-amine of Formula XV can react with sulfonyl chloride of Formula $R_1S(O)_2Cl$ or a sulfonic anhydride of Formula $(R_1S(O)_2)_2O$ to provide a compound of Formula XVI in which Y is —S(O)$_2$—. Numerous acid chlorides of Formula $R_1C(O)Cl$, sulfonyl chlorides of Formula $R_1S(O)_2Cl$ and sulfonic anhydrides of Formula $(R_1S(O)_2)_2O$ are commercially available; others can be readily prepared using known synthetic methods. The reaction is conveniently carried out by adding the acid chloride of Formula $R_1C(O)Cl$, sulfonyl chloride of Formula $R_1S(O)_2Cl$ or sulfonic anhydride of Formula $(R_1S(O)_2)_2O$ to a solution of the compound of Formula XV in a suitable solvent such as chloroform, dichloromethane, or N,N-dimethylformamide (DMF). Optionally a base such as triethylamine or N,N-diisopropylethylamine can be added. The reaction can be carried out at ambient temperature or a sub-ambient temperature such as 0° C. The product or pharmaceutically acceptable salt thereof can be isolated using conventional methods.

Ureas of Formula XVI, where Y is —C(O)—N(R$_8$)— and R$_8$ is defined as above, can be prepared by reacting a 1H-imidazo[4,5-c]quinolin-6-amine of Formula XV or a salt thereof with isocyanates of Formula $R_1N=C=O$. Numerous isocyanates of Formula $R_1N=C=O$ are commercially available; others can be readily prepared using known synthetic methods. The reaction can be conveniently carried out by adding the isocyanate of Formula $R_1N=C=O$ to a solution of the 1H-imidazo[4,5-c]quinolin-6-amine of Formula XV in a suitable solvent such as DMF or chloroform. Optionally a base such as triethylamine or N,N-diisopropylethylamine can be added. The reaction can be carried out at ambient temperature or a sub-ambient temperature such as 0° C. Alternatively, a compound of Formula XV can be treated with an isocyanate of Formula $R_1(CO)N=C=O$, a thioisocyanate of Formula $R_1N=C=S$, a sulfonyl isocyanate of Formula $R_1S(O)_2N=C=O$, or a carbamoyl chloride of Formula $R_1N-(R_8)-C(O)Cl$ to provide a compound of Formula XVI, where Y is $-C(O)-N(R_8)-(CO)-$, $-C(S)-N(R_8)-$, $-C(O)-N(R_8)-S(O)_2-$, or $-C(O)-N(R_8)-$, respectively. Alternatively, a compound of Formula XV can be treated with a carbamoyl chloride of Formula Cl—C(O)-heterocyclyl, wherein heterocyclyl is attached at nitrogen atom, to provide a compound of Formula XVI, wherein Y is —C(O)— and $R_1$ is heterocyclyl attached at the nitrogen atom. The product or pharmaceutically acceptable salt thereof can be isolated using conventional methods.

Sulfamides of Formula XVI, where Y is $-S(O)_2-N(R_8)-$, can be prepared by reacting a compound or salt of Formula XV with sulfuryl chloride to generate a sulfamoyl chloride in situ, and then reacting the sulfamoyl chloride with an amine of formula $HN(R_8)R_1$. Alternatively, sulfamides of Formula XVI can be prepared by reacting a compound of Formula XV with a sulfamoyl chloride of formula $R_1(R_8)N—S(O)_2Cl$. The product or a pharmaceutically acceptable salt thereof can be isolated using conventional methods. Many sulfonyl chlorides of Formula $R_1S(O)_2Cl$ and amines of Formula $HN(R_8)R_1$, and some sulfamoyl chlorides of formula $R_1(R_8)N—S(O)_2Cl$ are commercially available; others can be prepared using known synthetic methods.

Compounds of Formula XVI where Y is a bond can be prepared by reductive alkylation of the secondary amine of the 1H-imidazo[4,5-c]quinolin-6-amine of Formula XV. The alkylation is conveniently carried out in two parts by (i) adding an aldehyde or ketone to a solution of a 1H-imidazo[4,5-c]quinolin-6-amine of Formula XV or a salt thereof in a suitable solvent such as DMF in the presence of a base such as N,N-diisopropylethylamine. In part (ii) the reduction is carried out by adding a suitable reducing agent such as the borane-pyridine complex. Both part (i) and part (ii) can be carried out at ambient temperature, and the product or pharmaceutically acceptable salt thereof can be isolated using conventional methods.

In steps (3b) and (4b) of Route Ib of Reaction Scheme I, the Boc protecting group of a 1H-imidazo[4,5-c]quinoline of Formula XII is first removed to product a 1H-imidazo[4,5-c]quinoline of Formula XVII or a pharmaceutically acceptable salt thereof, which is then converted to an amide, sulfonamide, urea, sulfamide, or tertiary amine of Formula XIII. Steps (3b) and (4b) of Route Ib can be carried out as described in steps (5a) and (6a) of Route Ia of Reaction Scheme I.

In steps (5b) and (6b) of Route Ib of Reaction Scheme I, a compound of Formula XVIII is first oxidized to a 1H-imidazo[4,5-c]quinoline-5N-oxide of Formula XIX, which is then aminated to provide a 1H-imidazo[4,5-c]quinolin-6-amine of Formula XVI. Steps (5b) and (6b) of Route Ib can be carried out as described in steps (3a) and (4a) of Route Ia of Reaction Scheme I. The product or pharmaceutically acceptable salt thereof can be isolated using conventional methods.

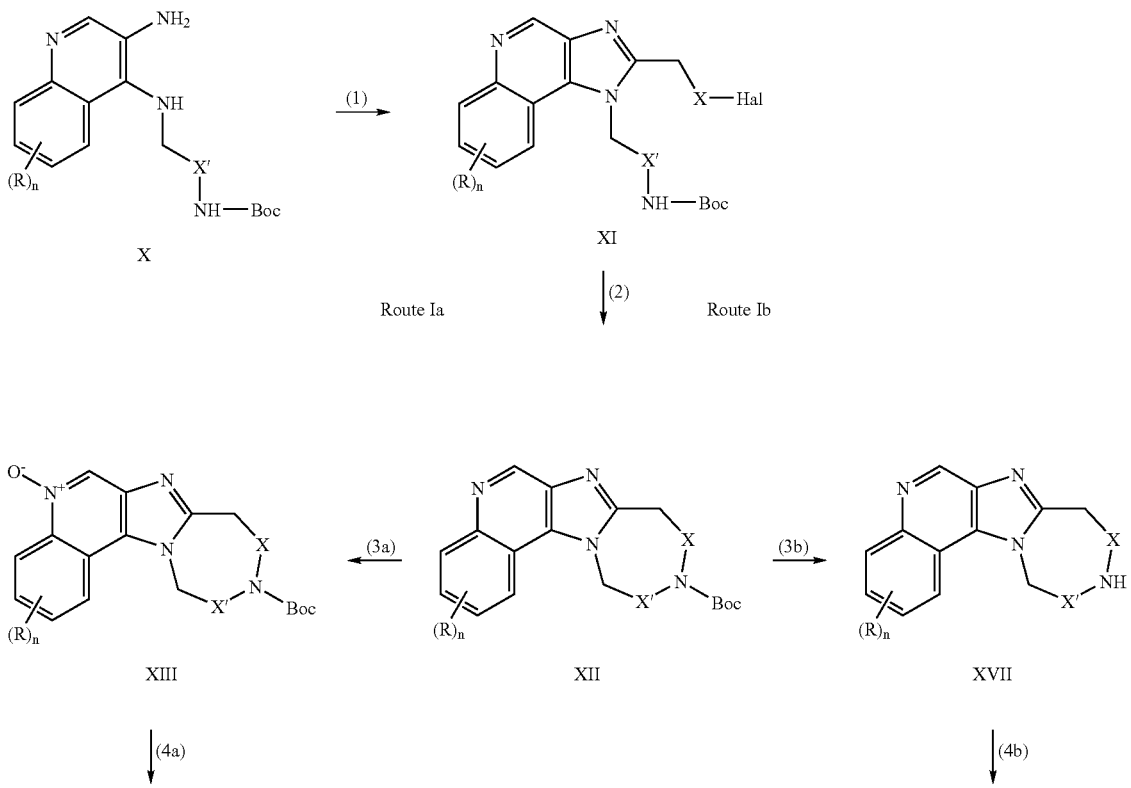

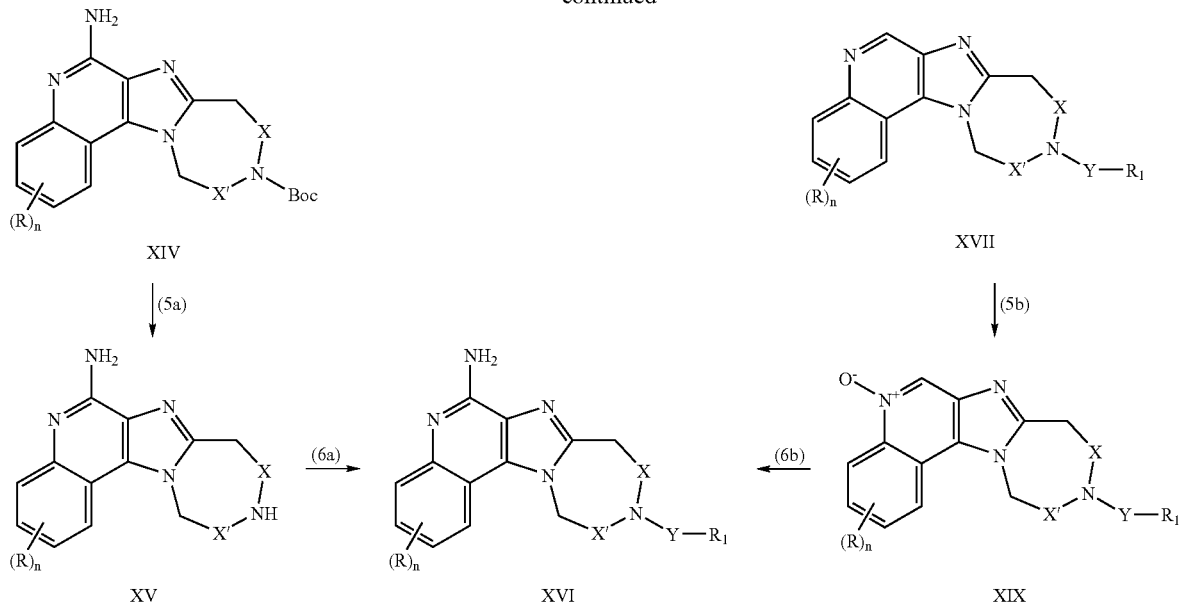

Compounds of the invention can also be prepared according to Reaction Scheme II, wherein R, $R_1$, X, X', Y, and n are as defined above and Hal is chloro, bromo, or iodo. In step (1) of Reaction Scheme II, a quinoline-3,4-diamine of Formula XX is reacted with an acid halide of formula Hal-$CH_2$—X—C(O)Cl or Hal-$CH_2$—X—C(O)Br to provide a 1H-imidazoquinoline of Formula XXI. The reaction is conveniently carried out as described for step (1a) of Reaction Scheme I.

Compounds of Formula XX are known or can be readily prepared using known synthetic routes; see for example, U.S. Pat. Nos. 4,689,338 (Gerster), 5,268,376 (Gerster), 6,331,539 (Crooks et al.), 6,451,810 (Coleman et al.), 6,541,485 (Crooks et al.).

In step (2) of Reaction Scheme II, a 1H-imidazoquinoline of Formula XXI is cyclized by an intramolecular displacement of the halogen by the carbamate-protected amino group. The reaction is conveniently carried out as described in step (2) of Reaction Scheme I to provide a compound of Formula XXII. Steps (1) and (2) may be effected in one step if the reaction in step (1) is heated at reflux for a day or two in a suitable solvent such as 1,2-dichloroethane.

In steps (3) and (4) of Reaction Scheme II, a compound of Formula XXII is first oxidized to a 1H-imidazo[4,5-c]quinoline-5N-oxide of Formula XXII, which is then aminated to provide a 1H-imidazo[4,5-c]quinolin-6-amine of Formula XVI. Steps (3) and (4) of Reaction Scheme II can be carried out as described in steps (3a) and (4a) of Route Ia of Reaction Scheme I. The product or pharmaceutically acceptable salt thereof can be isolated using conventional methods.

Reaction Scheme II

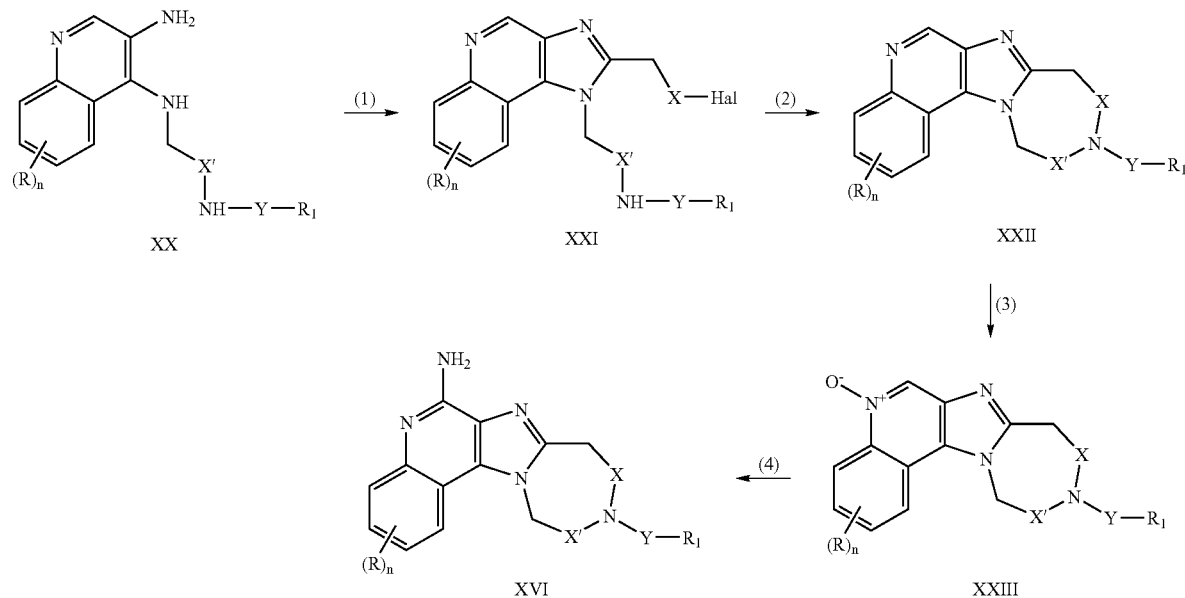

For some embodiments, compounds of the invention are prepared according to Reaction Scheme III, wherein R, $R_1$, X, X', Y, n, and Boc are as defined above; each Hal is independently chloro, bromo, or iodo; $R_{3a}$ is —Z—$R_{4b}$, —Z—$X''_a$—$R_4$, —Z—$X''_b$—Y'—$R_4$, or —Z—$X''_b$—$R_5$; where Z is a bond; $X''_a$ is alkenylene; $X''_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y' are as defined above. In step (1) of Reaction Scheme III, a quinoline-3,4-diamine of Formula XXIV is reacted with an acid halide of formula Hal-$CH_2$—X—C(O)Cl or Hal-$CH_2$—X—C(O)Br to provide a 1H-imidazoquinoline of Formula XXV. The reaction can be carried out as described in step (1) of Reaction Scheme I.

Compounds of Formula XXIV are known or can be readily prepared using known synthetic routes. See, for example, U.S. Pat. Nos. 6,331,539 (Crooks et al.), 6,451,485 (Crooks et al.), 6,451,810 (Coleman et al.), and 6,677,349 (Griesgraber) and U.S. Pat. Publication Application No. US 2004/0147543.

In step (2) of Reaction Scheme III, a 1H-imidazoquinoline of Formula XXV is cyclized by an intramolecular displacement of the halogen by the carbamate-protected amino group. The reaction can be carried out as described in step (2) of Reaction Scheme I to provide a compound of Formula XXVI.

In steps (3) and (4) of Reaction Scheme III, a compound of Formula XXVI is first oxidized to a 1H-imidazo[4,5-c]quinoline-5N-oxide of Formula XXVII, which is then aminated to provide a 1H-imidazo[4,5-c]quinolin-6-amine of Formula XXVIII. Steps (3) and (4) of Reaction Scheme III can be carried out as described in steps (3a) and (4a) of Route Ia of Reaction Scheme I.

In steps (5) and (6) of Reaction Scheme III, the Boc protecting group of a 1H-imidazo[4,5-c]quinolin-6-amine of Formula XXVIII is first removed to provide a 1H-imidazo[4,5-c]quinolin-6-amine of Formula XXIX or a pharmaceutically acceptable salt thereof. The compound of Formula XXIX is then converted to an amide, sulfonamide, urea, or sulfamide of Formula XXX in step (6). Steps (5) and (6) of Reaction Scheme III can be carried out as described in steps (5a) and (6a) of Route Ia of Reaction Scheme I.

In step (7) of Reaction Scheme III, a 1H-imidazo[4,5-c]quinolin-6-amine of Formula XXX is coupled with a boronic acid of Formula $R_{3a}$—B(OH)$_2$, an anhydride thereof, or a boronic acid ester of Formula $R_{3a}$—B(O-alkyl)$_2$ to provide an 1H-imidazo[4,5-c]quinolin-6-amine of Formula XXXI, which is a subgenus of Formulas I, II, III, and IV. The Suzuki coupling is carried out by combining a compound of Formula XXX with a boronic acid or an ester or anhydride thereof in the presence of palladium (II) acetate, triphenylphosphine, and a base such as sodium carbonate in a suitable solvent such as n-propanol or solvent mixture such as n-propanol/water. The reaction can be carried out at an elevated temperature (e.g., 80-100° C.). Many boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods. See, for example, Li, W. et al, *J. Org. Chem.*, 67, 5394-5397 (2002). The product of Formula XXXI or a pharmaceutically acceptable salt thereof can be isolated by conventional methods.

Other coupling reactions such as the Heck reaction, the Stille coupling, and the Sonogashira coupling can be used to prepare compounds of Formula XX. Also, compounds of Formula X, wherein $R_{3a}$ is —Z—$X''_a$—$R_4$, —Z—$X''_b$—Y'—$R_4$, and —Z—$X''_b$—$R_5$ in which $X''_b$ is alkenylene interrupted or terminated by arylene or heteroarylene, can undergo reduction of the $X''_a$ or $X''_b$ alkenylene group. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product or pharmaceutically acceptable salt thereof can be isolated using conventional methods.

Reaction Scheme III

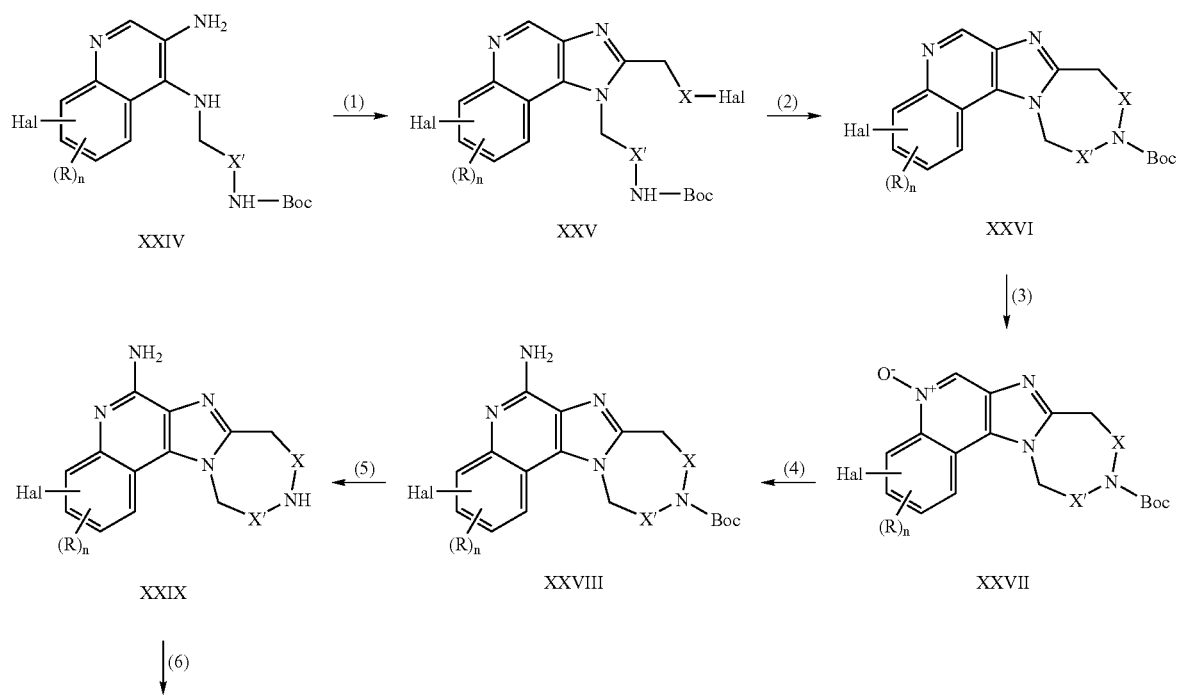

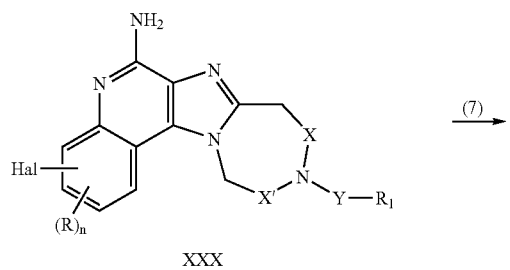 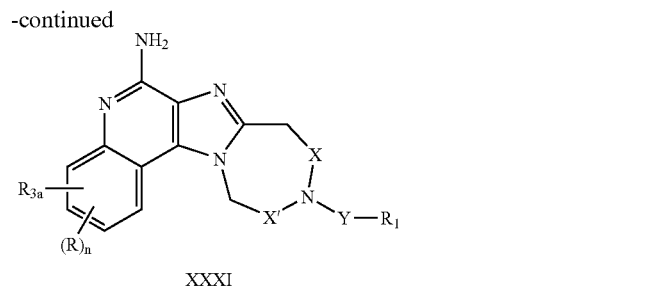

Compounds of the invention can be prepared according to Reaction Scheme IV where R, $R_1$, X, X', Y, n, and Boc are as defined above; $R_{3b}$ is —Z—$R_4$, —Z—X"—$R_4$, —Z—X"—Y'—$R_4$, —Z—X"—Y'—X"—Y'—$R_4$, or —Z—X"—$R_5$, where $R_4$, X', Y', and $R_5$ are as defined above; and Z is —O—. In step (1) of Reaction Scheme IV, a benzyloxyaniline of Formula XXXIII is treated with the condensation product generated from 2,2-dimethyl-1,3-dioxane-4,6-dione (Meldrum's acid) and triethyl orthoformate to provide an imine of Formula XXXIII. The reaction is conveniently carried out by adding a solution of a benzyloxyaniline of Formula XXXII to a heated mixture of Meldrum's acid and triethyl orthoformate and heating the reaction at an elevated temperature such as 45° C. The product can be isolated using conventional methods.

In step (2) of Reaction Scheme IV, an imine of Formula X Iundergoes thermolysis and cyclization to provide a benzyloxyquinolin-4-ol of Formula XXXIV. The reaction is conveniently carried out in a heat transfer fluid such as DOWTHERM A heat transfer fluid at a temperature between 200 and 250° C. The product can be isolated using conventional methods.

In step (3) of Reaction Scheme IV, the benzyloxyquinolin-4-ol of Formula XXXIV is nitrated under conventional nitration conditions to provide a benzyloxy-3-nitroquinolin-4-ol of Formula XXXV. The reaction is conveniently carried out by adding nitric acid to the benzyloxyquinolin-4-ol of Formula XXXIV in a suitable solvent such as propionic acid and heating the mixture at an elevated temperature such as 125° C. The product can be isolated using conventional methods.

In step (4) of Reaction Scheme IV, a benzyloxy-3-nitroquinolin-4-ol of Formula XXXV is chlorinated using conventional chlorination chemistry to provide a benzyloxy-4-chloro-3-nitroquinoline of Formula XXXVI. The reaction is conveniently carried out by treating the benzyloxy-3-nitroquinolin-4-ol of Formula XXXV with phosphorous oxychloride in a suitable solvent such as DMF. The reaction can be carried out at an elevated temperature such as 100° C., and the product can be isolated using conventional methods.

In step (5) of Reaction Scheme IV, a benzyloxy-4-chloro-3-nitroquinoline of Formula XXXVI is treated with an amine of Formula Boc—NH—X'—$CH_2$—$NH_2$ to provide a benzyloxy-3-nitroquinolin-4-amine of Formula XVIII. Several amines of Formula Boc—NH—X'—$CH_2$—$NH_2$ are commercially available; others can be prepared by known synthetic methods. The reaction is conveniently carried out by adding the amine of Formula Boc—NH—X'—$CH_2$—$NH_2$ to a solution of the benzyloxy-4-chloro-3-nitroquinoline of Formula XXXVI in a suitable solvent such as dichloromethane or methanol in the presence of a tertiary amine such as triethylamine. The reaction can be carried out at ambient temperature or at an elevated temperature such as, for example, the reflux temperature of the solvent. The reaction product can be isolated using conventional methods.

In step (6) of Reaction Scheme IV, a benzyloxy-3-nitroquinolin-4-amine of Formula XXXVI is reduced to provide a benzyloxyquinoline-3,4-diamine of Formula XXXVIII. The reaction can be carried out by hydrogenation using a heterogeneous hydrogenation catalyst such as platinum on carbon. The hydrogenation is conveniently carried out in a Parr apparatus in a suitable solvent such as toluene, methanol, or acetonitrile. The reaction can be carried out at ambient temperature, and the product can be isolated using conventional methods.

Alternatively, the reduction in step (6) can be carried out using nickel boride, prepared in situ from sodium borohydride and nickel(II) chloride. The reduction is conveniently carried out by adding a solution of the benzyloxy-3-nitroquinolin-4-amine of Formula XXVII in a suitable solvent or solvent mixture such as dichloromethane/methanol to a mixture of excess sodium borohydride and catalytic nickel(II) chloride in methanol. The reaction can be carried out at ambient temperature. The product can be isolated using conventional methods.

In step (7) of Reaction Scheme IV, a benzyloxyquinoline-3,4-diamine of Formula XXXVIII is treated with an acid halide of formula Hal-$CH_2$—X—C(O)Cl or Hal-$CH_2$—X—C(O)Br to provide a benzyloxy-1H-imidazo[4,5-c]quinoline of Formula XXXIX. The reaction can be carried out as described in step (1) of Reaction Scheme I.

In step (8) of Reaction Scheme IV, a benzyloxy-1H-imidazo[4,5-c]quinoline of Formula XXXIX is cyclized by an intramolecular displacement of the halogen by the carbamate-protected amino group. The reaction can be carried out as described in step (2) of Reaction Scheme I to provide a compound of Formula XL.

In steps (9) and (10) of Reaction Scheme IV, the Boc protecting group of a 1H-imidazo[4,5-c]quinoline of Formula XL is first removed to provide a 1H-imidazo[4,5-c]quinoline of Formula XLI or a pharmaceutically acceptable salt thereof. The compound of Formula XLI is then converted to an amide, sulfonamide, urea, or sulfamide of Formula XLII in step (10). Steps (9) and (10) of Reaction Scheme IV can be carried out as described in steps (5a) and (6a) of Route Ia of Reaction Scheme I.

In step (11) of Reaction Scheme IV, the benzyl group of a benzyloxy-1H-imidazo[4,5-c]quinoline of Formula XLII is cleaved to provide a 1H-imidazo[4,5-c]quinolinol of Formula XLIII. The cleavage is conveniently carried out on a Parr apparatus under hydrogenolysis conditions using a suitable heterogeneous catalyst such as palladium on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a benzyloxy-1H-imidazo[4,5-c]quinoline of Formula XLII in a suitable solvent such as ethanol in the presence of a catalyst such as palladium on carbon. The reaction is carried out at an elevated temperature, for example, the reflux temperature of the solvent. The product or pharmaceutically acceptable salt thereof can be isolated using conventional methods.

In step (12) of Reaction Scheme IV a 1H-imidazo[4,5-c]quinolinol of Formula XLIII is converted to an ether-substituted 1H-imidazo[4,5-c]quinoline of Formula XLIV using a Williamson-type ether synthesis. The reaction is effected by treating a 1H-imidazo[4,5-c]quinolinol of Formula XLIII with an alkyl halide of Formula Halide-$R_4$, Halide-$X''$—$Y'$—$R_4$, or Halide-$X''$—$R_5$ in the presence of a base. The reaction is conveniently carried out by combining a reagent of Formula Halide-$R_4$, Halide-$X''$—$Y'$—$R_4$, or Halide-$X'$—$R_5$ with a 1H-imidazo[4,5-c]quinolinol of Formula XLIII in a solvent such as DMF in the presence of a suitable base such as cesium carbonate. The reaction can be carried out at ambient temperature or at an elevated temperature, for example 65° C. or 85° C. Alternatively, the reaction can be carried out by treating a solution of a 1H-imidazo[4,5-c]quinolinol of Formula XLIII in a solvent such as DMF with sodium hydride and then adding a reagent of Formula Halide-$R_4$, Halide-$X''$—$Y'$—$R_4$, or Halide-$X''$—$R_5$. The product or pharmaceutically acceptable salt thereof can be isolated using conventional methods.

Numerous reagents of Formulas Halide-$R_4$ and Halide-$X''$—$Y'$—$R_4$ are commercially available, for example, substituted benzyl bromides and chlorides, substituted or unsubstituted alkyl or arylalkylenyl bromides and chlorides, substituted fluorobenzenes, bromo-substituted ketones, esters, and heterocycles. Other reagents of Formulas Halide-$R_4$, Halide-$X''$—$Y'$—$R_4$, or Halide-$X''$—$R_5$ can be prepared using conventional synthetic methods; for example, a bromo-substituted acid halide of Formula ClC(O)—$X''$—Br can be treated with a secondary amine in a suitable solvent such as dichloromethane to provide a variety of bromo-substituted amides of Formula Br—$X''$—C(O)—N($R_8$)—$R_4$ or

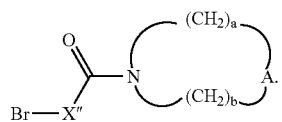

The reaction can be run at a sub-ambient temperature such as −25° C., and the product can be isolated using conventional methods.

Step (12) of Reaction Scheme IV can alternatively be carried out by treating a 1H-imidazo[4,5-c]quinolinol of Formula XLIII with an alcohol of Formula HO—$X''$—$Y'$—$R_4$, HO—$X''$—$R_5$, or HO—$R_4$ under Mitsunobu reaction conditions. Numerous alcohols of these formulas are commercially available, and others can be prepared using conventional synthetic methods. The reaction is conveniently carried out by out by adding triphenylphosphine and an alcohol of Formula HO—$X''$—$Y'$—$R_4$, HO—$X''$—$R_5$, or HO—$R_4$ to a solution of a 1H-imidazo[4,5-c]quinolinol of Formula XLIII in a suitable solvent such as tetrahydrofuran and then slowly adding diisopropyl azodicarboxylate or diethyl azodicarboxylate. The reaction can be carried out at ambient temperature or at a sub-ambient temperature, such as 0° C. The product can be isolated using conventional methods.

In steps (13) and (14) of Reaction Scheme IV, an ether-substituted 1H-imidazo[4,5-c]quinoline of Formula XLIV is first oxidized to a 1H-imidazo[4,5-c]quinoline-5N-oxide of Formula XLV, which is then aminated to provide a 1H-imidazo[4,5-c]quinolin-6-amine of Formula XLVI, a subgenus of Formula II. Steps (13) and (14) of Reaction Scheme IV can be carried out as described in steps (3a) and (4a) of Route Ia of Reaction Scheme I. The product or pharmaceutically acceptable salt thereof can be isolated using conventional methods.

Reaction Scheme IV

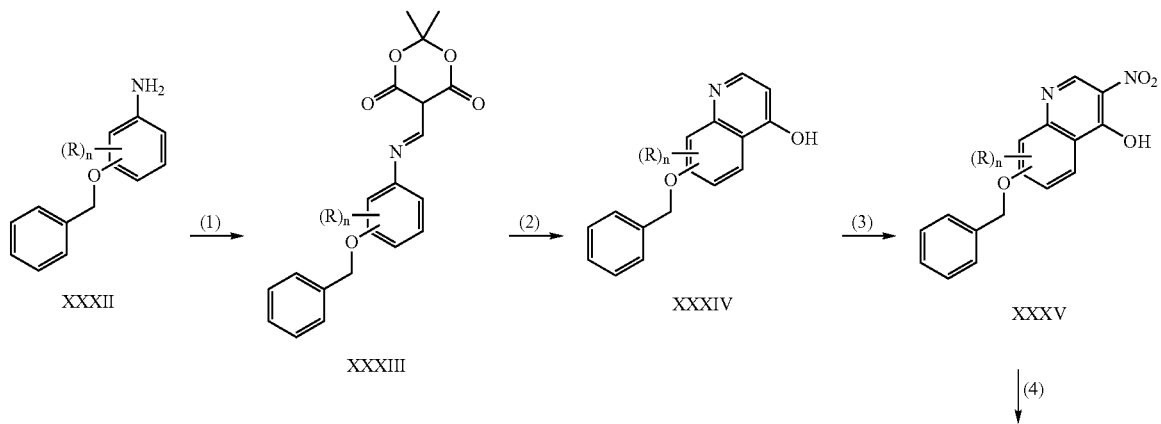

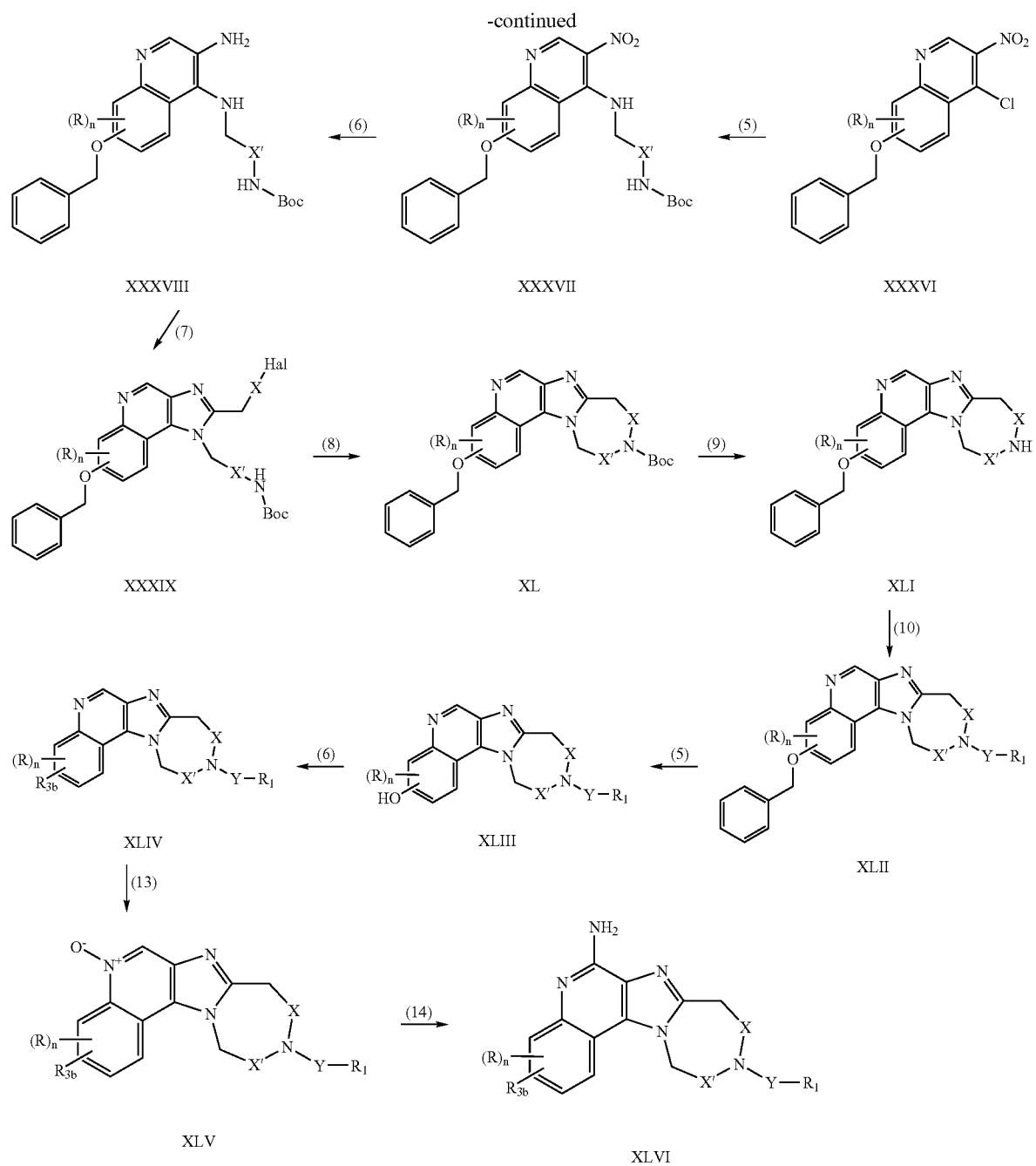

Imidazopyridines of the invention can be prepared according to Reaction Scheme V, where $R_1$, $R_{A2}$, $R_{B2}$, X, X', Y, Boc, and Hal are as defined above, and Ph is phenyl. In step (1) of Reaction Scheme V, a 2-phenoxypyridine-3,4-diamine of Formula XLVII is converted to a 1H-imidazo[4,5-c]pyridine of Formula XLVI by reaction with an acid halide of formula Hal-CH$_2$—X—C(O)Cl or Hal-CH$_2$—X—C(O)Br or another carboxylic acid equivalent. The reaction can be carried out as described in step (1) of Reaction Scheme I. When X is a bond, the reaction is conveniently carried out by combining a 2-phenoxypyridine-3,4-diamine of Formula XLVII with ethyl chloroacetimidate hydrochloride in a suitable solvent such as chloroform. The reaction can be carried out at an elevated temperature such as 60° C., and the product can be isolated by conventional methods. Several 2-phenoxypyridine-3,4-diamines of Formula XLVII are known or can be prepared by published methods. See, for example, U.S. Pat. No. 6,545,016 and PCT Publication No. WO 03/103584. Ethyl chloroacetimidate hydrochloride is a known compound that can be prepared according to the literature procedure: Stillings, M. R. et al., *J. Med. Chem.*, 29, pp. 2280-2284 (1986).

In step (2) of Reaction Scheme V, a halogen-substituted 1H-imidazo[4,5-c]pyridine of Formula XLVIII undergoes an intramolecular displacement of the halogen by the carbamate-protected amino group to provide a 4-phenoxy-1H-imidazo[4,5-c]pyridine of Formula XLIX. The reaction can be carried out as described in step (2) of Reaction Scheme I. Alternatively, the reaction with potassium tert-butoxide may be carried out at an elevated temperature such as 60° C., and a solvent mixture such as THF/dichloromethane can be used. The product can be isolated by conventional methods.

In step (3) of Reaction Scheme V, a 4-phenoxy-1H-imidazo[4,5-c]pyridine of Formula XLIX is aminated and simultaneously deprotected to provide a 1H-imidazo[4,5-c]pyridin-4-amine of Formula L, a subgenus of Formulas I, II, and VII. The reaction is conveniently carried out by adding a solution of ammonia in a suitable solvent such as methanol to a compound of Formula XLIX and heating the reaction at an elevated temperature such as 170° C. Under these conditions, the Boc group of a compound of Formula XLIX is removed to provide a compound of Formula L. The product or pharmaceutically acceptable salt thereof can be isolated by conventional methods.

Alternatively, the amination in step (3) may be carried out by heating a 4-phenoxy-1H-imidazo[4,5-c]pyridine of Formula XLIX with ammonium acetate at an elevated temperature such as 150° C. This reaction provides a 1H-imidazo[4,5-c]pyridin-4-amine of Formula VII, wherein Y is —C(O)— and $R_1$ is methyl. This acetamide can be treated with concentrated hydrochloric acid at an elevated temperature such as 90° C. in a suitable solvent such as ethanol to provide an amine of Formula L. A 1H-imidazo[4,5-c]pyridin-4-amine of Formula L or a pharmaceutically acceptable salt thereof can be isolated by conventional methods.

In step (4) of Reaction Scheme V, the secondary amine of a 1H-imidazo[4,5-c]pyridin-4-amine of Formula L or a salt thereof is converted to an amide, sulfonamide, sulfamide, urea, or tertiary amine of Formula VII using one of the methods described in step (6a) of Reaction Scheme I. The product or pharmaceutically acceptable salt thereof can be isolated by conventional methods.

Imidazonaphthyridines of the invention can be prepared according to Reaction Scheme VI, wherein $R_1$, R, X, X', Y, Boc, Hal, and p are as defined above. In step (1) of Reaction Scheme VI, a naphthyridine-3,4-diamine of Formula LI is reacted with an acid halide of formula Hal-CH$_2$—X—C(O)Cl or Hal-CH$_2$—X—C(O)Br or another carboxylic acid equivalent to provide a 1H-imidazonaphthyridine of Formula LII. The reaction can be carried out according to either the one-step or two-step procedure described in step (1) of Reaction Scheme I. If the two-step procedure is used, part (ii) of step (1) can be carried out by treating the amide prepared in part (i) with a base such as aqueous sodium hydroxide, aqueous potassium carbonate, or triethylamine to provide a 1H-imidazo[4,5-c][1,5]naphthyridine of Formula LII. The reaction is conveniently carried out in a suitable solvent such as ethanol or in ethanol/water at ambient temperature or at an elevated temperature such as 40° C. Alternatively, when X is a bond, the reaction can be carried out by combining a naphthyridine-3,4-diamine of Formula LI with ethyl chloroacetimidate hydrochloride under the reaction conditions described in step (1) of Reaction Scheme V. Some compounds of Formula LI are known; others can be prepared using known methods. See, for example, U.S. Pat. No. 6,194,425 (Gerster et al.), particularly Examples 42 and 86.

In step (2) of Reaction Scheme VI, the Boc protecting group of a 1H-imidazonaphthyridine of Formula LII is removed under acidic conditions to provide a 1H-imidazonaphthyridine of Formula LIII. The deprotection can be carried out using the methods described in step (5a) of Reaction Scheme I, and the product or a salt thereof can be isolated by known methods.

In step (3) of Reaction Scheme VI, the amine of a 1H-imidazo[4,5-c]naphthyridine of Formula LIII or a salt thereof is converted to an amide, sulfonamide, sulfamide, urea, or secondary amine of Formula LIV using one of the methods

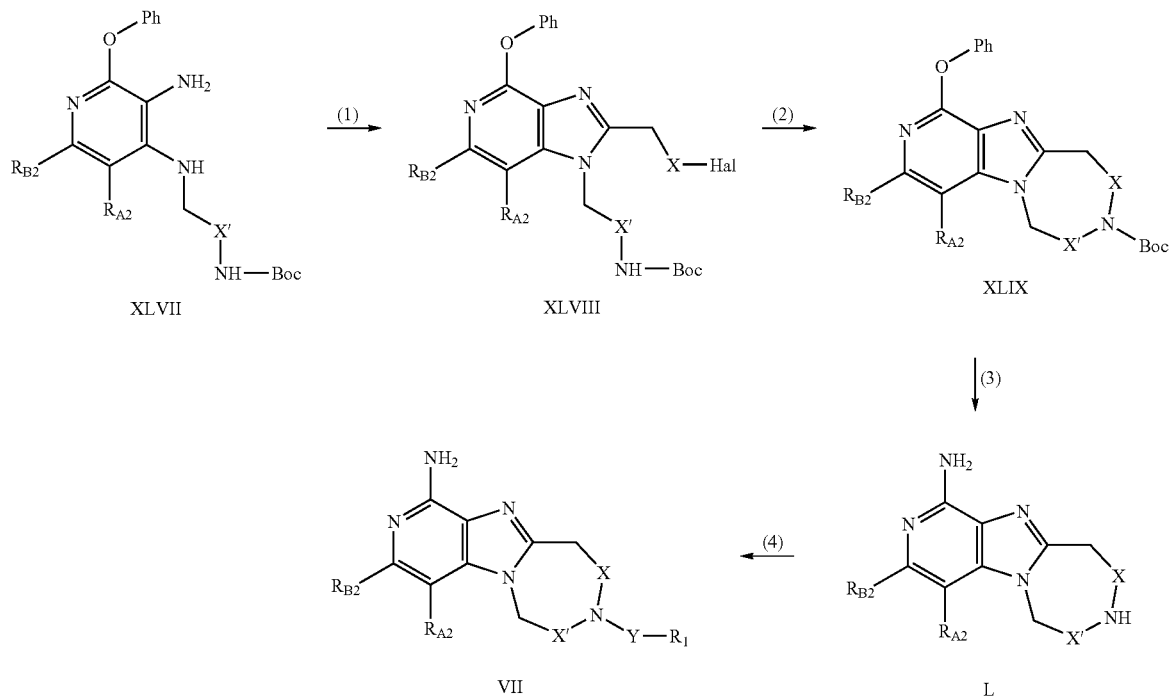

described in step (6a) of Reaction Scheme I. The product or pharmaceutically acceptable salt thereof can be isolated by conventional methods.

In step (4) of Reaction Scheme VI, a 1H-imidazo[4,5-c]naphthyridine of Formula LIV undergoes an intramolecular displacement of the halogen by the amide, sulfonamide, sulfamide, urea, or secondary amino group. The reaction can be carried out under the conditions described in step (2) of Reaction Scheme I. Alternatively, a base such as cesium carbonate can be used to effect the cyclization in a solvent such as acetone. The product of Formula V can be isolated by conventional methods.

solvent such as dichloromethane or chloroform and then adding ammonium hydroxide and p-toluenesulfonyl chloride. The product or pharmaceutically acceptable salt thereof can be isolated by conventional methods.

A 1H-imidazonaphthyridine of Formula LII can also be converted into a 1H-imidazo[4,5-c]naphthyridin-6-amine of Formula LVII using either Route Ia or Route Ib shown in Reaction Scheme I. In addition a naphthyridine-3,4-diamine of Formula LI can be treated first according to the methods of steps (2) and (3) of Reaction Scheme VI and subsequently treated according to steps (1) through (4) of Reaction Scheme II to provide compounds of Formula LVII.

Reaction Scheme VI

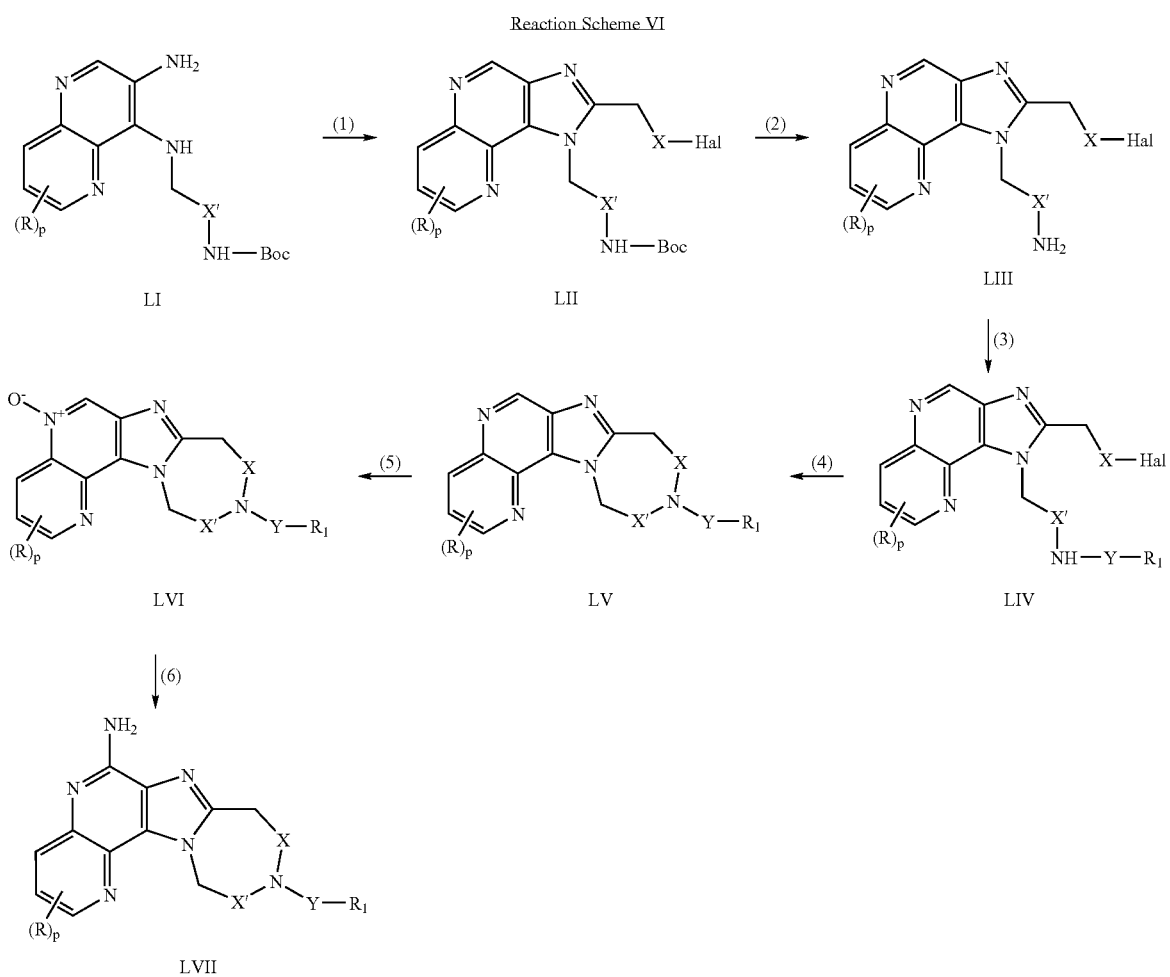

In steps (5) and (6) of Reaction Scheme VI, a 1H-imidazo[4,5-c]naphthyridine of Formula LV is first oxidized to a 1H-imidazo[4,5-c]naphthyridine-5N-oxide of Formula LVI, which is then aminated to provide a 1H-imidazo[4,5-c]naphthyridin-6-amine of Formula LVII, a subgenus of Formulas I, II, and VI. Steps (5) and (6) of Reaction Scheme VI can be carried out according to the methods of steps (3a) and (4a) of Reaction Scheme I. Alternatively, the oxidation and amination can be carried out as a one-pot procedure without isolating the N-oxide of Formula LVI by adding 3-chloroperoxybenzoic acid to a solution of a compound of Formula LV in a For some embodiments, naphthyridines of the invention can be prepared from tetrazolo compounds of Formulas LVIII and LXII according to Reaction Schemes VII and VIII, wherein $R_1$, R, X, X', Y, Boc, and p are as defined above. Compounds of Formulas LVII and LXII can be prepared by known synthetic routes; see, for example, U.S. Pat. No. 6,194,425 (Gerster et al.). The tetrazolo compounds of Formulas LVIII and LXII can each be treated according to the methods of steps (1) and (2) of Reaction Scheme I to provide compounds of Formulas LIX and LXIII, respectively.

In step (3) of Reaction Scheme VII, the tetrazolo and Boc groups are removed from a compound of Formula LIX to provide a 1H-imidazo[4,5-c]naphthyridin-6-amine of Formula LX. Removal of a tetrazolo group can be carried out in two steps by first treating the compound of Formula LIX with triphenylphosphine and then hydrolyzing the resulting intermediate. The reaction conditions described in U.S. Pat. No. 6,194,425 can be used. Under the hydrolysis conditions, the Boc protecting group is also removed. The product of Formula LX or a pharmaceutically acceptable salt thereof can be isolated by conventional methods.

In step (4) of Reaction Scheme VII, the secondary amine of a 1H-imidazo[4,5-c]naphthyridin-4-amine of Formula LX or a salt thereof is converted to an amide, sulfonamide, sulfamide, urea, or tertiary amine of Formula LXI using one of the methods described in step (6a) of Reaction Scheme I. The product or pharmaceutically acceptable salt thereof can be isolated by conventional methods.

Steps (3) and (4) of Reaction Scheme VIII can be carried out in the same manner described for steps (3) and (4) of Reaction Scheme VII, and the products of Formulas LXI and LXV are subgenera Formulas I and II.

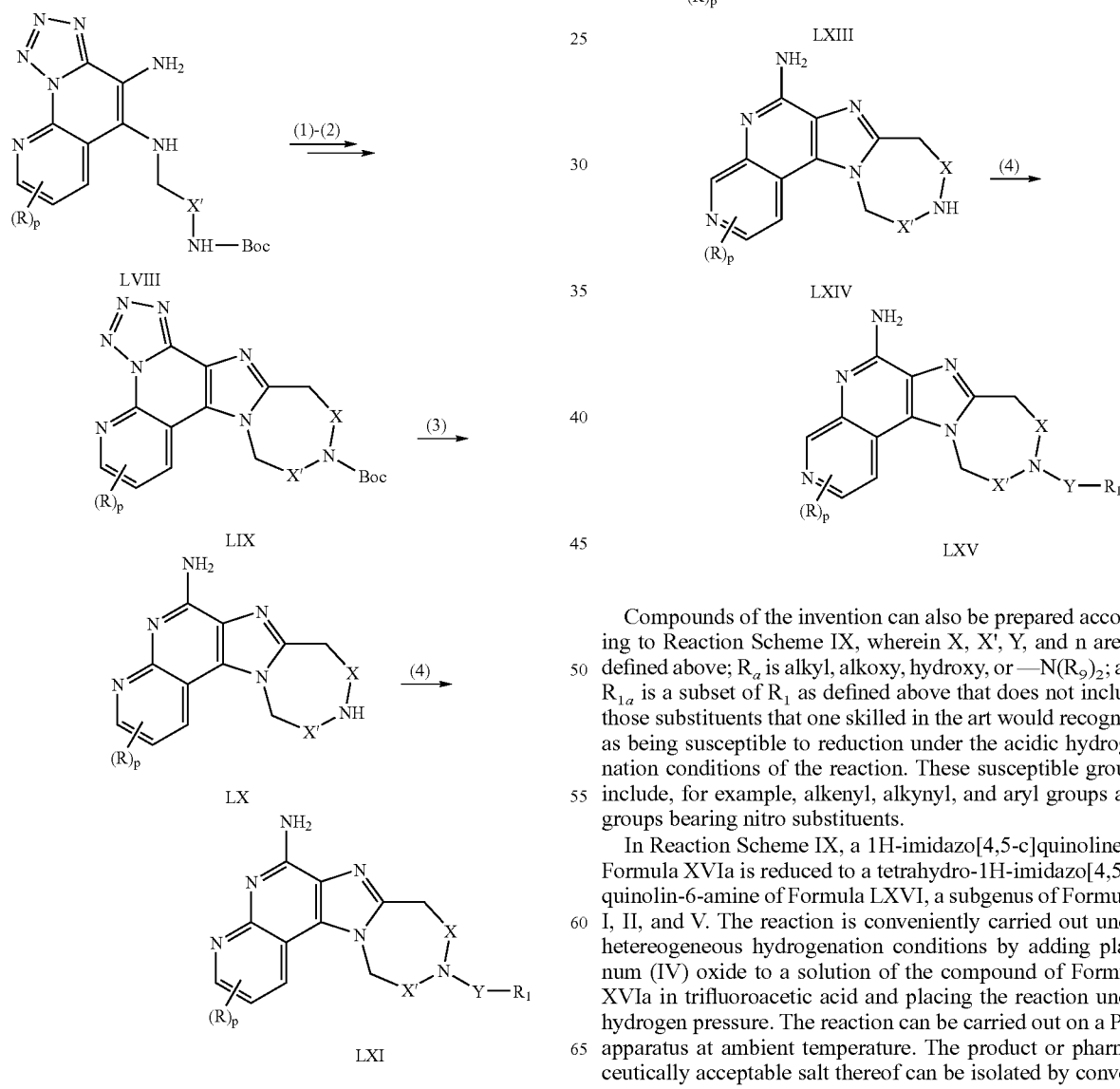

Reaction Scheme VII

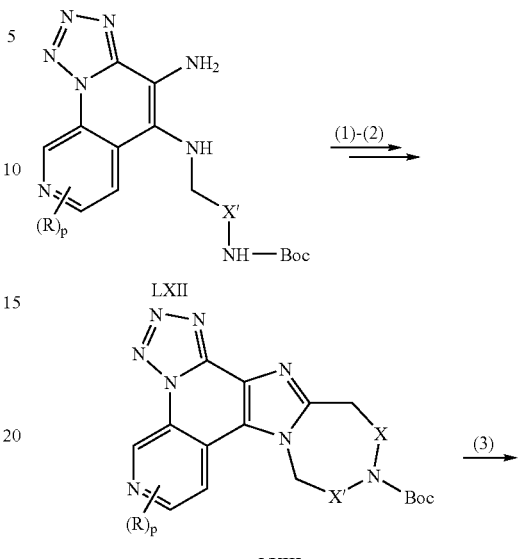

Reaction Scheme VIII

Compounds of the invention can also be prepared according to Reaction Scheme IX, wherein X, X', Y, and n are as defined above; $R_a$ is alkyl, alkoxy, hydroxy, or $-N(R_9)_2$; and $R_{1a}$ is a subset of $R_1$ as defined above that does not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

In Reaction Scheme IX, a 1H-imidazo[4,5-c]quinoline of Formula XVIa is reduced to a tetrahydro-1H-imidazo[4,5-c]quinolin-6-amine of Formula LXVI, a subgenus of Formulas I, II, and V. The reaction is conveniently carried out under hetereogeneous hydrogenation conditions by adding platinum (IV) oxide to a solution of the compound of Formula XVIa in trifluoroacetic acid and placing the reaction under hydrogen pressure. The reaction can be carried out on a Parr apparatus at ambient temperature. The product or pharmaceutically acceptable salt thereof can be isolated by conventional methods.

Reaction Scheme IX

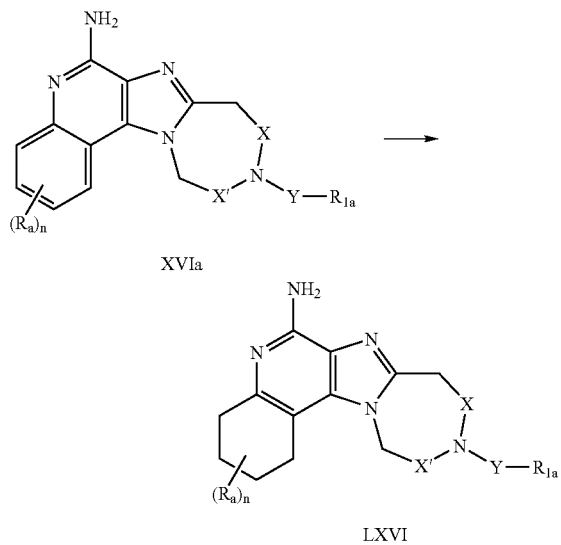

The reduction described in Reaction Scheme IX can also be used to prepare a tetrahydro-1H-imidazo[4,5-c][1,5]naph-thyridin-6-amine of Formula LXVII, as shown in Reaction Scheme X, wherein X, X', Y, n, $R_a$, and $R_{1a}$ are as defined above. The product of Formula LXVII, a subgenus of Formulas I and II, or a pharmaceutically acceptable salt thereof can be isolated by conventional methods.

Reaction Scheme X

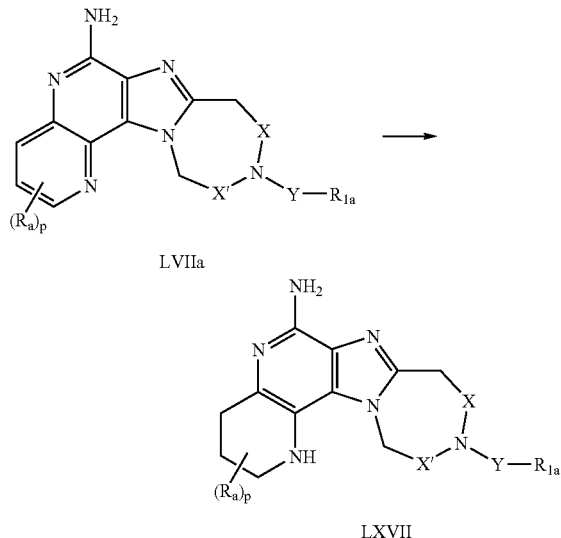

Compounds of the invention can also be prepared using variations of the synthetic routes shown in Reaction Schemes I through X that would be apparent to one of skill in the art. For example, the synthetic route shown in Reaction Scheme III for the preparation of quinolines having a $R_{3a}$ substituent can be used to prepare [1,5]naphthyridines having a $R_{3a}$ substituent by using a bromo substituted 4-chloro-3-nitro[1,5] naphthyridine in lieu of the bromo substituted 4-chloro-3-nitroquinoline. Also, a benzyloxy-substitued aminopyridine, in one of several isomeric forms, can be used as the starting material in Reaction Scheme IV to provide a naphthyridine having an $R_{3b}$ substituent. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics; antibodies, proteins, peptides, oligonucleotides, etc.

Compounds or salts of the invention have been shown to induce and/or inhibit the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5, and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, an IRM compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain IRM compounds or salts of the present invention may be particularly helpful in individuals having compromised immune function. For example, certain compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

In the examples below, some of the compounds were purified by preparative high performance liquid chromatography (prep HPLC) using a Waters Fraction Lynx automated purification system. The prep HPLC fractions were analyzed using a Micromass LC/TOF-MS, and the appropriate fractions were combined and centrifuge evaporated to provide the trifluoroacetate salt of the desired compound. In order to maximize purity, some of the compounds were sent through the purification process twice. A variety of chromatographic conditions were used for separations. Column: Phenomenex LUNA C18(2), 21.2×50 millimeters (mm), 10 micron particle size; or Waters XTERRA C18, 19×50 millimeters (mm), 5 micron particle size; non-linear gradient elution from 5 to 95% B where A is 0.05% trifluoroacetic acid/water and B is 0.05% trifluoroacetic acid/acetonitrile; fraction collection by mass-selective triggering.

Example 1

11-{[tert-Butyl(dimethyl)silyl]oxy}-9-(methylsulfonyl)-9,10,11,12-tetrahydro-8H-[1,4]diazepino[1',2':1,2]imidazo[4,5-c]quinolin-6-amine

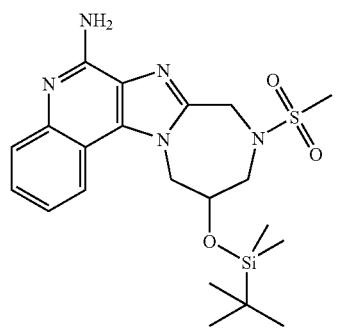

Part A

Under a nitrogen atmosphere, a solution of di-tert-butyl dicarbonate (145.35 g, 665.98 mmol) in 1,4-dioxane (400 mL) was added dropwise with stirring to a solution of 2-hydroxy-1,3-diaminopropane (300.00 g, 332.85 mmol) in methanol (500 mL) over a period of six hours. The reaction was stirred overnight at ambient temperature and then concentrated under reduced pressure. The residue was dissolved in 10% citric acid in water, and additional citric acid was added to adjust the solution to pH 4. The resulting solution (1-1.5 L) was washed with dichloromethane (3×500 mL) and then adjusted to pH 12 with the addition of 50% aqueous sodium hydroxide. The basic solution was extracted with chloroform (7×500 mL), and the combined extracts were concentrated under reduced pressure and dried overnight under high vacuum to provide 108.19 g of tert-butyl 3-amino-2-hydroxypropylcarbamate as a white solid.

Part B

Under a nitrogen atmosphere, triethylamine (72 g, 710 mmol) was added to a solution of 4-chloro-3-nitroquinoline (98.9 g, 474 mmol) in N,N-dimethylformamide (DMF) (1 L). A solution of tert-butyl 3-amino-2-hydroxypropylcarbamate (108.19 g, 569 mmol) in dioxane (800 mL) was slowly added, and the reaction was stirred overnight at ambient temperature and then poured into water (3 L) with continuous stirring. A precipitate formed and was isolated by filtration, washed with water, and dried for three days in a vacuum oven at 65° C. to provide 167.54 g of tert-butyl 2-hydroxy-3-[(3-nitroquinolin-4-yl)amino]propylcarbamate as a bright yellow powder.

Part C

Triethylamine (111.7 g, 1.104 mol) was added to a solution of tert-butyl 2-hydroxy-3-[(3-nitroquinolin-4-yl)amino]propylcarbamate (100.0 g, 275.95 mmol) in DMF (400 mL). A solution of tert-butyldimethylsilyl chloride (TBDMSCl) (91.5 g, 607 mmol) in DMF (140 mL) was slowly added, and the reaction was stirred overnight at ambient temperature. An analysis by high-performance liquid chromatography (HPLC) indicated the presence of starting material, and additional triethylamine (1 equivalent) and TBDMSCl (0.5 equivalent) were added. The reaction was stirred overnight at ambient temperature, and a large excess of TBDMSCl was added. The product mixture was filtered to remove a solid, and the filtrate was concentrated under reduced pressure. The residue was dissolved in chloroform, and the resulting solution was washed with aqueous ammonium chloride (3×), aqueous sodium bicarbonate (2×), and brine and then concentrated under reduced pressure. The resulting solid was dried overnight under high vacuum. The crude solid was recrystalized from acetonitrile, and two crops of crystals were collected to provide 110.18 g of tert-butyl 2-{[tert-butyl(dimethyl)silyl]oxy}-3-[(3-nitroquinolin-4-yl)amino] propylcarbatnate as a white powder.

Part D

A solution of tert-butyl 2-{[tert-butyl(dimethyl)silyl]oxy}-3-[(3-nitroquinolin-4-yl)amino]propylcarbamate (110.18 g, 231.16 mmol) in dichloromethane (500 mL) was added to a Parr vessel. The system was purged with nitrogen, and 10% palladium on carbon (14.76 g, 138.7 mnmol) was added. The vessel was placed under hydrogen pressure (30 psi, $2.1 \times 10^5$ Pa) and shaken for four hours. The reaction mixture was filtered, and, the filtrate was passed through a plug of silica gel and concentrated under reduced pressure to provide 103.45 g of tert-butyl 3-[(3-aminoquinolin-4-yl) amino]-2-{[tert-butyl(dimethyl)silyl]oxy}propylcarbamate.

51

Part E

Triethylamine (46.2 g, 456 mmol) was added to a solution of tert-butyl 3-[(3-aminoquinolin-4-yl)amino]-2-{[tert-butyl (dimethyl)silyl]oxy}propylcarbamate (101.9 g, 228.1 mmol) in 1,2-dichloroethane (600 mL). A solution of chloroacetyl chloride (28.3 g, 251 mmol) in 1,2-dichloroethane was added dropwise, and the reaction was stirred overnight at ambient temperature. The reaction mixture was filtered to remove a solid, and the filtrate was concentrated under reduced pressure. The crude product was purified by column chromatography on silica gel (eluting sequentially with 95.5:0.5 and 95:5 dichloromethane:methanol), and the purified product was dried overnight under high vacuum to provide 71.93 g of tert-butyl 2-{[tert-butyl(dimethyl)silyl]oxy}-3-[2-(chloromethyl)-1H-imidazo[4,5-c]quinolin-1-yl]propylcarbamate.

Part F

Potassium tert-butoxide (116.1 mL of a 1M solution in tetrahydrofuran) was added to a solution of tert-butyl 2-{[tert-butyl(dimethyl)silyl]oxy}-3-[2-(chloromethyl)-1H-imidazo[4,5-c]quinolin-1-yl]propylcarbamate (42.72 g, 84.57 mmol) in anhydrous tetrahydrofuran (THF) (50 mL), and the reaction was stirred overnight at ambient temperature and then concentrated under reduced pressure. The crude product was purified by column chromatography on silica gel (eluting with dichloromethane:methanol in a gradient from 99:1 to 95:5) to provide 20.23 g of tert-butyl 11-{[tert-butyl(dimethyl)silyl]oxy}-11,12-dihydro-8H-[1,4]diazepino[1',2':1,2]imidazo[4,5-c]quinoline-9(10H)-carboxylate.

Part G

Trifluoroacetic acid (500 mL of a 10% solution in dichloromethane) was added to tert-butyl 11-{[tert-butyl(dimethyl)silyl]oxy}-11,12-dihydro-8H-[1,4]diazepino[1',2':1,2]imidazo[4,5-c]quinoline-9(10H)-carboxylate (9.23 g, 19.7 mmol), and the reaction was stirred at ambient temperature for 75 minutes. The solvent was removed under reduced pressure, and the residue was shaken with triethylamine (300 mL) and dichloromethane. The solution was concentrated under reduced pressure, and the product was dried under high vacuum for two hours to provide 11-{[tert-butyl(dimethyl)silyl]oxy}-9,10,11,12-tetrahydro-8H-[1,4]diazepino[1',2':1,2]imidazo[4,5-c]quinoline, which was used in the next step without removing the triethylamine trifluoroacetate salt.

Part H

Triethylamine (7.97 g, 78.8 mmol) was added to a solution of the material from Part G in dichloromethane (500 mL). Methanesulfonyl chloride (2.71 g, 23.6 mmol) was slowly added. The reaction was stirred at ambient temperature for one hour, washed with brine and sodium bicarbonate, and concentrated under reduced pressure. The residue was dried for two days under high vacuum to provide 8.78 g of 11-{[tert-butyl(dimethyl)silyl]oxy}-9-(methylsulfonyl)-9,10,11,12-tetrahydro-8H-[1,4]diazepino[1',2':1,2]imidazo[4,5-c]quinoline. The product was combined with material made in a separate run.

Part I

3-Chloroperoxybenzoic acid (9.92 g of 77% pure material, 57.47 mmol) (mCPBA) was added to a solution of 11-{[tert-butyl(dimethyl)silyl]oxy}-9-(methylsulfonyl)-9,10,11,12-tetrahydro-8H-[1,4]diazepino[1',2':1,2]imidazo[4,5-c]quinoline (16.47 mmol) in chloroform (200 mL), and the reaction was stirred overnight at ambient temperature. Additional mCPBA (1-1.5 equivalents) was added, and the reaction was stirred for two hours, washed with brine and sodium bicarbonate, and concentrated under reduced pressure.

Part J

Ammonium hydroxide (150 mL) was added with vigorous stirring to a solution of the material from Part I in chloroform (200 mL). p-Toluenesulfonyl chloride (7.73 g, 40.6 mmol) was added in portions, and the reaction was stirred overnight and then concentrated under reduced pressure. The residue was dissolved in chloroform and poured into ethyl acetate (800 mL) to form a precipitate, which was isolated by filtration and washed with methanol. The filtrate was concentrated under reduced pressure, and the residue was dissolved in ethyl acetate (50 mL) and refrigerated overnight. Crystals formed and were isolated by filtration, and two additional crops of crystals were obtained in the same manner. The crystals were combined and dried in a vacuum oven to provide 6.69 g of 11-{[tert-butyl(dimethyl)silyl]oxy}-9-(methylsulfonyl)-9,10,11,12-tetrahydro-8H-[1,4]diazepino[1',2':1,2]imidazo[4,5-c]quinolin-6-amine as white crystals, mp 256-258° C.

$^1$H NMR (300 MHz, DMSO-$d_6$) δ 8.12 (d, J=8.0 Hz, 1H), 7.51 (d, J=8.3 Hz, 1H), 7.33 (t, J=7.3 Hz, 1H), 7.12 (t, J=8.1 Hz, 1H), 6.52 (s, 2H), 5.08 (dd, J=15.2, 6.22 Hz, 1H), 4.83-4.69 (m, 3H), 4.26 (br s, 1H), 3.78 (dd, J=14.6, 3.9 Hz, 1H), 3.61 (dd, J=14.4, 1.61 Hz, 1H), 2.67 (s, 3H), 0.51 (s, 9H), 0.00 (s, 3H), −0.19 (s, 3H);

MS (APCI) m/z 462.1 (M+H)$^+$;

Anal. Calcd for $C_{21}H_{31}N_5O_3SSi$: C, 54.63; H, 6.77; N, 15.17. Found: C, 54.50; H, 6.48; N, 14.99.

Example 2

6-Amino-9-(methylsulfonyl)-9,10,11,12-tetrahydro-8H-[1,4]diazepino[1',2':1,2]imidazo[4,5-c]quinolin-11-ol

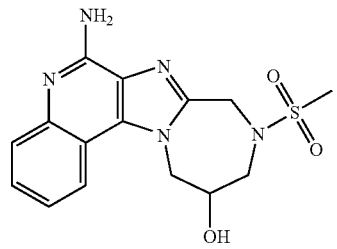

A suspension of 11-{[tert-butyl(dimethyl)silyl]oxy}-9-(methylsulfonyl)-9,10,11,12-tetrahydro-8H-[1,4]diazepino[1',2':1,2]imidazo[4,5-c]quinolin-6-amine (1.0 g, 2.2 mmol) in anhydrous THF (30 mL) was cooled to −20° C., and tetrabutylammonium fluoride (2.383 mL of a 1 M solution in THF) was slowly added. The reaction was stirred overnight, and a precipitate formed. The cold reaction mixture was filtered, and the isolated precipitate was washed with THF and dried under high vacuum to provide 313.7 mg of 6-amino-9-(methylsulfonyl)-9,10,11,12-tetrahydro-8H-[1,4]diazepino[1',2':1,2]imidazo[4,5-c]quinolin-11-ol as white crystals, mp 282-283° C.

¹H NMR (300 MHz), DMSO, δ 8.30 (d, J=8.1 Hz, 1H), 7.61 (d, J=8.2 Hz, 1H), 7.43 (t, J=7.6 Hz, 1H), 7.22 (t, J=8.0 Hz, 1H), 6.59 (s, 2H), 5.74 (s, 1H), 5.09 (dd, J=14.8, 6.7 Hz, 1H), 4.86-4.78 (m, 3H), 4.15 (s, 1H), 3.84-3.69 (m, 2H), 2.71 (s, 3H);

MS (APCI) m/z 348.1 (M+H)⁺;

Anal. Calcd for $C_{15}H_{17}N_5O_3S \cdot 0.4H_2O$: C, 50.81; H, 5.06; N, 19.75. Found: C, 51.02; H, 5.21; N, 19.58.

Example 3

10,10-Dimethyl-9-(methylsulfonyl)-8,9,10,11-tetrahydropyrazino[1',2':1,2]imidazo[4,5-c]quinolin-6-amine

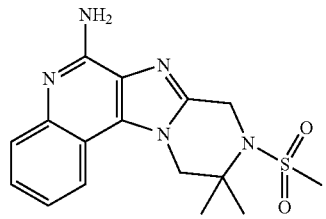

Part A

Under a nitrogen atmosphere, a solution of triethylamine (167 mL, 1.20 mol) in anhydrous dichloromethane (1 L) was cooled to 0° C. Solid 4-chloro-3-nitroquinoline (121.6 g, 585 mmol) was added over a period of five minutes, and the reaction was allowed to warm to ambient temperature slowly and stirred for two days. The solvent was removed under reduced pressure, and the resulting yellow solid was shaken with water (1 L) for several minutes and then isolated by filtration, washed with water (3×200 mL), and dried under vacuum for four days to provide 149 g of 2-methyl-N¹-(3-nitroquinolin-4-yl)propane-1,2-diamine as a bright yellow powder.

Anal. Calcd for $C_{13}H_{16}N_4O_2$: C, 59.53; H, 6.23; N, 21.36. Found: C, 59.23; H, 6.22; N, 21.45.

The product was dissolved in isopropanol (2×100 mL), concentrated under reduced pressure, dissolved in chloroform (2×100 mL), concentrated under reduced pressure, and finally dried under vacuum overnight.

Part B

Under a nitrogen atmosphere, a suspension of 2-methyl-N¹-(3-nitroquinolin-4-yl)propane-1,2-diamine (93 g, 358 mmol) and triethylamine (100 mL, 717 mmol) in anhydrous dichloromethane (1 L) was cooled to 0° C. Methanesulfonyl chloride (27.7 mL, 358 mmol) was added over a period of 20 minutes. The reaction was allowed to warm to ambient temperature and stirred overnight. Additional methanesulfonyl chloride (9.2 mL) was added over a period of five minutes, and the reaction was stirred for an additional day. Additional methanesulfonyl chloride (2.0 mL) was added, and the reaction was stirred for two hours. The solvent was removed under reduced pressure, and the residue was triturated with water (800 mL) at 50° C., isolated by filtration, and washed with water to provide 116 g of N-{1,1-dimethyl-2-[(3-nitroquinolin-4-yl)amino]ethyl}methanesulfonamide as a yellow powder.

Part C

A solution of N-{1,1-dimethyl-2-[(3-nitroquinolin-4-yl)amino]ethyl}methanesulfonamide (4.0 g, 12 mmol) in acetonitrile (200 mL) was added to a Parr vessel charged with 5% platinum on carbon (0.5 g) and purged with nitrogen. The vessel was placed under hydrogen pressure (50 psi, $3.4 \times 10^5$ Pa) and shaken overnight. The reaction was filtered through a layer of CELITE filter aid, and the filter cake was washed with acetonitrile and dichloromethane until the filtrate was colorless. The filtrate was concentrated under reduced pressure to provide 3.51 g of N-{2-[(3-aminoquinolin-4-yl)amino]-1,1-dimethylethyl}methanesulfonamide as a yellow powder.

Part D

Under a nitrogen atmosphere, a solution of N-{2-[(3-aminoquinolin-4-yl)amino]-1,1-dimethylethyl}methanesulfonamide (2.65 g, 8.59 mmol) in 1,2-dichloroethane (100 mL) was cooled to 0° C. Triethylamine (2.4 mL, 17 mmol) and chloroacetyl chloride (0.82 mL, 10.3 mmol) were sequentially added, and the reaction was allowed to warm to ambient temperature, stirred overnight, and then heated at reflux for 1.5 days. The reaction was washed with saturated aqueous sodium bicarbonate (2×100 mL) and brine (100 mL), dried over sodium sulfate, filtered, and concentrated under reduced pressure to provide 1.92 g of 10,10-dimethyl-9-(methylsulfonyl)-8,9,10,11-tetrahydropyrazino[4',3':1,2]imidazo[4,5-c]quinoline as a brown solid, which was used without purification.

Part E

In one portion mCPBA (0.87 g of 60% purity, 3.0 mmol) was added to a solution of 10,10-dimethyl-9-(methylsulfonyl)-8,9,10,11-tetrahydropyrazino[4',3':1,2]imidazo[4,5-c]quinoline (0.98 g, 3.0 mmol) in chloroform (50 mL), and the reaction was stirred for three hours at ambient temperature under a nitrogen atmosphere. The reaction mixture was washed with 1% aqueous sodium carbonate (50 mL), and the aqueous solution was extracted with chloroform (3×50 mL). The combined organic fractions were washed with brine, dried over sodium sulfate, filtered, and concentrated under reduced pressure to provide 0.91 g of 10,10-dimethyl-9-(methylsulfonyl)-5-oxido-8,9,10,11-tetrahydropyrazino[1',2':1,2]iridazo[4,5-c]quinoline as an orange solid.

Part F

Ammonium hydroxide (5 mL) was added with vigorous stirring to a suspension of 10,10-dimethyl-9-(methylsulfonyl)-5-oxido-8,9,10,11-tetrahydropyrazino[1',2':1,2]imidazo[4,5-c]quinoline (0.91 g, 2.6 mmol) in dichloromethane (25 mL). p-Toluenesulfonyl chloride (0.50 g, 2.6 mmol) was added in one portion, and the reaction was stirred for four hours at ambient temperature. The organic layer was separated and washed with 1% aqueous sodium carbonate (50 mL) and brine, dried over sodium sulfate, filtered, and concentrated under reduced pressure. The resulting orange solid (0.77 g) was recrystallized from 1,2-dichloroethane to provide 10,10-dimethyl-9-(methylsulfonyl)-8,9,10,11-tetrahydropyrazino[1',2':1,2]imidazo[4,5-c]quinolin-6-amine as a white powder, mp 227-228° C.

Anal. Calcd for $C_{16}H_{19}N_5O_2S$: C, 55.64; H, 5.54; N. 20.27. Found: C, 55.35; H, 5.61; N, 20.07.

Example 4 tert-Butyl 6-amino-10,11-dihydropyrazino[1',2':1,2]imidazo[4,5-c]quinoline-9(8H)-carboxylate

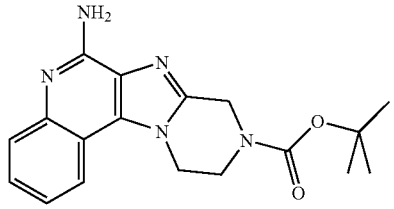

Part A

Triethylamine (58.2 g, 575 mmol) and 4-chloro-3-nitroquinoline (80.0 g, 384 mmol) were added to a solution of tert-butyl N-(2-aminoethyl)carbamate (67.6 g, 422 mmol) in DMF (300 mL), and the reaction was stirred overnight at ambient temperature. Water (600 mL) was added, and the resulting mixture was stirred for one hour. A precipitate formed and was isolated by filtration, washed with water (3×150 mL), and dried for two days in a vacuum oven at 45° C. to provide 125.36 g of tert-butyl 2-[(3-nitroquinolin-4-yl)amino]ethylcarbamate as a yellow solid.

Part B

A solution of tert-butyl 2-[(3-nitroquinolin-4-yl)amino]ethylcarbamate (20.0 g, 60.2 mmol) in a 2:1 mixture of dichloromethane:methanol (500 mL) was added to a Parr vessel. The system was purged with nitrogen, and 5% platinum on carbon (7.04 g, 36.1 mmol) was added. The vessel was placed under hydrogen pressure (50 psi, $3.4\times10^5$ Pa) and shaken overnight. The reaction mixture was filtered and concentrated under reduced pressure to provide 15.65 g of tert-butyl 2-[(3-aminoquinolin-4-yl)amino]ethylcarbamate.

Part C

A modification of the method described in Part E of Example 1 was used to treat tert-butyl 2-[(3-aminoquinolin-4-yl)amino]ethylcarbamate (15.65 g, 51.76 mmol) with triethylamine (10.82 mL, 77.64 mmol) followed by chloroacetyl chloride (4.5 mL, 57 mmol). The reaction was carried out in dichloromethane (60 mL). After the reaction mixture was filtered, the filtrate was washed with dilute aqueous sodium bicarbonate, dried over magnesium sulfate, and concentrated under reduced pressure to provide tert-butyl 2-[2-(chloromethyl)-1H-imidazo[4,5-c]quinolin-1-yl]ethylcarbamate as an amber-colored solid, which was combined with material from two other runs for use in the next step.

Part D

Under a nitrogen atmosphere, a solution of tert-butyl 2-[2-(chloromethyl)-1H-imidazo[4,5-c]quinolin-1-yl]ethylcarbamate (54.94 g, 152.3 mmol) in THF (400 mL) was cooled to 0° C.; a solution of potassium tert-butoxide (18.79 g of a 1 M solution in THF, 167.5 mmol) was added slowly. The reaction was stirred at 0° C. for three hours and then at ambient temperature overnight. The THF was removed under reduced pressure, and a 1:1 mixture of water and saturated aqueous sodium bicarbonate was added. The aqueous mixture was extracted with dichloromethane, and the combined extracts were washed sequentially with water and brine and concentrated under reduced pressure to provide 29.54 g of tert-butyl 10,11-dihydropyrazino[1',2':1,2]imidazo[4,5-c]quinoline-9(8H)-carboxylate.

Part E mCPBA (26.1 g of 77% pure material, 118 mmol) was added in small portions to a solution of tert-butyl 10,11-dihydropyrazino[1',2':1,2]imidazo[4,5-c]quinoline-9(8H)-carboxylate (29.54 g, 91.06 mmol) in chloroform (500 mL), and the reaction was stirred for one hour at ambient temperature. Aqueous sodium carbonate (400 mL of a 1% solution) was added, and the mixture was stirred for 30 minutes. The organic layer was separated, washed with 1% aqueous sodium carbonate (2×300 mL). Citric acid (10% aqueous solution) was added to aid in the separation. The organic layer was then washed twice with 10% aqueous citric acid, and the combined aqueous washings were extracted with chloroform (3×150 mL). The combined organic fractions were dried over magnesium sulfate, filtered, and concentrated under reduced pressure. The resulting solid was dried overnight under vacuum to provide 28.49 g of tert-butyl 5-oxido-10,11-dihydropyrazino[1',2':1,2]imidazo[4,5-c]quinoline-9(8H)-carboxylate as a brown solid.

Part F

Concentrated ammonium hydroxide (160 mL) was added with vigorous stirring to a solution of tert-butyl 5-oxido-10,11-dihydropyrazino[1',2':1,2]imidazo[4,5-c]quinoline-9(8H)-carboxylate (28.49 g, 83.7 mmol) in dichloromethane (300 mL). p-Toluenesulfonyl chloride (15.96 g, 83.7 mmol) was added in small portions over a period of five minutes, after which an analysis by HPLC indicated that the reaction was complete. The aqueous layer was then extracted with dichloromethane (3×150 mL), and the combined organic fractions were washed with 1% aqueous sodium carbonate (2×150 mL). The combined aqueous washings were extracted with dichloromethane (200 mL), and all organic fractions were combined, dried over magnesium sulfate, filtered, and concentrated under reduced pressure to provide tert-butyl 6-amino-10,11-dihydropyrazino[1',2':1,2]imidazo[4,5-c]quinoline-9(8H)-carboxylate as a yellow solid.

Material from another run was purified by column chromatography on silica gel (eluting with dichloromethane:methanol in a gradient from 99:1 to 85:15) to provide the product as a white powder, mp 207° C.

$^1$H NMR (300 MHz, CDCl$_3$) δ 7.88 (d, J=8.0 Hz, 1H), 7.80 (d, J=8.2 Hz, 1H), 7.49 (t, J=7.2 Hz, 1H), 7.27 (t, J=7.6 Hz, 1H), 5.51 (s, 2H), 4.92 (s, 2H), 4.53 (t, J=5.4 Hz, 2H), 4.03 (t, J=5.4 Hz, 2H), 1.53 (s, 9H);

MS (APCI) m/z 340 (M+H)$^+$;

Anal. Calcd for C$_{18}$H$_{21}$N$_5$O$_2$: C, 63.70; H, 6.24; N, 20.63. Found: C, 63.65; H, 6.51; N, 20.52.

Example 5

9-(Methylsulfonyl)-8,9,10,11-tetrahydropyrazino[1',2':1,2]imidazo[4,5-c]quinolin-6-amine trifluoroacetate

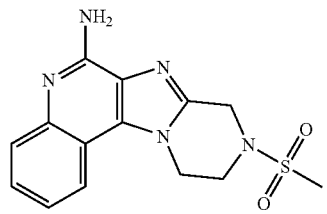

Part A

Hydrogen chloride (300 mL of a 4 N solution in 1,4-dioxane) was added to a solution of tert-butyl 6-amino-10,11-dihydropyrazino[1',2':1,2]imidazo[4,5-c]quinoline-9(8H)-carboxylate (34.74 g, 102.36 mmol) in dichloromethane (300 mL). The reaction was stirred overnight at ambient temperature and then concentrated under reduced pressure. The resulting solid was suspended in dichloromethane, isolated by filtration, and washed sequentially with dichloromethane, diethyl ether, hexane, and diethyl ether. The solid was then triturated with methanol and isolated by filtration to provide 11.58 g of 8,9,10,11-tetrahydropyrazino[1',2':1,2]imidazo[4,5-c]quinolin-6-amine hydrochloride as a white solid. The filtrate was concentrated under reduced pressure, dissolved in water, and precipitated with 1,4-dioxane to provide an additional 6.95 g of product.

Part B

Triethylamine (2.8 mL, 20.1 mmol) was added to a suspension of 8,9,10,11-tetrahydropyrazino[1',2':1,2]imidazo[4,5-c]quinolin-6-amine hydrochloride (1.85 g, 6.71 mmol) in DMF (20 mL). The mixture was sonicated for ten minutes at 80° C., and methanesulfonyl chloride (922 mg, 8.05 mmol) was slowly added. The mixture was stirred at ambient temperature overnight. After the solvent was removed under reduced pressure, the residue was combined with material from two other runs and ultimately purified by prep HPLC according to the method described above to provide 9-(methylsulfonyl)-8,9,10,11-tetrahydropyrazino[1',2':1,2]imidazo[4,5-c]quinolin-6-amine trifluoroacetate as white crystals, mp 242-243° C.

$^1$H NMR (300 MHz, DMSO-$d_6$) δ 9.06 (br s, 2H), 8.26 (d, J=8.13 Hz, 1H), 7.82 (d, J=8.31 Hz, 1H), 7.73 (t, J=7.21 Hz, 1H), 7.57 (t, J=7.21 Hz, 1H), 4.83 (t, J=5.37 Hz, 2H), 4.78 (s, 2H), 3.88 (t, J=5.36 Hz, 2H), 3.18 (s, 3H);

$^{13}$C NMR (75 MHz, DMSO-$d_6$) δ 149.6, 147.5, 135.2, 134.5, 130.0, 125.1, 124.8, 122.4, 119.0, 113.2, 46.1, 45.0, 42.5, 36.5;

HRMS: Calc for $C_{14}H_{15}N_5O_2$, theoretical mass 318.1025, measured mass 318.1015.

Example 6 tert-Butyl 6-amino-11,12-dihydro-8H-[1,4]diazepino[1',2':1,2]imidazo[4,5-c]quinoline-9(10H)-carboxylate

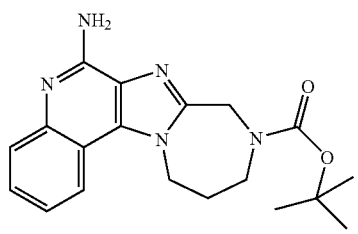

Part A

4-Chloro-3-nitroquinoline (54.42 g, 260.9 mmol) was added to a solution of tert-butyl N-(3-amninopropyl)carbamate (50.0 g, 287 mmol) in anhydrous DMF (300 mL), and the reaction was stirred overnight at ambient temperature. The product was isolated as described in Part A of Example 4 to provide 84.55 g of tert-butyl 3-[(3-nitroquinolin-4-yl)amino]propylcarbamate as a yellow solid.

Part B

A solution of tert-butyl 3-[(3-nitroquinolin-4-yl)amino]propylcarbamate (50.0 g, 144 mmol) in 1,2-dichloroethane (450 mL) and 5% platinum on carbon (16.9 g, 86.6 mmol) were added to a Parr vessel, which was placed under hydrogen pressure (30 psi, $2.1 \times 10^5$ Pa) and shaken until the reaction was complete. The reaction mixture was filtered and concentrated under reduced pressure. The residue was dissolved in ethyl acetate, and the resulting solution was filtered to remove an insoluble impurity, washed sequentially with brine (3×) and dilute aqueous sodium bicarbonate, dried over magnesium sulfate, filtered, and concentrated under reduced pressure to provide 42.52 g of tert-butyl 3-[(3-aminoquinolin-4-yl)amino]propylcarbamate.

Part C

Triethylamine (20.4 g, 202 mmol) was added to a solution of tert-butyl 3-[(3-aminoquinolin-4-yl)amino]propylcarbamate (42.52 g, 134.4 mmol) in dichloromethane (500 mnL). Chloroacetyl chloride (16.7 g, 148 mmol) was added dropwise, and the reaction was stirred overnight at ambient temperature. The reaction mixture was filtered to remove a solid; the filtrate was concentrated under reduced pressure and mixed with ethyl acetate. The resulting mixture was filtered to remove a solid, washed sequentially with brine (3×) and dilute aqueous sodium bicarbonate, concentrated under reduced pressure, and dried under high vacuum to provide 41.9 g of tert-butyl 3-[2-(chloromethyl)-1H-imidazo[4,5-c]quinolin-1-yl]propylcarbamate.

Part D

A modification of the method described in Part D of Example 4 was used to treat tert-butyl 3-[2-(chloromethyl)-1H-imidazo[4,5-c]quinolin-1-yl]propylcarbamate (36.76 g, 98.1 mmol) with potassium tert-butoxide (107.9 mL of a 1 M solution in THF). Following the work-up procedure, the product was mixed with ethyl acetate. The resulting mixture was filtered to remove a solid, and the filtrate was concentrated under reduced pressure to provide 30.0 g of tert-butyl 11,12-dihydro-8H-[1,4]diazepino[1',2':1,2]imidazo[4,5-c]quinoline-9(10H)-carboxylate.

Part E

The general method described in Part E of Example 4 was used to treat tert-butyl 11,12-dihydro-8H-[1,4]diazepino[1',2':1,2]imidazo[4,5-c]quinoline-9(10H)-carboxylate (30.0 g, 88.6 mmol) with mCPBA (23.8 g of 77% pure material, 138 mmol) to provide tert-butyl 5-oxido-11,12-dihydro-8H-[1,4]diazepino[1',2':1,2]imidazo[4,5-c]quinoline-9(10H)-carboxylate. The product was not dried over magnesium sulfate but was dried under high vacuum overnight.

Part F

The general method described in Part F of Example 4 was used to aminate the material from Part E with ammonium hydroxide (170 mL) and p-toluenesulfonyl chloride (16.92 g, 88.74 mmol) to provide 28.44 g of tert-butyl 6-amino-11,12-dihydro-8H-[1,4]diazepino[1',2':1,2]imidazo[4,5-c]quinoline-9(10H)-carboxylate.

Material from another run was purified by column chromatography on silica gel (eluting with dichloromethane:methanol in a gradient from 99:1 to 85:15) to provide the product as a white powder, mp 213° C.

$^1$H NMR (300 MHz, CDCl$_3$) δ 7.91 (d, J=8.1 Hz, 1H), 7.71 (d, J=8.3 Hz, 1H), 7.39 (t, J=7.8 Hz, 1H), 7.16 (t, J=7.3 Hz, 1H), 5.68 (s, 2H), 4.71 (s, 2H), 4.60 (t, J=5.2 Hz, 2H), 3.73-3.62 (m, 2H), 2.18-2.09 (m, 2H), 1.33 (s, 9H);

MS (APCI) m/z 354 (M+H)$^+$;

Anal. Calcd for C$_{19}$H$_{23}$N$_5$O$_2$: C, 64.57; H, 6.56; N, 19.82. Found: C, 64.29; H, 6.82; N, 19.54.

Example 7

9-(Methylsulfonyl)-9,10,11,12-tetrahydro-8H-[1,4]diazepino[1',2':1,2]imidazo[4,5-c]quinolin-6-amine trifluoroacetate

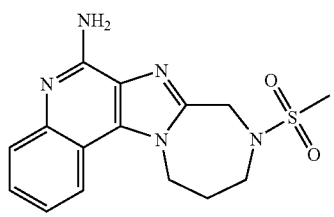

Part A

The general method described in Part A of Example 5 was used to deprotect tert-butyl 6-amino-11,12-dihydro-8H-[1,4]diazepino[1',2':1,2]imidazo[4,5-c]quinoline-9(10H)-carboxylate (28.44 g, 80.47 mmol). A precipitate was present at the end of the reaction and was isolated by filtration. The solid was dissolved in a small amount of water, precipitated with 1,4-dioxane, isolated by filtration, and dried for two days in a vacuum oven at 75° C. to provide 17.04 g of the 9,10,11,12-tetrahydro-8H-[1,4]diazepino[1',2':1,2]imidazo[4,5-c]quinolin-6-amine hydrochloride.

Part B

The general methods described in Part B of Example 5 were used to treat 9,10,11,12-tetrahydro-8H-[1,4]diazepino[1',2':1,2]imidazo[4,5-c]quinolin-6-amine hydrochloride with triethylamine and methanesulfonyl chloride and purify the final product to provide 9-(methylsulfonyl)-9,10,11,12-tetrahydro-8H-[1,4]diazepino[1',2':1,2]imidazo[4,5-c]quinolin-6-amine trifluoroacetate, which was isolated as white needles, mp 250-250.9° C.

Anal. Calcd for C$_{15}$H$_{17}$N$_5$O$_2$S.1.10C$_2$HF$_3$O$_2$.0.30H$_2$O: C, 44.69; H, 4.08; N, 15.15. Found: C, 45.05; H, 3.76; N, 15.22.

Example 8

9-(Methylsulfonyl)-9,10,11,12-tetrahydro-8H-[1,4]diazepino[1',2':1,2]imidazo[4,5-c]quinolin-6-amine

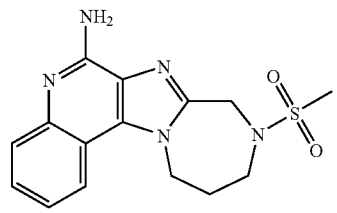

Part A

Potassium tert-butoxide (77.2 mL of a 1 M solution in THF) was added to a solution of tert-butyl 3-[2-(chloromethyl)-1H-imidazo[4,5-c]quinolin-1-yl]propylcarbamate (24.12 g, 64.34 mmol, prepared according to the methods described in Example 6 Parts A through C) in THF (250 mL), and the reaction was stirred overnight at ambient temperature. The solvent was removed under reduced pressure, and the residue was purified by column chromatography on silica gel (eluting with 2N ammonia in methanol/dichloromethane in a gradient from 0:100 to 15:85) to provide 9.1 g of tert-butyl 11,12-dihydro-8H-[1,4]diazepino[1',2':1,2]imidazo[4,5-c]quinoline-9(10H)-carboxylate.

Part B

Hydrogen chloride (100 mL of a 4 N solution in 1,4-dioxane) was added to a solution of tert-butyl 11,12-dihydro-8H-[1,4]diazepino[1',2':1,2]imidazo[4,5-c]quinoline-9(10H)-carboxylate (9.1 g, 27 mmol) in methanol (60 mL). The reaction was stirred overnight at ambient temperature and then diluted with diethyl ether. A precipitate was present and was isolated by filtration, washed sequentially with dichloromethane and diethyl ether, and dried under vacuum to provide 7.47 g of 9,10,11,12-tetrahydro-8H-[1,4]diazepino[1',2':1,2]imidazo[4,5-c]quinoline hydrochloride as a white solid.

Part C

Methanesulfonyl chloride (2.54 mL, 32.6 g) was added to a solution of 9,10,11,12-tetrahydro-8H-[1,4]diazepino[1',2':1,2]imidazo[4,5-c]quinoline hydrochloride (7.47 g, 27.2 mmol) and triethylamine (22.73 mL, 163.1 mmol) in DMF (50 mL). The reaction was stirred overnight at ambient temperature and then concentrated under reduced pressure to provide 3.065 g of 9-(methylsulfonyl)-9,10,11,12-tetrahydro-8H-[1,4]diazepino[1',2':1,2]imidazo[4,5-c]quinoline.

Part D mCPBA (2.55 g of 77%, 11.38 mmol) was added to a suspension of 9-(methylsulfonyl)-9,10,11,12-tetrahydro-8H-[1,4]diazepino[1',2':1,2]imidazo[4,5-c]quinoline (3.0 g, 9.5 mmol) in chloroform, and the reaction was stirred for 30 minutes at ambient temperature. The reaction was incomplete as determined by LC/MS analysis. Additional mCPBA (approximately 0.5 equivalent) was added twice, and the reaction was stirred overnight. The solvent was removed under reduced pressure, and a solution of potassium hydroxide in methanol was added to adjust to pH 7.5. The methanol was removed under reduced pressure, and residue was dissolved in chloroform. Additional mCPBA (1.2 equivalents) was added, and the reaction was stirred for two hours. Additional mCPBA was added, and the reaction was stirred overnight at ambient temperature. Ammonium hydroxide (15 mL) and p-toluenesulfonyl chloride (1.99 g, 10.4 mmol) were added, and the reaction was stirred at ambient temperature for two hours. The organic layer was separated, concentrated under reduced pressure, and purified by normal phase preparative HPLC on silica gel (eluting with 2 N ammonia in methanol/chloroform in a 42-minute gradient from 0:100 to 25:75). The resulting solid was recrystallized from 5:2:1 acetonitrile/ethanol/methanol to provide 9-(methylsulfonyl)-5-oxido-9,10,11,12-tetrahydro-8H-[1,4]diazepino[1',2':1,2]imidazo[4,5-c]quinoline, which was dissolved in chloroform, treated with ammonium hydroxide and p-toluenesulfonyl chloride, and purified by chromatography and recrystallization again as described above to provide 161 mg of 9-(methylsulfonyl)-9,10,11,12-tetrahydro-8H-[1,4]diazepino[1',2':1,2]imidazo[4,5-c]quinolin-6-amine as a white powder, mp 280° C.

$^1$H NMR (300 MHz, DMSO-d6) δ 8.27 (d, J=7.5 Hz, 1H), 7.62 (d, J=8.3 Hz, 1H), 7.44 (t, J=8.1 Hz, 1H), 7.23 (t, J=7.0 Hz, 1H), 6.63 (s, 2H), 4.91 (t, J=4.6 Hz, 2H), 4.82 (s, 2H), 3.73 (t, J=5.3 Hz, 2H), 2.79 (s, 3H), 2.25-2.16 (m, 2H);

MS (APCI) m/z 332 (M+H)$^+$;

Anal. Calcd for $C_{15}H_{17}N_5O_2S$: C, 54.37; H, 5.17; N, 21.13. Found: C, 54.13; H, 4.96; N, 21.00.

Examples 9-73

The aldehyde (0.125 mmol) indicated in the table below was added to a solution of 8,9,10,11-tetrahydropyrazino[1',2':1,2]imidazo[4,5-c]quinolin-6-amine hydrochloride (31.25 mg, 0.100 mmol) and N,N-diisopropylethylamine (0.035 mL, 0.20 mmol) in anhydrous DMF (2 mL) in a test tube. The test tube was capped and shaken for 15 minutes. Borane-pyridine complex (13 µL, 0.128 mmol) was added, and the reaction was shaken overnight. The solvent was removed by vacuum centrifugation. The compounds were purified by prep HPLC according to the method described above. The table below shows aldehyde used for each example, the structure of the resulting compound, and the observed accurate mass for the isolated trifluoroacetate salt.

Examples 9-73

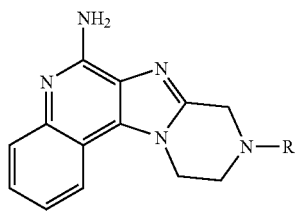

| Example | Aldehyde | R | Measured Mass (M + H) |
|---|---|---|---|
| 9 | Isovaleraldehyde | —CH$_2$CH(CH$_3$)$_2$ | 310.2028 |
| 10 | Furfural | —CH$_2$-(2-furyl) | 320.1519 |
| 11 | Tetrahydrofuran-3-carboxaldehyde | —CH$_2$-(tetrahydrofuran-2-yl) | 324.1843 |
| 12 | 3-(Methylthio)propionaldehyde | —CH$_2$CH$_2$CH$_2$SCH$_3$ | 328.1619 |
| 13 | Benzaldehyde | —CH$_2$Ph | 330.1751 |

-continued
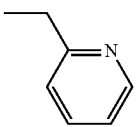
| Example | Aldehyde | R | Measured Mass (M + H) |
|---|---|---|---|
| 14 | 2-Pyridinecarboxaldehyde | 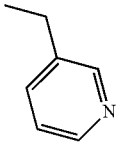 | 331.1684 |
| 15 | 3-Pyridinecarboxaldehyde | 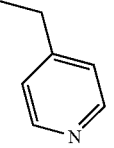 | 331.1691 |
| 16 | 4-Pyridinecarboxaldehyde | 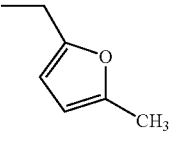 | 331.1670 |
| 17 | 5-Methylfurfural | 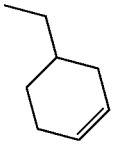 | 334.1698 |
| 18 | 1,2,3,6-Tetrahydrobenzaldehyde | 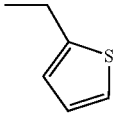 | 334.2045 |
| 19 | 2-Thiophenecarboxaldehyde | 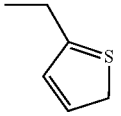 | 336.1305 |
| 20 | 3-Thiophenecarboxaldehyde | 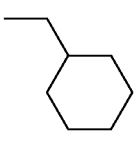 | 336.1279 |
| 21 | Cyclohexanecarboxaldehyde | 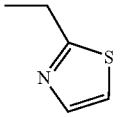 | 336.2178 |
| 22 | Thiazole-2-carboxaldehyde | | 337.1244 |

-continued
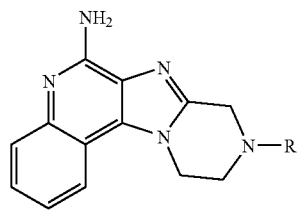
| Example | Aldehyde | R | Measured Mass (M + H) |
|---|---|---|---|
| 23 | m-Tolualdehyde | 3-methylbenzyl | 344.1898 |
| 24 | o-Tolualdehyde | 2-methylbenzyl | 344.1885 |
| 25 | p-Tolualdehyde | 4-methylbenzyl | 344.1895 |
| 26 | Phenylacetaldehyde | 2-phenylethyl | 344.1908 |
| 27 | 5-Norbornene-2-carboxaldehyde | norbornenylmethyl | 346.2049 |
| 28 | 2-Fluorobenzaldehyde | 2-fluorobenzyl | 348.1633 |
| 29 | 3-Fluorobenzaldehyde | 3-fluorobenzyl | 348.1656 |

-continued
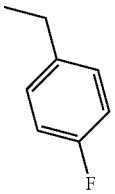
| Example | Aldehyde | R | Measured Mass (M + H) |
|---|---|---|---|
| 30 | 4-Fluorobenzaldehyde | 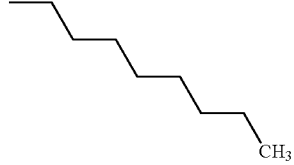 | 348.1638 |
| 31 | Octanal | 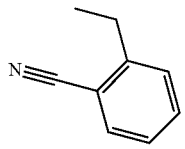 | 352.2493 |
| 32 | 2-Cyanobenzaldehyde | 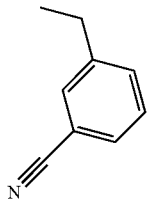 | 355.1696 |
| 33 | 3-Cyanobenzaldehyde | 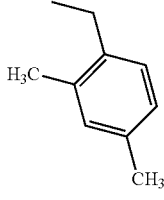 | 355.1700 |
| 34 | 2,4-Dimethylbenzaldehyde | 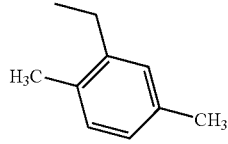 | 358.2039 |
| 35 | 2,5-Dimethylbenzaldehyde | 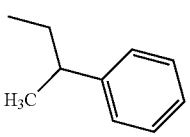 | 358.2057 |
| 36 | 2-Phenylpropionaldehyde |  | 358.2044 |

-continued
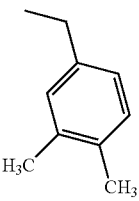
| Example | Aldehyde | R | Measured Mass (M + H) |
|---|---|---|---|
| 37 | 3,4-Dimethylbenzaldehyde | 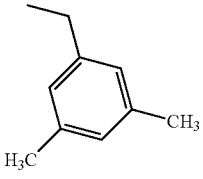 | 358.2041 |
| 38 | 3,5-Dimethylbenzaldehyde | 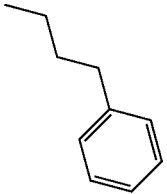 | 358.2042 |
| 39 | 3-Phenylpropionaldehyde | 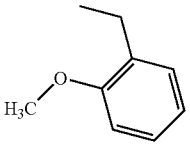 | 358.2040 |
| 40 | 2-Methoxybenzaldehyde | 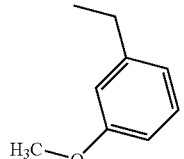 | 360.1855 |
| 41 | 3-Methoxybenzaldehyde | 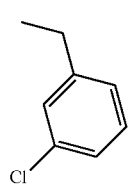 | 360.1830 |
| 42 | 3-Chlorobenzaldehyde | 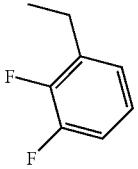 | 364.1318 |
| 43 | 2,3-Difluorobenzaldehyde | | 366.1544 |

-continued

| Example | Aldehyde | R | Measured Mass (M + H) |
|---|---|---|---|
| 44 | 2,4-Difluorobenzaldehyde | 2,4-difluorobenzyl | 366.1559 |
| 45 | 2,5-Difluorobenzaldehyde | 2,5-difluorobenzyl | 366.1544 |
| 46 | 2,6-Difluorobenzaldehyde | 2,6-difluorobenzyl | 366.1552 |
| 47 | 3,4-Difluorobenzaldehyde | 3,4-difluorobenzyl | 366.1526 |
| 48 | 3,5-Difluorobenzaldehyde | 3,5-difluorobenzyl | 366.1559 |
| 49 | 3-Phenylbutyraldehyde | 3-phenylbutyl | 372.2213 |
| 50 | Cuminaldehyde | 4-isopropylbenzyl | 372.2210 |

-continued
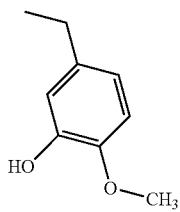
| Example | Aldehyde | R | Measured Mass (M + H) |
|---|---|---|---|
| 51 | 3-Hydroxy-4-methoxybenzaldehyde | 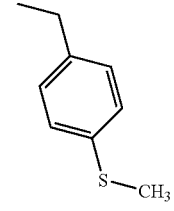 | 376.1783 |
| 52 | 4-(Methylthio)benzaldehyde | 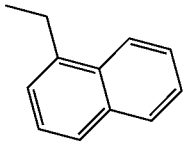 | 376.1618 |
| 53 | 1-Naphthaldehyde | 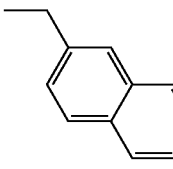 | 380.1891 |
| 54 | 2-Naphthaldehyde | 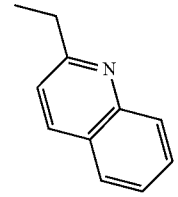 | 380.1910 |
| 55 | 2-Quinolinecarboxaldehyde | 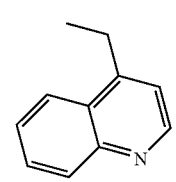 | 381.1857 |
| 56 | 4-Quinolinecarboxaldehyde | | 381.1861 |

-continued
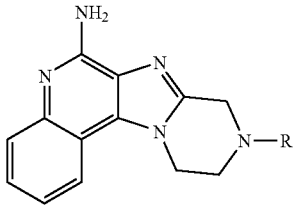
| Example | Aldehyde | R | Measured Mass (M + H) |
|---|---|---|---|
| 57 | Quinoline-3-carboxaldehyde | 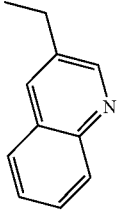 | 381.1850 |
| 58 | 3-Chloro-4-fluorobenzaldehyde | 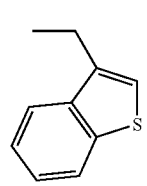 | 382.1216 |
| 59 | Thianaphthene-3-carboxaldehyde | 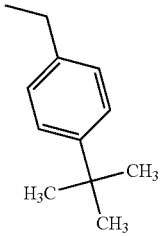 | 386.1435 |
| 60 | 4-tert-Butylbenzaldehyde | 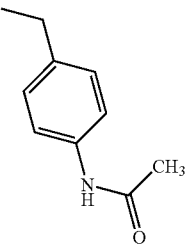 | 386.2370 |
| 61 | 4-Acetamidobenzaldehyde | 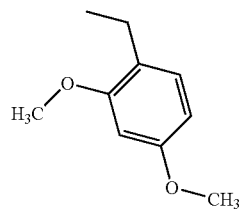 | 387.1960 |
| 62 | 2,4-Dimethoxybenzaldehyde | | 390.1944 |

-continued
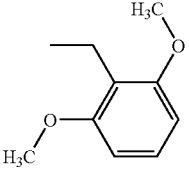
| Example | Aldehyde | R | Measured Mass (M + H) |
|---|---|---|---|
| 63 | 2,6-Dimethoxybenzaldehyde | 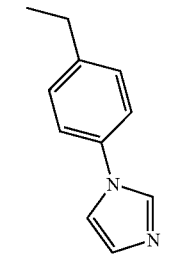 | 390.1940 |
| 64 | 4-(1H-Imidazol-1-yl)benzaldehyde | 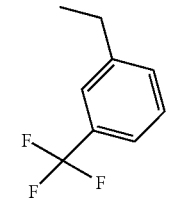 | 396.1953 |
| 65 | 3-(Trifluoromethyl)benzaldehyde | 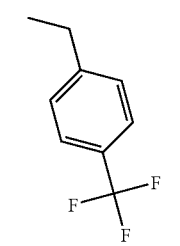 | 398.1613 |
| 66 | 4-(Trifluoromethyl)benzaldehyde | 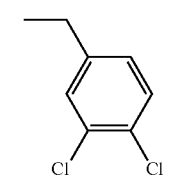 | 398.1630 |
| 67 | 3,4-Dichlorobenzaldehyde | 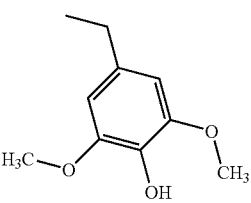 | 398.0961 |
| 68 | Syringaldehyde | | 406.1916 |

-continued

| Example | Aldehyde | R | Measured Mass (M + H) |
|---|---|---|---|
| 69 | 4-Biphenylcarboxaldehyde | (4-biphenyl)methyl | 406.2052 |
| 70 | 4-(2-Pyridyl)benzaldehyde | [4-(2-pyridyl)phenyl]methyl | 407.1984 |
| 71 | 3-Bromobenzaldehyde | (3-bromophenyl)methyl | 408.0809 |
| 72 | Diphenylacetaldehyde | 2,2-diphenylethyl | 420.2213 |
| 73 | 3-Benzyloxybenzaldehyde | (3-benzyloxyphenyl)methyl | 436.2172 |

Examples 74-113

The reagent (0.11 mmol) indicated in the table below was added to a solution of 8,9,10,11-tetrahydropyrazino[1',2':1,2]imidazo[4,5-c]quinolin-6-amine hydrochloride (24 mg, 0.077 mmol) and N,N-diisopropylethylamine (0.070 mL, 0.40 mmol) in anhydrous DMF (2 mL) in a test tube. The test tube was capped and shaken overnight. One drop of deionized water was added to each test tube, and the solvent was removed by vacuum centrifugation. The compounds were purified by prep HPLC using the method described above. The table below shows the acid chloride, sulfonyl chloride, isocyanate, or carbamoyl chloride used for each example, the structure of the resulting compound, and the observed accurate mass for the isolated trifluoroacetate salt.

Examples 74-113
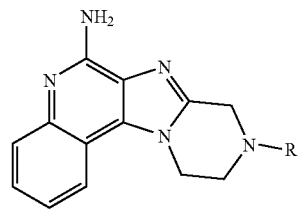
| Example | Reagent | R | Measured Mass (M + H) |
|---|---|---|---|
| 74 | Isobutyryl chloride | -C(=O)-CH(CH3)2 | 310.1672 |
| 75 | Isovaleryl chloride | -C(=O)-CH2-CH(CH3)2 | 324.1825 |
| 76 | Pentanoyl chloride | -C(=O)-CH2CH2CH2CH3 | 324.1813 |
| 77 | Phenylacetyl chloride | -C(=O)-CH2-Ph | 358.1682 |
| 78 | Thiophene-2-acetyl chloride | -C(=O)-CH2-(2-thienyl) | 364.2162 |
| 79 | Cinnamoyl chloride | -C(=O)-CH=CH-Ph | 370.1676 |
| 80 | Hydrocinnamoyl chloride | -C(=O)-CH2CH2-Ph | 372.1840 |

-continued

| Example | Reagent | R | Measured Mass (M + H) |
|---------|---------|---|----------------------|
| 81 | 2-Naphthoyl chloride | 2-naphthyl-C(=O)- | 394.1695 |
| 82 | 2,6-Dichlorobenzoyl chloride | 2,6-dichlorophenyl-C(=O)- | 412.0770 |
| 83 | 3,4-Dichlorobenzoyl chloride | 3,4-dichlorophenyl-C(=O)- | 412.0736 |
| 84 | m-Toluenesulfonyl chloride | 3-methylphenyl-S(=O)$_2$- | 394.1346 |
| 85 | 4-Cyanobenzenesulfonyl chloride | 4-cyanophenyl-S(=O)$_2$- | 405.1173 |
| 86 | 2-Chlorobenzenesulfonyl chloride | 2-chlorophenyl-S(=O)$_2$- | 414.0786 |
| 87 | 8-Quinolinesulfonyl chloride | 8-quinolinyl-S(=O)$_2$- | 431.1279 |

-continued
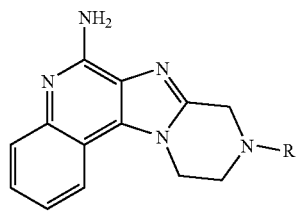
| Example | Reagent | R | Measured Mass (M + H) |
|---|---|---|---|
| 88 | 2-(Trifluoromethyl)benzenesulfonyl chloride | | 448.1073 |
| 89 | (−)-Camphor-10-sulfonyl chloride | | 454.1919 |
| 90 | D-(+)-10-Camphorsulfonyl chloride | | 454.1917 |
| 91 | 4-(Trifluoromethoxy)benzenesulfonyl chloride | | 464.1021 |
| 92 | Isopropyl isocyanate | | 325.1791 |
| 93 | n-Propyl isocyanate | | 325.1802 |
| 94 | tert-Butyl isocyanate | | 339.1955 |

-continued
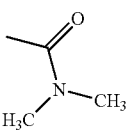
| Example | Reagent | R | Measured Mass (M + H) |
|---|---|---|---|
| 95 | Dimethylcarbamoyl chloride | 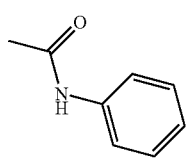 | 311.1600 |
| 96 | Phenyl isocyanate | 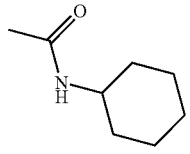 | 359.1635 |
| 97 | Cyclohexane isocyanate |  | 365.2094 |
| 98 | m-Tolyl isocyanate | 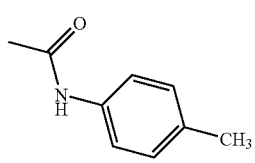 | 373.1790 |
| 99 | p-Tolyl isocyanate | 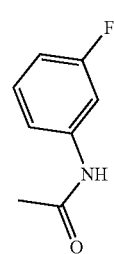 | 373.1812 |
| 100 | 3-Fluorophenyl isocyanate | 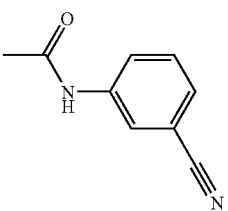 | 377.1559 |
| 101 | 3-Cyanophenyl isocyanate |  | 384.1573 |

-continued

| Example | Reagent | R | Measured Mass (M + H) |
|---------|---------|---|----------------------|
| 102 | 4-Cyanophenyl isocyanate | -C(O)NH-C6H4-CN (para) | 384.1605 |
| 103 | Benzoyl isocyanate | -C(O)NH-C(O)-C6H5 | 387.1575 |
| 104 | 1-Piperidinecarbonyl chloride | -C(O)-N(piperidine) | 351.1909 |
| 105 | 3-Methoxyphenyl isocyanate | -C(O)NH-C6H4-OCH3 (meta) | 389.1732 |
| 106 | 4-Methoxyphenyl isocyanate | -C(O)NH-C6H4-OCH3 (para) | 389.1761 |
| 107 | 4-Chlorophenyl isocyanate | -C(O)NH-C6H4-Cl (para) | 393.1261 |

-continued

| Example | Reagent | R | Measured Mass (M + H) |
|---|---|---|---|
| 108 | 3-Acetylphenyl isocyanate | 3-acetylphenyl-NH-C(O)- | 401.1763 |
| 109 | 4-(Dimethylamino)phenyl isocyanate | 4-(dimethylamino)phenyl-NH-C(O)- | 402.2050 |
| 110 | N-Methyl-N-phenylcarbamoyl chloride | N-methyl-N-phenyl-C(O)- | 373.1764 |
| 111 | Methyl 3-isocyanatobenzoate | 3-(methoxycarbonyl)phenyl-NH-C(O)- | 417.1692 |
| 112 | 2-(Trifluoromethyl)phenyl isocyanate | 2-(trifluoromethyl)phenyl-NH-C(O)- | 427.1511 |

-continued

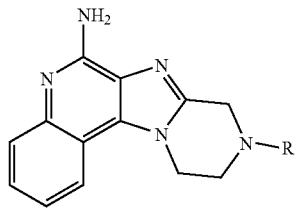

| Example | Reagent | R | Measured Mass (M + H) |
|---|---|---|---|
| 113 | 3-(Trifluoromethyl)phenyl isocyanate | *3-(trifluoromethyl)phenyl-NH-C(O)-* | 427.1479 |

Examples 114-188

The general method described in Examples 8-73 was used to treat 9,10,11,12-tetrahydro-8H-[1,4]diazepino[1',2':1,2]imidazo[4,5-c]quinolin-6-amine hydrochloride (32.2 mg, 0.099 mmol) with the aldehyde (0.125 mmol) indicated in the table below. The compounds were purified by prep HPLC using the method described above. The table below shows the aldehyde used for each example, the structure of the resulting compound, and the observed accurate mass for the isolated trifluoroacetate salt.

Examples 114-188

| Example | Aldehyde | R | Measured Mass (M + H) |
|---|---|---|---|
| 114 | Isovaleraldehyde | *-CH2-CH(CH3)-CH2-CH3 (isopentyl)* | 324.2216 |
| 115 | 3-Furaldehyde | *-CH2-(3-furyl)* | 334.1687 |
| 116 | Furfural | *-CH2-(2-furyl)* | 334.1680 |
| 117 | Tetrahydrofuran-3-carboxaldehyde | *-CH2-(tetrahydrofuran-2-yl)* | 338.2001 |

-continued
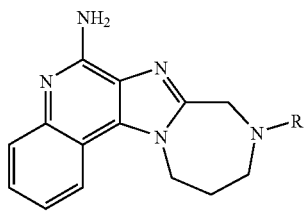
| Example | Aldehyde | R | Measured Mass (M + H) |
|---|---|---|---|
| 118 | 3-(Methylthio)propionaldehyde | | 342.1762 |
| 119 | 5-Methylfurfural | | 348.1849 |
| 120 | 1-Methyl-2-imidazolecaboxaldehyde | | 348.1934 |
| 121 | 1,2,3,6-Tetrahydrobenzaldehyde | | 348.2169 |
| 122 | 2-Thiophenecarboxaldehyde | | 350.1443 |
| 123 | Cyclohexanecarboxaldehyde | | 350.2365 |
| 124 | Thiazole-2-carboxaldehyde | | 351.1413 |
| 125 | m-Tolualdehyde | | 358.2049 |
| 126 | o-Tolualdehyde | | 358.2057 |
| 127 | p-Tolualdehyde | | 358.2039 |

-continued
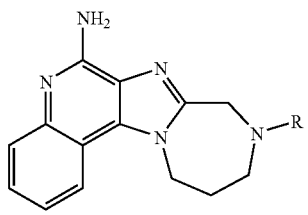
| Example | Aldehyde | R | Measured Mass (M + H) |
|---|---|---|---|
| 128 | Phenylacetaldehyde | | 358.2029 |
| 129 | 5-Norbornene-2-carboxaldehyde | | 360.2199 |
| 130 | 2-Fluorobenzaldehyde | | 362.1790 |
| 131 | 3-Fluorobenzaldehyde | | 362.1784 |
| 132 | 4-Fluorobenzaldehyde | | 362.1775 |
| 133 | Octanal | | 366.2640 |
| 134 | 2-Cyanobenzaldehyde | | 369.1852 |
| 135 | 2,4-Dimethylbenzaldehyde | | 372.2216 |
| 136 | 2,5-Dimethylbenzaldehyde | | 372.2185 |

-continued
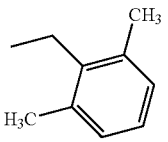
| Example | Aldehyde | R | Measured Mass (M + H) |
|---|---|---|---|
| 137 | 2,6-Dimethylbenzaldehyde | 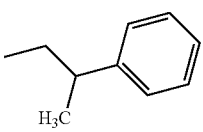 | 372.2202 |
| 138 | 2-Phenylpropionaldehyde | 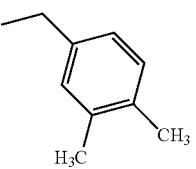 | 372.2208 |
| 139 | 3,4-Dimethylbenzaldehyde | 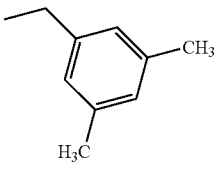 | 372.2206 |
| 140 | 3,5-Dimethylbenzaldehyde | 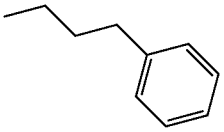 | 372.2205 |
| 141 | 3-Phenylpropionaldehyde | 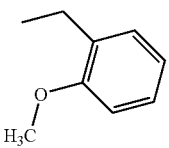 | 372.2208 |
| 142 | 2-Methoxybenzaldehyde | 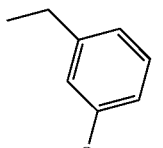 | 374.1985 |
| 143 | 3-Methoxybenzaldehyde | 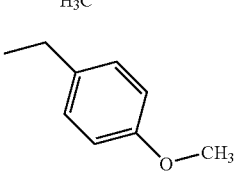 | 374.2007 |
| 144 | p-Anisaldehyde | | 374.1991 |

-continued

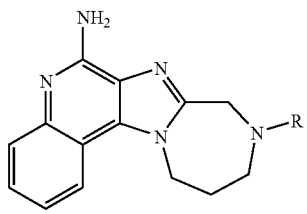

| Example | Aldehyde | R | Measured Mass (M + H) |
|---|---|---|---|
| 145 | 2-Chlorobenzaldehyde | 2-chlorobenzyl | 378.1490 |
| 146 | 3-Chlorobenzaldehyde | 3-chlorobenzyl | 378.1509 |
| 147 | 4-Chlorobenzaldehyde | 4-chlorobenzyl | 378.1519 |
| 148 | 2,3-Difluorobenzaldehyde | 2,3-difluorobenzyl | 380.1683 |
| 149 | 2,4-Difluorobenzaldehyde | 2,4-difluorobenzyl | 380.1696 |
| 150 | 2,5-Difluorobenzaldehyde | 2,5-difluorobenzyl | 380.1691 |
| 151 | 2,6-Difluorobenzaldehyde | 2,6-difluorobenzyl | 380.1713 |
| 152 | 3,4-Difluorobenzaldehyde | 3,4-difluorobenzyl | 380.1695 |

-continued
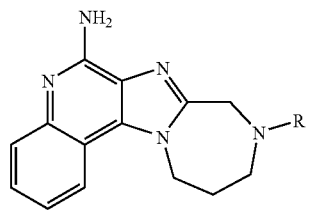
| Example | Aldehyde | R | Measured Mass (M + H) |
|---|---|---|---|
| 153 | 3,5-Difluorobenzaldehyde | 3,5-difluorobenzyl | 380.1693 |
| 154 | 3-Phenylbutyraldehyde | 3-phenylbutyl | 386.2366 |
| 155 | Cuminaldehyde | 4-isopropylbenzyl | 386.2386 |
| 156 | 2-(Methylthio)benzaldehyde | 2-(methylthio)benzyl | 390.1791 |
| 157 | 4-(Methylthio)benzaldehyde | 4-(methylthio)benzyl | 390.1776 |
| 158 | 1-Naphthaldehyde | 1-naphthylmethyl | 394.2055 |
| 159 | 2-Naphthaldehyde | 2-naphthylmethyl | 394.2041 |

-continued
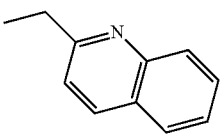
| Example | Aldehyde | R | Measured Mass (M + H) |
|---|---|---|---|
| 160 | 2-Quinolinecarboxaldehyde | 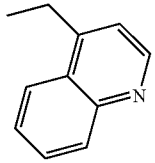 | 395.2013 |
| 161 | 4-Quinolinecarboxaldehyde | 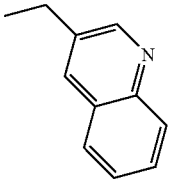 | 395.2016 |
| 162 | Quinoline-3-carboxaldehyde |  | 395.2010 |
| 163 | 2-Chloro-6-fluorobenzaldehyde | 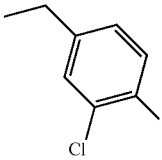 | 396.1422 |
| 164 | 3-Chloro-4-fluorobenzaldehyde | 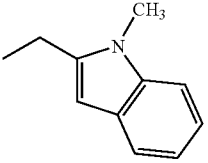 | 396.1386 |
| 165 | 1-Methylindole-2-carboxaldehyde | 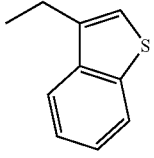 | 397.2133 |
| 166 | Thianaphthene-3-carboxaldehyde |  | 400.1615 |

-continued
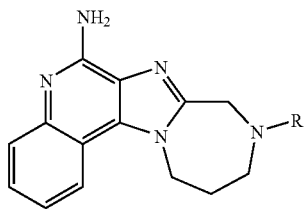
| Example | Aldehyde | R | Measured Mass (M + H) |
|---|---|---|---|
| 167 | 4-tert-Butylbenzaldehyde | | 400.2468 |
| 168 | Methyl 4-formylbenzoate | | 402.1954 |
| 169 | 2,5-Dimethoxybenzaldehyde | | 404.2111 |
| 170 | 2,6-Dimethoxybenzaldehyde | | 404.2102 |
| 171 | 3,4-Dimethoxybenzaldehyde | | 404.2094 |
| 172 | 3,5-Dimethoxybenzaldehyde | | 404.2091 |
| 173 | 4-(1H-Imidazol-1-yl)benzaldehyde | | 410.2101 |

-continued
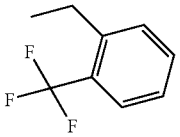
| Example | Aldehyde | R | Measured Mass (M + H) |
|---|---|---|---|
| 174 | 2-(Trifluoromethyl)benzaldehyde | 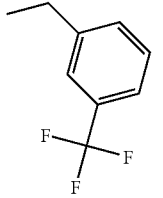 | 412.1722 |
| 175 | 3-(Trifluoromethyl)benzaldehyde | 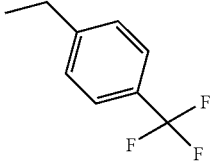 | 412.1757 |
| 176 | 4-(Trifluoromethyl)benzaldehyde | 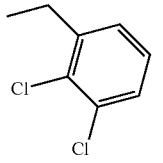 | 412.1757 |
| 177 | 2,3-Dichlorobenzaldehyde | 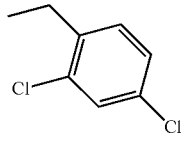 | 412.1117 |
| 178 | 2,4-Dichlorobenzaldehyde | 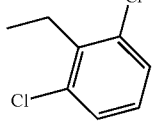 | 412.1100 |
| 179 | 2,6-Dichlorobenzaldehyde | 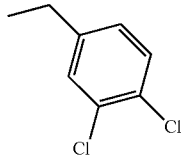 | 412.1117 |
| 180 | 3,4-Dichlorobenzaldehyde | | 412.1131 |

-continued
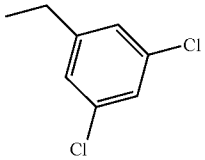
| Example | Aldehyde | R | Measured Mass (M + H) |
|---|---|---|---|
| 181 | 3,5-Dichlorobenzaldehyde | 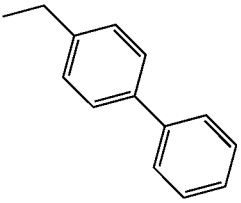 | 412.1116 |
| 182 | 4-Biphenylcarboxaldehyde | 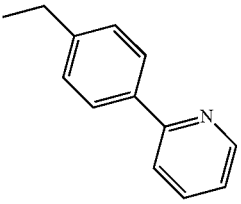 | 420.2209 |
| 183 | 4-(2-Pyridyl)benzaldehyde | 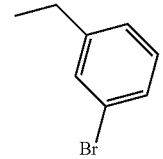 | 421.2167 |
| 184 | 3-Bromobenzaldehyde | 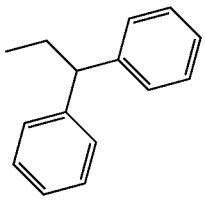 | 422.0999 |
| 185 | Diphenylacetaldehyde | 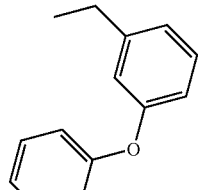 | 434.2369 |
| 186 | 3-Phenoxybenzaldehyde | | 436.2137 |

-continued

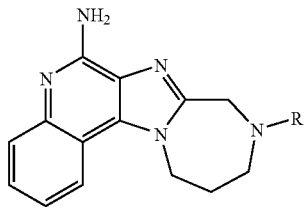

| Example | Aldehyde | R | Measured Mass (M + H) |
|---|---|---|---|
| 187 | 4-Phenoxybenzaldehyde | *(ethyl-phenyl-O-phenyl)* | 436.2163 |
| 188 | 3-Benzyloxybenzaldehyde | *(ethyl-phenyl-O-benzyl)* | 450.2297 |

Example 189-329

The general method described in Examples 74-113 was used to treat 9,10,11,12-tetrahydro-8H-[1,4]diazepino[1',2': 1,2]imidazo[4,5-c]quinolin-6-amine hydrochloride (32.5 mg, 0.100 mmol) with NN-diisopropylethylamine (0.0525 mL, 0.30 mmol) and the reagent (0.108 mmol) indicated in the table below. The compounds were purified by prep HPLC using the method described above. The table below shows the acid chloride, sulfonyl chloride, isocyanate, carbamoyl chloride, or sulfamoyl chloride used for each example, the structure of the resulting compound, and the observed accurate mass for the isolated trifluoroacetate salt.

Examples 189-329

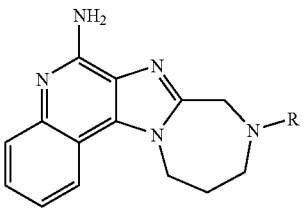

| Example | Reagent | R | Measured Mass (M + H) |
|---|---|---|---|
| 189 | Cyclopropanecarbonyl chloride | *(C(=O)-cyclopropyl)* | 322.1653 |

-continued
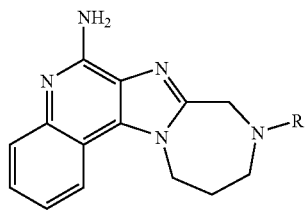
| Example | Reagent | R | Measured Mass (M + H) |
|---|---|---|---|
| 190 | Isobutyryl chloride | | 324.1812 |
| 191 | Methoxyacetyl chloride | | 326.1616 |
| 192 | Isovaleryl chloride | | 338.1970 |
| 193 | Pentanoyl chloride | | 338.1986 |
| 194 | Methyl oxalyl chloride | | 340.1394 |
| 195 | Isoxazole-5-carbonyl chloride | | 349.1419 |
| 196 | Cyclopentanecarbonyl chloride | | 350.1971 |
| 197 | tert-Butylacetyl chloride | | 352.2117 |

-continued

[Structure: tricyclic core with NH2 group and N-R substituent on diazepane ring fused to imidazole-quinoline]

| Example | Reagent | R | Measured Mass (M + H) |
|---------|---------|---|------------------------|
| 198 | Acetoxyacetyl chloride | –C(O)CH₂OC(O)CH₃ | 354.1550 |
| 199 | Methyl malonyl chloride | –C(O)CH₂C(O)OCH₃ | 354.1555 |
| 200 | 3-Methylthiopropionyl chloride | –C(O)CH₂CH₂SCH₃ | 356.1541 |
| 201 | Benzoyl chloride | –C(O)C₆H₅ | 358.1659 |
| 202 | Thiophene-2-carbonyl chloride | –C(O)-(2-thienyl) | 364.1246 |
| 203 | Cyclohexanecarbonyl chloride | –C(O)-cyclohexyl | 364.2122 |
| 204 | m-Toluoyl chloride | –C(O)-(3-methylphenyl) | 372.1835 |
| 205 | Phenylacetyl chloride | –C(O)CH₂C₆H₅ | 372.1830 |

-continued
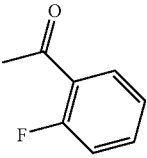
| Example | Reagent | R | Measured Mass (M + H) |
|---|---|---|---|
| 206 | 2-Fluorobenzoyl chloride | 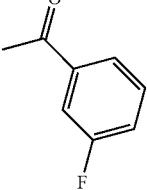 | 376.1570 |
| 207 | 3-Fluorobenzoyl chloride | 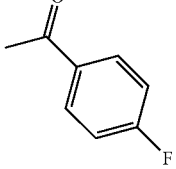 | 376.1579 |
| 208 | 4-Fluorobenzoyl chloride | 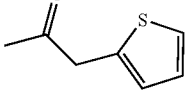 | 376.1573 |
| 209 | 2-Thiopheneacetyl chloride | 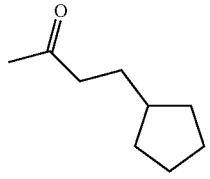 | 378.1382 |
| 210 | 3-Cyclopentylpropionyl chloride | 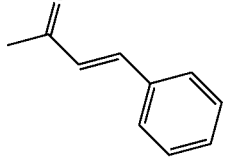 | 378.2298 |
| 211 | Cinnamoyl chloride | 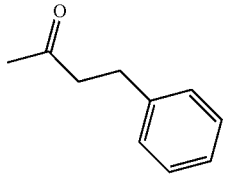 | 384.1814 |
| 212 | Hydrocinnamoyl chloride |  | 386.1988 |

-continued
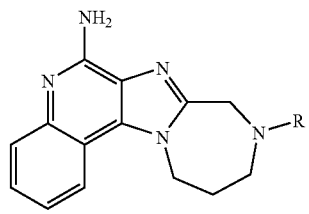
| Example | Reagent | R | Measured Mass (M + H) |
|---|---|---|---|
| 213 | Benzyl chloroformate | ![benzyl carbamate R group] | 388.1793 |
| 214 | m-Anisoyl chloride | ![m-methoxybenzoyl R group] | 388.1752 |
| 215 | p-Anisoyl chloride | ![p-methoxybenzoyl R group] | 388.1808 |
| 216 | 2-Chlorobenzoyl chloride | ![2-chlorobenzoyl R group] | 392.1268 |
| 217 | 3-Chlorobenzoyl chloride | ![3-chlorobenzoyl R group] | 392.1276 |
| 218 | 4-Chlorobenzoyl chloride | ![4-chlorobenzoyl R group] | 392.1291 |

-continued
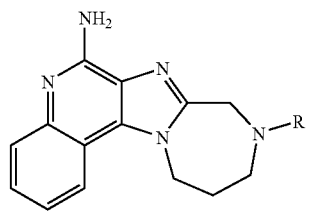
| Example | Reagent | R | Measured Mass (M + H) |
|---|---|---|---|
| 219 | 5-Nitro-2-furoyl chloride | | 393.1317 |
| 220 | 6-Chloronicotinyl chloride | | 393.1237 |
| 221 | 2,5-Difluorobenzoyl chloride | | 394.1472 |
| 222 | 2,6-Difluorobenzoyl chloride | | 394.1468 |
| 223 | Isonicotinoyl chloride hydrochloride | | 359.1619 |
| 224 | Nicotinoyl chloride hydrochloride | | 359.1613 |
| 225 | Methyl adipoyl chloride | | 396.2035 |

-continued
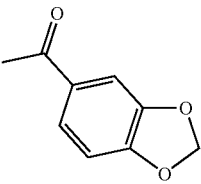
| Example | Reagent | R | Measured Mass (M + H) |
|---|---|---|---|
| 226 | 3,4-Methylenedioxybenzoyl chloride | 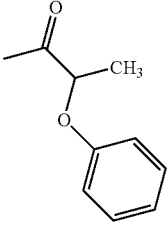 | 402.1560 |
| 227 | 2-Phenoxypropionyl chloride | 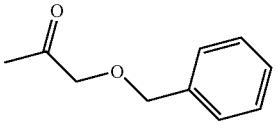 | 402.1921 |
| 228 | Benzyloxyacetyl chloride | 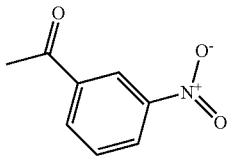 | 402.1928 |
| 229 | 3-Nitrobenzoyl chloride | 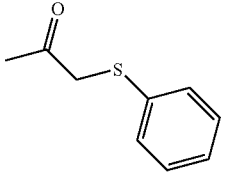 | 403.1527 |
| 230 | (Phenylthio)acetyl chloride | 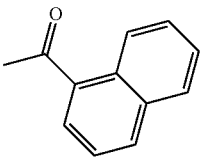 | 404.1550 |
| 231 | 1-Naphthoyl chloride | 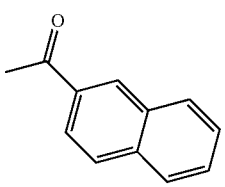 | 408.1833 |
| 232 | 2-Naphthoyl chloride | | 408.1820 |

-continued
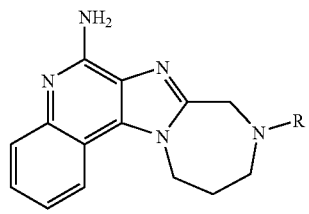
| Example | Reagent | R | Measured Mass (M + H) |
|---|---|---|---|
| 233 | 4-tert-Butylbenzoyl | ![] | 414.2271 |
| 234 | Methyl 4-chlorocarbonyl benzoate | ![] | 416.1727 |
| 235 | 4-Phenoxybutyryl chloride | ![] | 416.2069 |
| 236 | 3,5-Dimethoxybenzoyl chloride | ![] | 418.1880 |
| 237 | 4-Chlorophenoxyacetyl chloride | ![] | 422.1409 |

-continued
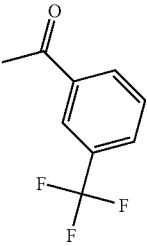
| Example | Reagent | R | Measured Mass (M + H) |
|---|---|---|---|
| 238 | 3-(Trifluoromethyl)benzoyl chloride | 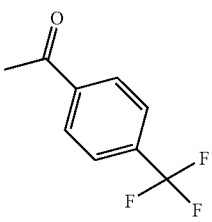 | 426.1581 |
| 239 | 4-(Trifluoromethyl)benzoyl chloride | 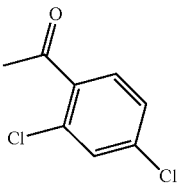 | 426.1558 |
| 240 | 2,4-Dichlorobenozyl chloride | 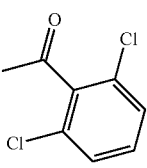 | 426.0907 |
| 241 | 2,6-Dichlorobenzoyl chloride | 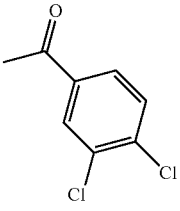 | 426.0891 |
| 242 | 3,4-Dichlorobenzoylchloride | 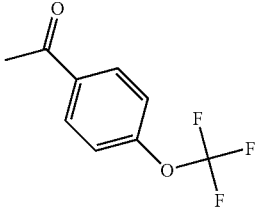 | 426.0871 |
| 243 | 4-(Trifluoromethoxy)benzoyl chloride |  | 442.1489 |

-continued

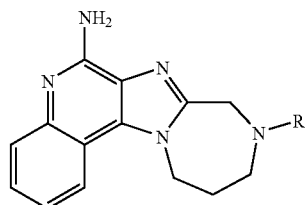

| Example | Reagent | R | Measured Mass (M + H) |
|---|---|---|---|
| 244 | 3,4,5-Trimethoxybenzoyl chloride | 3,4,5-trimethoxybenzoyl group | 448.2001 |
| 245 | 2,4,6-Trichlorobenzoyl chloride | 2,4,6-trichlorobenzoyl group | 460.0494 |
| 246 | Methanesulfonyl chloride | —S(O)₂—CH₃ | 332.1168 |
| 247 | Ethanesulfonyl chloride | —S(O)₂—CH₂CH₃ | 346.1333 |
| 248 | 1-Propanesulfonyl chloride | —S(O)₂—CH₂CH₂CH₃ | 360.1497 |
| 249 | Isopropylsulfonyl chloride | —S(O)₂—CH(CH₃)₂ | 360.1490 |
| 250 | Dimethylsulfamoyl chloride | —S(O)₂—N(CH₃)₂ | 361.1455 |
| 251 | 1-Butanesulfonyl chloride | —S(O)₂—CH₂CH₂CH₂CH₃ | 374.1654 |

-continued
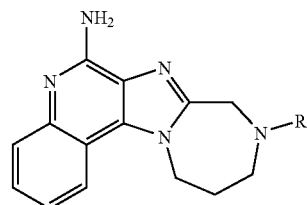
| Example | Reagent | R | Measured Mass (M + H) |
|---|---|---|---|
| 252 | Benzenesulfonyl chloride | | 394.1320 |
| 253 | 2-Thiosulfonyl chloride | | 400.0913 |
| 254 | α-Toluenesulfonyl chloride | | 408.1497 |
| 255 | m-Toluenesulfonyl chloride | | 408.1502 |
| 256 | 2-Fluorobenzenesulfonyl chloride | | 412.1233 |
| 257 | 3-Fluorobenzenesulfonyl chloride | | 412.1238 |
| 258 | 3,5-Dimethylisoxazole-4-sulfonyl chloride | | 413.1385 |
| 259 | 2-Cyanobenzenesulfonyl chloride | | 419.1289 |

-continued

| Example | Reagent | R | Measured Mass (M + H) |
|---|---|---|---|
| 260 | 3-Cyanobenzenesulfonyl chloride | 3-cyanophenylsulfonyl | 419.1307 |
| 261 | 4-Cyanobenzenesulfonyl chloride | 4-cyanophenylsulfonyl | 419.1302 |
| 262 | β-Styrenesulfonyl chloride | β-styrenylsulfonyl | 420.1479 |
| 263 | p-Styrenesulfonyl chloride | p-styrenylsulfonyl | 420.1496 |
| 264 | 4-Methoxybenzenesulfonyl chloride | 4-methoxyphenylsulfonyl | 424.1448 |
| 265 | 3-Chlorobenzenesulfonyl chloride | 3-chlorophenylsulfonyl | 428.0941 |
| 266 | 4-Chlorobenzenesulfonyl chloride | 4-chlorophenylsulfonyl | 428.0944 |
| 267 | 2,4-Difluorobenzenesulfonyl chloride | 2,4-difluorophenylsulfonyl | 430.1145 |

-continued
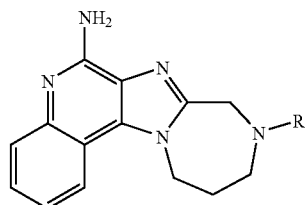
| Example | Reagent | R | Measured Mass (M + H) |
|---|---|---|---|
| 268 | 2,6-Difluorobenzenesulfonyl chloride | | 430.1121 |
| 269 | 5-Chlorothiophene-2-sulfonyl chloride | | 434.0519 |
| 270 | 2-Mesitylenesulfonyl chloride | | 436.1814 |
| 271 | 2-Methoxy-4-methylbenzenesulfonyl chloride | | 438.1613 |
| 272 | 3-Nitrobenzenesulfonyl chloride | | 439.1199 |
| 273 | 1-Naphthalenesulfonyl chloride | | 444.1506 |
| 274 | (−)-Camphor-10-sulfonyl chloride | | 468.2098 |

-continued

| Example | Reagent | R | Measured Mass (M + H) |
|---|---|---|---|
| 275 | D-(+)-10-Camphorsulfonyl chloride | | 468.2106 |
| 276 | 4-Biphenylsulfonyl chloride | | 470.1639 |
| 277 | 2-Bromobenzenesulfonyl chloride | | 472.0459 |
| 278 | 3-Bromobenzenesulfonyl chloride | | 472.0471 |
| 279 | 2-(Trifluoromethoxy)benzenesulfonyl chloride | | 478.1171 |
| 280 | 4-(Trifluoromethoxy)benzenesulfonyl chloride | | 478.1155 |
| 281 | 4-Phenoxybenzenesulfonyl chloride | | 486.1613 |

-continued

| Example | Reagent | R | Measured Mass (M + H) |
|---------|---------|---|------------------------|
| 282 | Dansyl chloride | dansyl group | 487.1920 |
| 283 | Isopropyl isocyanate | –C(O)NH-CH(CH₃)₂ | 339.1965 |
| 284 | n-Propyl isocyanate | –C(O)NH-CH₂CH₂CH₃ | 339.1947 |
| 285 | tert-Butylisocyanate | –C(O)NH-C(CH₃)₃ | 353.2108 |
| 286 | Dimethylcarbamoyl chloride | –C(O)N(CH₃)₂ | 325.1804 |
| 287 | Phenyl isocyanate | –C(O)NH-Ph | 373.1803 |
| 288 | Cyclohexane isocyanate | –C(O)NH-cyclohexyl | 379.2275 |
| 289 | Benzyl isocyanate | –C(O)NH-Ph | 387.1943 |

-continued

| Example | Reagent | R | Measured Mass (M + H) |
|---|---|---|---|
| 290 | m-Tolyl isocyanate | -C(=O)-NH-(3-methylphenyl) | 387.1951 |
| 291 | o-Tolyl isocyanate | -C(=O)-NH-(2-methylphenyl) | 387.1937 |
| 292 | p-Tolyl isocyanate | -C(=O)-NH-(4-methylphenyl) | 387.1959 |
| 293 | 2-Fluorophenyl isocyanate | -C(=O)-NH-(2-fluorophenyl) | 391.1706 |
| 294 | 3-Fluorophenyl isocyanate | -C(=O)-NH-(3-fluorophenyl) | 391.1705 |
| 295 | Cyclohexyl isothiocyanate | -C(=S)-NH-cyclohexyl | 395.2041 |
| 296 | 2-Tetrahydrofurfuryl isothiocyanate | -C(=S)-NH-CH$_2$-(tetrahydrofuran-2-yl) | 397.1836 |
| 297 | 3-Cyanophenyl isocyanate | -C(=O)-NH-(3-cyanophenyl) | 398.1749 |

-continued

| Example | Reagent | R | Measured Mass (M + H) |
|---|---|---|---|
| 298 | 4-Cyanophenyl isocyanate | -C(O)-NH-C6H4-CN | 398.1752 |
| 299 | Benzoyl isocyanate | -C(O)-NH-C(O)-C6H5 | 401.1750 |
| 300 | (R)-(+)-1-Phenylethyl isocyanate | -C(O)-NH-CH(CH3)-C6H5 | 401.2080 |
| 301 | (S)-(−)-1-Phenylethyl isocyanate | -C(O)-NH-CH(CH3)-C6H5 | 401.2078 |
| 302 | 3-Methylbenzyl isocyanate | -C(O)-NH-CH2-C6H4-CH3 | 401.2122 |
| 303 | 4-Methylbenzyl isocyanate | -C(O)-NH-CH2-C6H4-CH3 | 401.2096 |
| 304 | Phenethyl isocyanate | -C(O)-NH-CH2-CH2-C6H5 | 401.2127 |

-continued

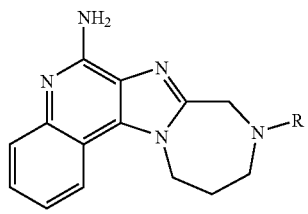

| Example | Reagent | R | Measured Mass (M + H) |
|---------|---------|---|-----------------------|
| 305 | 1-Piperidinecarbonyl chloride | *piperidine-1-carbonyl* | 365.2122 |
| 306 | 2-Methoxyphenyl isocyanate | *2-methoxyphenyl carbamoyl* | 403.1877 |
| 307 | 3-Methoxyphenyl isocyanate | *3-methoxyphenyl carbamoyl* | 403.1902 |
| 308 | 4-Methoxyphenyl isocyanate | *4-methoxyphenyl carbamoyl* | 403.1908 |
| 309 | Morpholine-4-carbonyl chloride | *morpholine-4-carbonyl* | 367.1911 |
| 310 | 4-Fluorobenzyl isocyanate | *4-fluorobenzyl carbamoyl* | 405.1851 |
| 311 | 2-Chlorophenyl isocyanate | *2-chlorophenyl carbamoyl* | 407.1408 |

-continued
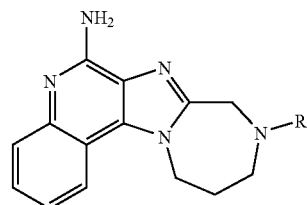
| Example | Reagent | R | Measured Mass (M + H) |
|---|---|---|---|
| 312 | trans-2-Phenylcyclopropyl isocyanate | | 413.2106 |
| 313 | 3-Acetylphenyl isocyanate | | 415.1899 |
| 314 | 4-(Dimethylamino)phenyl isocyanate | | 416.2213 |
| 315 | 4-Methoxybenzyl isocyanate | | 417.2069 |
| 316 | Phenethyl isothiocyanate | | 417.1895 |
| 317 | 2-Nitrophenyl isocyanate | | 418.1662 |
| 318 | 3-(Methylthio)phenyl isocyanate | | 419.1671 |

-continued

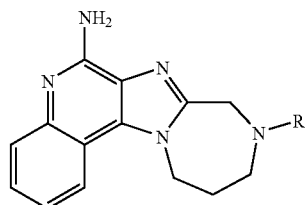

| Example | Reagent | R | Measured Mass (M + H) |
|---|---|---|---|
| 319 | 4-(Methylthio)phenyl isocyanate | *(acetamide-4-methylthiophenyl)* | 419.1695 |
| 320 | 1-Naphthyl isocyanate | *(acetamido-1-naphthyl)* | 423.1969 |
| 321 | N-Methyl-N-phenylcarbamoyl chloride | *(N-methyl-N-phenylacetamide)* | 387.1961 |
| 322 | 3-(Diethylamino)propyl isothiocyanate | *(thioacetamido-propyl-diethylamine)* | 426.2465 |
| 323 | Methyl 3-isocyanatobenzoate | *(3-acetamido methyl benzoate)* | 431.1852 |
| 324 | 1-Adamantyl isocyanate | *(1-adamantyl acetamide)* | 431.2549 |
| 325 | 2-(Trifluoromethyl)phenyl isocyanate | *(2-trifluoromethylphenyl acetamide)* | 441.1647 |

-continued

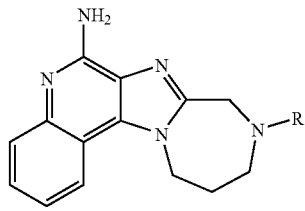

| Example | Reagent | R | Measured Mass (M + H) |
|---|---|---|---|
| 326 | 3-(Trifluoromethyl)phenyl isocyanate | ![structure] | 441.1679 |
| 327 | 2-Biphenylyl isocyanate | ![structure] | 449.2090 |
| 328 | 2-(Trifluoromethoxy)phenyl isocyanate | ![structure] | 457.1633 |
| 329 | 3-Phenoxyphenyl isocyanate | ![structure] | 465.2073 |

Examples 330-362

Part A mCPBA (3.89 g of 77% pure material, 17.36 mmol) was added to a solution of tert-butyl 11-{[tert-butyl(dimethyl)silyl]oxy}-11,12-dihydro-8H-[1,4]diazepino[1',2':1,2]imidazo[4,5-c]quinoline-9(10H)-carboxylate (4.07 g, 8.68 mol chloroform, and the reaction was stirred for 30 minutes at ambient temperature. Additional mCPBA (0.5 equivalent) was added, and the reaction was stirred for four hours. Ammonium hydroxide (50 mL) was added with vigorous stirring, and after ten minutes, p-toluenesulfonyl chloride (1.82 g, 9.55 mmol) was added. The reaction was stirred overnight at ambient temperature and then concentrated under reduced pressure. The crude product was purified by column chromatography on silica gel (eluting sequentially with 98.5:1:0.5 and 89:10:1 dichloromethane:methanol:ammonium hydroxide), and the resulting product was dried under high vacuum to provide 2.25 g of tert-butyl 6-amino-11-{[tert-butyl(dimethyl)silyl]oxy}-11,12-dihydro-8H-[1,4]diazepino[1',2':1,2]imidazo[4,5-c]quinoline-9(10H)-carboxylate.

Part B

Hydrochloric acid (75 mL of a 4 N solution in 1,4-dioxane) was added to tert-butyl 6-amnino-11-{[tert-butyl(dimethyl)silyl]oxy}-11,12-dihydro-8H-[1,4]diazepino[1',2':1,2]imidazo[4,5-c]quinoline-9(10H)-carboxylate (2.15 g, 4.45 mmol), and the reaction was stirred for four hours at ambient temperature and then concentrated under reduced pressure. The residue was washed with dichloromethane and dried overnight under high vacuum to provide 930 mg of 11-{[tert-butyl(dimethyl)silyl]oxy}-9,10,11,12-tetrahydro-8H-[1,4]diazepino[1',2':1,2]imidazo[4,5-c]quinolin-6-amine hydrochloride as a light brown powder.

Part C

The reagent (0.11 mmol) indicated in the table below was added to a solution of 11-{[tert-butyl(dimethyl)silyl]oxy}-9,10,11,12-tetrahydro-8H-[1,4]diazepino[1',2':1,2]imidazo[4,5-c]quinolin-6-amine hydrochloride (24 mg, 0.077 mmol) and N,N-diisopropylethylamine (0.0225 mL, 0.13 mmol) in chloroform (1 L) in a test tube. For Examples 330-348, the test tube was capped and shaken overnight at ambient temperature. For Examples 349-362, the test tube was capped, heated at 50° C. for four hours, and then shaken overnight at ambient temperature. The reaction mixtures were separated by solid-supported liquid-liquid extraction according to the following procedure. Each reaction was loaded onto diatomaceous earth that had been treated with 600 μL of 1 N sodium hydroxide for 20 minutes. After ten minutes, chloroform (500 μL) was added to elute the product from the diatomaceous earth into a well of a microtitre plate. After an additional 15 minutes, the process was repeated with additional chloroform (500 μL). The solvent was then removed by vacuum centrifugation.

Part D

THF (1 mL) was added to each product from Part C located in a well of the microtitre plate described in Part C. The wells were capped and shaken until the mixture became homogeneous. The solutions were cooled to −20° C., and tetrabutylammonium fluoride (300 μL of a 1.0 M solution in THF) was added. The plate was shaken, returned to the cold bath, and then allowed to warm to ambient temperature overnight. Trifluoroacetic acid (25 μL) was added to each well, and the plate was shaken carefully. The volatiles were then removed by vacuum centrifugation. Some of the compounds were purified by prep HPLC using the method described above. Other compounds were purified using a Waters OASIS Sample Extractions Cartridge MCX (5 cc) according to the following procedure prior to purification by prep HPLC. The sample was dissolved in methanol (2 mL) and passed through the cartridge. The cartridge was washed with methanol (2×2 mL) and transferred to a clean test tube. A solution of 7 N ammonia in methanol (3×2 mL) was then passed through the cartridge, and the basic solution was collected and concentrated. The table below shows the acid chloride, sulfonyl chloride, isocyanate, carbamoyl chloride, or sulfamoyl chloride used for each example, the structure of the resulting compound, and the observed accurate mass for the isolated trifluoroacetate salt.

Examples 330-362

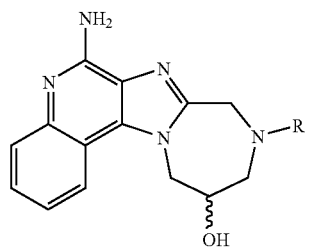

| Example | Reagent | R | Measured Mass (M + H) |
|---|---|---|---|
| 330 | Propionyl chloride | | 326.1619 |
| 331 | Methyl chloroformate | | 328.1409 |
| 332 | Cyclopropanecarbonyl chloride | | 338.1617 |
| 333 | Butyryl chloride | | 340.1750 |
| 334 | Ethyl chloroformate | | 342.1549 |

-continued

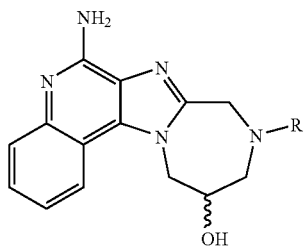

| Example | Reagent | R | Measured Mass (M + H) |
|---|---|---|---|
| 335 | Cyclobutanecarbonyl chloride | (cyclobutyl-C(O)-) | 352.1789 |
| 336 | 3-Methylthiopropionyl chloride | (-C(O)CH2CH2SCH3) | 372.1496 |
| 337 | 2-Thiopheneacetyl chloride | (-C(O)CH2-thiophene) | 394.1355 |
| 338 | 2-Chlorobenzoyl chloride | (-C(O)-2-Cl-C6H4) | 408.1212 |
| 339 | Nicotinoyl chloride hydrochloride | (-C(O)-3-pyridyl) | 375.1569 |
| 340 | 3,4-Dimethoxybenzoyl chloride | (-C(O)-3,4-(OCH3)2-C6H3) | 434.1830 |
| 341 | Dimethylsulfamoyl chloride | (-S(O)2N(CH3)2) | 377.1381 |
| 342 | Benzenesulfonyl chloride | (-S(O)2-C6H5) | 410.1275 |

-continued
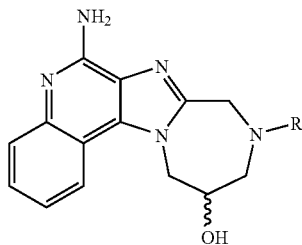
| Example | Reagent | R | Measured Mass (M + H) |
|---|---|---|---|
| 343 | 3-Methylbenzenesulfonyl chloride | | 424.1437 |
| 344 | o-Toluenesulfonyl chloride | | 424.1450 |
| 345 | p-Toluenesulfonyl chloride | | 424.1442 |
| 346 | 3-Cyanobenzenesulfonyl chloride | | 435.1243 |
| 347 | 3-Methoxybenzenesulfonyl chloride | | 440.1366 |
| 348 | 3,4-Dimethoxybenzenesulfonyl chloride | | 470.1510 |
| 349 | Ethyl isocyanate | | 341.1724 |
| 350 | Methyl isothiocyanate | | 343.1343 |

-continued

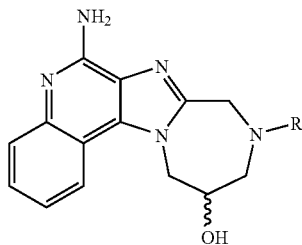

| Example | Reagent | R | Measured Mass (M + H) |
|---------|---------|---|----------------------|
| 351 | n-Propyl isothiocyanate | -C(=S)-NH-CH2CH2CH3 | 371.1641 |
| 352 | N,N-Dimethylcarbamoyl chloride | -C(=O)-N(CH3)2 | 341.1729 |
| 353 | Pentyl isocyanate | -C(=O)-NH-(CH2)4-CH3 | 383.2206 |
| 354 | Phenyl isocyanate | -C(=O)-NH-Ph | 389.1733 |
| 355 | m-Tolyl isocyanate | -C(=O)-NH-(3-MeC6H4) | 403.1882 |
| 356 | 4-Morpholinecarbonyl chloride | -C(=O)-morpholinyl | 383.1808 |
| 357 | 2-Chlorophenyl isocyanate | -C(=O)-NH-(2-ClC6H4) | 423.1343 |
| 358 | 4-Methyl-1-piperazinecarbonyl chloride | -C(=O)-(4-methylpiperazin-1-yl) | 396.2111 |

-continued

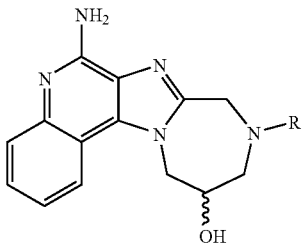

| Example | Reagent | R | Measured Mass (M + H) |
|---|---|---|---|
| 359 | N-Methyl-N-phenylcarbamoyl chloride | | 403.1892 |
| 360 | 2-Morpholinoethyl isothiocyanate | | 442.2038 |
| 361 | 4-(Dimethylamino)phenyl isothiocyanate | | 448.1911 |
| 362 | 3,4-Dimethoxyphenyl isocyanate | | 449.1924 |

Example 363

9-(Methylsulfonyl)-2,3,4,8,9,10,11,12-octahydro-1H-[1,4]diazepino[1',2':1,2]imidazo[4,5c]quinolin-6-amine

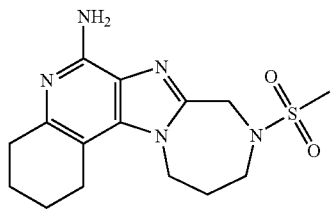

Part A

Triethylamine (2.32 mL, 16.7 mmol) was added to a suspension of 9,10,11,12-tetrahydro-8H-[1,4]diazepino[1',2':1,2]imidazo[4,5-c]quinolin-6-amine hydrochloride (1.61 g, 5.56 mmol, Example 7 Part A) in DMF (20 mL). The mixture was sonicated for ten minutes at 80° C., and methanesulfonyl chloride (764 mg, 6.67 mmol) was slowly added. The mixture was stirred at ambient temperature overnight. The solvent was removed under reduced pressure. Unsuccessful attempts were made to purify the product, and ultimately, the product was isolated by filtration to provide 894 mg of 9-(methylsulfonyl)-9,10,11,12-tetrahydro-8H-[1,4]diazepino[1',2':1,2]imidazo[4,5-c]quinolin-6-amine containing some impurities.

Part B

Platinum (II) oxide (613.14 mg, 2.7 mmol) was added to a Parr vessel containing the material from Part A and trifluoroacetic acid (20 mL), and the reaction was placed under hydrogen pressure (50 psi, $3.4 \times 10^5$ Pa) overnight. The trifluoroacetic acid was then removed under reduced pressure, and the residue was mixed with methanol and filtered. The filtrate was concentrated under reduced pressure, and the residue was stirred with hydrogen chloride (20 mL of a 4 N solution in 1,4-dioxane) for ten minutes. The mixture was filtered, and the filtrate was concentrated under reduced pressure. A solution of 0.5 M potassium hydroxide in methanol was added to the residue until the mixture was pH 13, and the mixture was stirred for 15 minutes. The solvent was removed under reduced pressure, and the residue was dissolved in chloroform. The resulting solution was washed sequentially with 10% aqueous sodium carbonate, 2 N aqueous sodium hydroxide, and brine and then concentrated under reduced pressure.

The residue was purified by column chromatography on a COMBIFLASH system (available from Isco, Inc., Lincoln, Nebr., USA) (eluting with a gradient of 1-10% methanol in dichloromethane) followed by recrystallization from acetonitrile. The crystals were dried overnight in a vacuum oven at 65° C. to provide 9-(methylsulfonyl)-2,3,4,8,9,10,11,12-octahydro-1H-[1,4]diazepino[1',2':1,2]imidazo[4,5-c]quinolin-6-amine as a white powder, mp 270-272° C.

$^1$H NMR (300 MHz, DMSO-D6) δ 5.85 (s, 2H), 4.69 (s, 2H), 4.56 (t, J=3.9 Hz, 2H), 3.65 (t, J=6.0 Hz, 2H), 2.94 (t, J=7.5 Hz, 2H), 2.73 (s, 3H), 2.65 (m, 2H), 2.07 (m, 2H), 1.75 (m, 4H);

MS (APCI) m/z 336 (M+H)$^+$;

Anal. Calcd for $C_{15}H_{21}N_5O_2S \cdot 0.30H_2O$: C, 52.86; H, 6.39; N, 20.55. Found: C, 53.05; H, 6.07; N, 20.20.

Example 364

9-(Methylsulfonyl)-9,10,11,12-tetrahydro-8H-[1,4] diazepino[1',2':1,2]imidazo[4,5-c][1,5]naphthyridin-6-amine

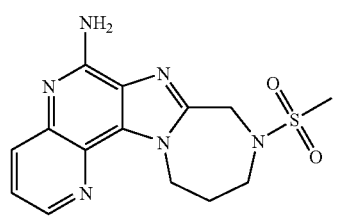

Part A

Phosphorus oxychloride (31.7 mL, 340 mmol) was added dropwise to a stirred suspension of 3-nitro[1,5]naphthyridine-4-ol (50.0 g, 262 mmol) in 350 mL of DMF that was cooled with a water bath surrounding the reaction vessel. The resulting green suspension was stirred at ambient temperature for 5 hours and poured into 1.5 L of ice water and stirred for an additional hour. The suspension was filtered, washed with water (3×150 mL), and the resulting orange filter cake was dissolved in dichloromethane (800 mL) and washed with saturated aqueous sodium bicarbonate. The layers were separated and the organic layer was dried over magnesium sulfate, filtered, and concentrated under reduced pressure to afford 50.49 g of 4-chloro-3-nitro[1,5]naphthyridine as an orange solid.

Part B

Di-tert-butyl dicarbonate (45.0 g, 206 mmol) was dissolved in 200 mL of THF and added via an addition funnel to a solution of 1,3-diaminopropane (51.6 mL, 618 mmol) in 100 mL of THF. The internal temperature of the reaction mixture was maintained below 8° C. After addition was complete, the reaction mixture was allowed to warm to ambient temperature and stirred overnight. The resulting mixture was diluted with 250 mL of water and 400 mL of ethyl acetate and the layers were separated. The aqueous layer was extracted with ethyl acetate (3×100 mL). The combined organic layers were concentrated under reduced pressure and the remaining material was diluted in 800 mL of water. The pH of the combined aqueous layers was adjusted to pH 4 by the addition of 2M hydrochloric acid. The solution was extracted with dichloromethane (3×200 mL). The pH of the aqueous solution was adjusted to 12 using a 2M solution of sodium hydroxide and extracted with dichloromethane (6×150 mL). The combined organic layers from the final set of extractions were washed with brine (300 mL), dried over sodium sulfate, filtered, and concentrated under reduced pressure to afford 25.01 g of tert-butyl 3-aminopropylcarbamate as a colorless oil.

Part C

A solution of tert-butyl 3-aminopropylcarbamate (15.7 g, 90.2 mmol) in dichloromethane (50 mL) was added dropwise over 30 minutes to a solution of 4-chloro-3-nitro[1,5]naphthyridine (18.0 g, 85.9 mmol) and triethylamine (15.6 mL, 112 mmol) in dichloromethane (235 mL) at room temperature. The reaction mixture was stirred for 2.5 hours and then concentrated under reduced pressure to afford an orange solid. Water (300 mL) was added and the mixture was stirred for one hour. The solid was isolated by filtration, washed with water (3×50 mL), and dried under vacuum at 70° C. to afford 29.5 g of tert-butyl 3-[(3-nitro[1,5]naphthyridin-4-yl)amino]propylcarbamate as a yellow solid.

Part D

A mixture of tert-butyl 3-[(3-nitro[1,5]naphthyridin-4-yl)amino]propylcarbamate (20.0 g, 57.6 mmol), 5% platinum on carbon, and ethyl acetate was hydrogenated on a Parr apparatus for two hours at 30 psi (2.1×10$^5$ Pa). The mixture was filtered through CELITE filter agent, which was rinsed afterwards with ethyl acetate (150 mL). The filtrate was concentrated to afford tert-butyl 3-[(3-amino[1,5]naphthyridin-4-yl)amino]propylcarbamate as a yellow foam, all of which was used in the next step.

Part E

Chloroacetyl chloride (5.00 mL, 63.4 mmol) was added dropwise to a 0° C. solution of tert-butyl 3-[(3-amino[1,5] naphthyridin-4-yl)amino]propylcarbamate (from Part D, approximately 57.6 mmol) in dichloromethane (230 mL). The reaction was allowed to warm to room temperature and was stirred for 1 hour. The solvent was removed under reduced pressure to afford tert-butyl 3-({3-[(chloroacetyl) amino][1,5]naphthyridin-4-yl}amino)propylcarbamate hydrochloride as a solid, all of which was used in the next step.

Part F

To a solution of tert-butyl 3-({3-[(chloroacetyl)amino][1, 5]naphthyridin-4-yl}amino)propylcarbamate hydrochloride (from Part E, approximately 57.6 mmol) in 3:1 ethanol/water (240 mL) was added 6 M aqueous potassium carbonate. The reaction mixture was stirred at room temperature for 1 hour, 40° C. for 1.5 hour, then at room temperature overnight. The volatiles were removed under reduced pressure and the residue was partitioned between dichloromethane (250 mL) and water (150 mL). The aqueous layer was extracted with dichloromethane (2×75 mL). The organic layers were combined, dried over magnesium sulfate, filtered, and concentrated under reduced pressure to afford 18.9 g of tert-butyl 3-[2-(chloromethyl)-1H-imidazo[4,5-c][1,5]naphthyridin-1-yl]propylcarbamate.

Part G

Concentrated hydrochloric acid (20 mL) was added to a suspension of tert-butyl 3-[2-(chloromethyl)-1H-imidazo[4,5-c][1,5]naphthyridin-1-yl]propylcarbamate (12.55 g, 33.4 mmol) in methanol (135 mL). The resulting yellow solution was stirred for 48 hours and the liquid was removed via filtration. The resulting solid filter cake was dried overnight in a vacuum, oven at 40° C. to afford 9.62 g of 3-[2-(chloromethyl)-1H-imidazo[4,5-c]-1,5-naphthyridin-1-yl]propylamine hydrochloride as a pale yellow solid.

Part H

Triethylamine (4.0 mL, 28.8 mmol) was added to a suspension of 3-[2-(chloromethyl)-1H-imidazo[4,5-c]-1,5-naphthyridin-1-yl]propylamine hydrochloride (3.0 g, 9.61 mmol) in dichloromethane (100 mL). Methanesulfonic anhydride (2.01 g, 11.53 mmol) was added to the reaction mixture and stirred for 1 hour at ambient temperature. The mixture was diluted with dichloromethane (50 mL) and saturated aqueous sodium bicarbonate and the layers were separated. The aqueous layer was extracted with dichlormethane (35 mL) and the combined organic layers were dried over magnesium sulfate, filtered, and concentrated to afford 3.09 g of N-{3-[2-(chloromethyl)-1H-imidazo[4,5-c][1,5]naphthyridin-1-yl]propyl}methanesulfonamide as a tan solid.

Part I

A reaction vessel was charged with acetone (100 mL) and cesium carbonate (3.13 g, 9.61 mmol). N-{3-[2-(Chloromethyl)-1H-imidazo[4,5-c]-1,5-naphthyridin-1-yl]propyl}methanesulfonamide (3.09 g, 8.73 mmol) was dissolved in acetone (40 mL) and methanol (10 mL) and added over 50 minutes to the reaction vessel. The reaction mixture was stirred at ambient temperature for 1 hour. The mixture was concentrated under reduced pressure and the residue was partitioned between water (75) mL and dichlormethane (100 mL). The layers were separated and the aqueous later was extracted with dichloromethane (40 mL). The combined organic layers were dried over magnesium sulfate, filtered, and concentrated under reduced pressure to afford 2.42 g of an orange solid. The material was triturated with acetonitrile to afford 1.75 g of 9-(methylsulfonyl)-9,10,11,12-tetrahydro-8H-[1,4]diazepino[1',2':1,2]imidazo[4,5-c]-1,5-naphthyridin as a tan powder.

Part J mCPBA (70% pure, 2.72 g, 11.03 mmol) was added to a solution of 9-(methylsulfonyl)-9,10,11,12-tetrahydro-8H-[1,4]diazepino[1',2':1,2]imidazo[4,5-c]-1,5-naphthyridine (1.75 g, 5.51 mmol) in chloroform (30 mL) and stirred 2 hours at ambient temperature. Concentrated ammonium hydroxide (10 mL), chloroform (20 mL) and p-toluenesulfonyl chloride (1.16 g, 6.07 mmol) were sequentially added and the reaction mixture was stirred for 1 hour and then diluted with chloroform (20 mL) and additional p-toluenesulfonyl chloride (1.16 g, 6.07 mmol). The suspension was filtered and the resulting tan solid was triturated with 2M sodium hydroxide to afford 1.25 g of solid. The material was triturated with hot acetonitrile, hot methanol, and ethanol. The material was adsorbed onto 4 g of silica gel and purified by column chromatography on a HORIZON HPFC system (an automated, modular high-performance flash purification product available from Biotage, Inc, Charlottesville, Va., USA) (silica gel, eluting with 0-50% chloroform:methanol:ammonium hydroxide (CMA) in chloroform) and concentrated to afford a pale yellow solid. The material was triturated with hot methanol, filtered, and dried under high vacuum at 120° C. overnight to afford 9-(methylsulfonyl)-9,10,11,12-tetrahydro-8H-[1,4]diazepino[1',2':1,2]imidazo[4,5-c]-1,5-naphthyridin-6-amine as beige needles, mp greater than 250° C.

MS (ESI) m/z 333 (M+H)$^+$;

Anal. calcd for $C_{14}H_{16}N_6O_2S$: C, 50.59; H, 4.85; N, 25.28. Found: C, 50.30; H, 4.71; N, 25.19.

Example 365

3-Bromo-9-(methylsulfonyl)-9,10,11,12-tetrahydro-8H-[1,4]diazepino[1',2':1,2]imidazo[4,5-c]quinolin-6-amine

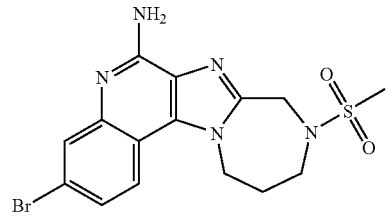

Part A

Triethylamine (8.9 mL, 64 mmol) and tert-butyl N-(3-aminopropyl)carbamate (30.95 g, 177.6 mmol) were added to a solution of 7-bromo-4-chloro-3-nitroquinoline (42.55 g, 148.0 mmol, U.S. patent application publication no. US 2004/0147543, Example 1, Parts A through D) in DMF (500 mL), and the reaction was stirred for four days at ambient temperature. The reaction mixture was poured into water (2 L), and a precipitate formed. The precipitate was isolated by filtration and dried in a vacuum oven overnight at 65° C. to provide 56.4 g of tert-butyl 3-[(7-bromo-3-nitroquinolin-4-yl)amino]propylcarbamate.

Part B

A solution of tert-butyl 3-[(7-bromo-3-nitroquinolin-4-yl)amino]propylcarbamate (56.4 g, 133 mmol) in dichloromethane (150 mL) and ethyl acetate (500 mL) and 5% platinum on carbon (15.52 g, 79.56 mmol) were added to a hydrogenation vessel, which was placed under hydrogen pressure (50 psi, 3.4×10$^5$ Pa) and shaken overnight. The reaction mixture was filtered, and the filtrate was concentrated under reduced pressure. The residue was dried under reduced pressure to provide 52.17 g of tert-butyl 3-[(3-amino-7-bromoquinolin-4-yl)amino]propylcarbamate.

Part C

Triethylamine (26.7 g, 264 mmol) was added to a solution of tert-butyl 3-[(3-amino-7-bromoquinolin-4-yl)amino]propylcarbamate (52.17 g, 132.0 mmol) in dichloromethane (370 mL). Chloroacetyl chloride (15.65 g, 138.6 mmol) was added, and the reaction was stirred overnight at ambient temperature. The solvent was removed under reduced pressure, and the residue was stirred in ethanol (1 L) overnight at ambient temperature. The solvent was removed under reduced pressure, and the residue was dissolved in chloroform. The resulting solution was washed twice with water, concentrated under reduced pressure, and dried under high vacuum to provide 41.63 g of tert-butyl 3-[7-bromo-2-(chloromethyl)-1H-imidazo[4,5-c]quinolin-1-yl]propylcarbamate.

Part D

Potassium tert-butoxide (110 mL of a 1 M solution in THF) was added to a solution of tert-butyl 3-[7-bromo-2-(chloromethyl)-1H-imidazo[4,5-c]quinolin-1-yl]propylcarbamate (41.63 g, 91.74 mmol) in THF (400 mL). The reaction was stirred for ten minutes at ambient temperature and concentrated under reduced pressure to provide tert-butyl 3-bromo-11,12-dihydro-8H-[1,4]diazepino[1',2':1,2]imidazo[4,5-c]quinoline-9(10H)-carboxylate in a crude mixture which was used without purification in Part E.

Part E mCPBA (49.4 g of 77%, 220.2 mmol) was added to a solution of the material from Part D in chloroform (400 mL), and the reaction was stirred for 30 minutes at ambient temperature before additional mCPBA (about 1.3 equivalent) was added. The reaction mixture was stirred for two hours at ambient temperature. Ammonium hydroxide (350 mL) and p-toluenesulfonyl chloride (19.24 g, 100.9 mmol) were then added, and the reaction mixture was stirred vigorously overnight at ambient temperature. The organic layer was separated and concentrated under reduced pressure to provide tert-butyl 6-amino-3-bromo-11,12-dihydro-8H-[1,4]diazepino[1',2':1,2]imidazo[4,5-c]quinoline-9(10H)-carboxylate in a crude mixture which was used without purification in Part F.

Part F

Hydrogen chloride (400 mL of a 4 N solution in 1,4-dioxane) was added to a solution of the material from Part E in methanol (350 mL). The reaction was stirred overnight at ambient temperature; a precipitate formed. Diethyl ether was added, and the precipitate was isolated by filtration, washed with diethyl ether, and dried under vacuum. The precipitate was then dissolved in hot methanol and treated with triethylamine to form the free base. The methanol and triethylamine were removed under reduced pressure, and the residue was washed several times with dichloromethane to provide 18.25 g of 3-bromo-9,10,11,12-tetrahydro-8H-[1,4]diazepino[1',2':1,2]imidazo[4,5-c]quinolin-6-amine.

Part G

Triethylamine (16.68 g, 164.8 mmol) and methanesulfonyl chloride (6.92 g, 60.4 mmol) were added to a solution of 3-bromo-9,10,11,12-etrahydro-8H-[1,4]diazepino[1',2':1,2]imidazo[4,5-c]quinolin-6-amine (18.25 g, 54.94 mmol) in DMF (200 mL), and the mixture was stirred at ambient temperature overnight and filtered. After the solvent was removed under reduced pressure, the residue was suspended in acetonitrile to provide a solid, which was isolated by filtration to provide 1.87 g of 3-bromo-9-(methylsulfonyl)-9,10,11,12-tetrahydro-8H-[1,4]diazepino[1',2':1,2]imidazo[4,5-c]quinolin-6-amine. The filtrate was concentrated under reduced pressure, and the residue was purified by column chromatography on silica gel (eluting with 2 N ammonia in methanol/chloroform in a 43-minute gradient from 0:100 to 15:85). In some fractions, the product crystallized and was isolated by filtration to provide 550.9 mg of product. The rest of the fractions containing the product were combined and concentrated under reduced pressure, and the residue was recrystallized from acetonitrile/ethanol to provide 1.426 g of 3-bromo-9-(methylsulfonyl)-9,10,11,12-tetrahydro-8H-[1,4]diazepino[1',2':1,2]imidazo[4,5-c]quinolin-6-amine as a light yellow solid, mp 303° C.

$^1$H NMR (300 MHz, DMSO-D6) δ 8.22 (d, J=8.8 Hz, 1H), 7.74 (d, J=2.1 Hz, 1H), 7.35 (dd, J=8.8, 2.2 Hz, 1H), 6.85 (s, 2H), 4.86 (t, J=4.5 Hz, 2H), 4.81 (s, 2H), 3.72 (t, J=5.3 Hz, 2H), 2.80 (s, 3H), 2.24-2.16 (m, 2H); $^{13}$C NMR (75 MHz, DMSO-D6) δ 153.1, 151.2, 146.9, 133.6, 128.3, 126.2, 123.7, 122.6, 120.0, 114.2, 49.6, 46.4, 45.7, 38.3, 27.7;

MS (APCI) m/z 411 (M+H)$^+$;

Anal. Calcd for $C_{15}H_{16}BrN_5O_2S$: C, 43.91; H, 3.93; N, 17.07. Found: C, 44.07; H, 3.75; N, 17.32.

The mother liquor from the recrystallization was concentrated to provide an additional 5.43 g of product.

Example 366

9-(Methylsulfonyl)-3-pyridin-3-yl-9,10,11,12-tetrahydro-8H-[1,4]diazepino[1',2':1,2]imidazo[4,5-c]quinolin-6-amine

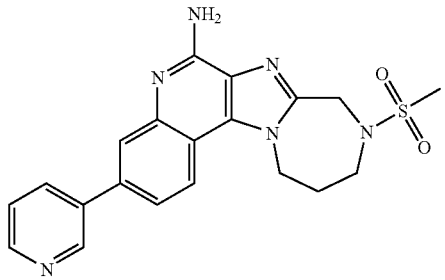

Sodium carbonate (0.140 g, 1.32 mmol), triphenylphosphine (74.7 mg, 0.33 mmol), 3-pyridine boronic acid (0.149 g, 1.21 mmol), and palladium (II) acetate (25 mg, 0.11 mmol) were sequentially added to a solution of 3-bromo-9-(methylsulfonyl)-9,10,11,12-tetrahydro-8H-[1,4]diazepino[1',2':1,2]imidazo[4,5-c]quinolin-6-amine (0.450 g, 1.1 mmol) in n-propanol (15 mL), methanol (10 mL), and water (5 mL). The reaction was heated at 80° C. overnight and then concentrated under reduced pressure. The residue was mixed with dichloromethane, and the resulting solid was isolated by filtration. The solid was purified by column chromatography on silica gel (eluting with 2 N ammonia in methanol/chloroform in a gradient from 0% to 25%. The resulting solid was mixed with material from another run and purified again by column chromatography on silica gel under the same conditions to provide 76.8 mg of 9-(methylsulfonyl)-3-pyridin-3-yl-9,10,11,12-tetrahydro-8H-[1,4]diazepino[1',2':1,2]imidazo[4,5-c]quinolin-6-amine, as a beige solid, mp 302° C.

$^1$H NMR (300 MHz, DMSO-d6) δ 8.99 (d, J=1.9 Hz, 1H), 8.60 (dd, J=4.7, 1.4 Hz, 1H), 8.40 (d, J=8.5 Hz, 1H), 8.18 (d, J=6.2 Hz, 1H), 7.92 (s, 1H), 7.60 (dd, J=8.6, 1.9 Hz, 1H), 7.54 (dd, J=7.8, 4.9 Hz, 1H), 6.71 (s, 2H), 4.94 (t, J=3.8 Hz, 2H), 4.84 (s, 2H), 3.74 (t, J=4.9 Hz, 2H), 2.81 (s, 3H), 2.24-2.29 (m, 2H);

MS (APCI) m/z 409 (M+H)$^+$;

Anal. calcd for $C_{20}H_{20}N_6O_2S \cdot 0.3H_2O$: C, 58.04; H, 5.02; N, 20.31. Found: C, 58.18; H, 4.78; N, 20.25.

Example 367

3-Bromo-9-(methylsulfonyl)-8,9,10,11-tetrahydropyrazino[1',2':1,2]imidazo[4,5-c]quinolin-6-amine

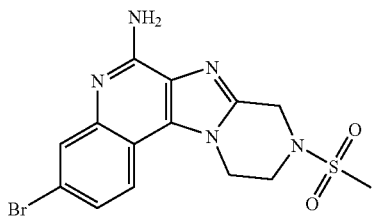

Part A

A modification of the method described in Part C of Example 365 was used to treat tert-butyl 2-[(3-amino-7-bromoquinolin-4-yl)amino]ethylcarbamate (66.69 g, 174.9 mmol, U.S. patent application publication no. US 2004/0147543, Example 386, Parts A and B) with triethylamine (35.4 g, 350 mmol) and chloroacetyl chloride (20.7 g, 183 mmol). After the reaction in ethanol was complete, a precipitate was present and was isolated by filtration to provide 38.42 g of tert-butyl 2-[7-bromo-2-(chloromethyl)-1H-imidazo[4,5-c]quinolin-1-yl]ethylcarbamate as white crystals. The filtrate was concentrated under reduced pressure, and the residue was purified by column chromatography on silica gel (eluting with 2 N ammonia in methanol/chloroform in a 33-minute gradient from 0:100 to 5:95) to provide an additional 4.89 g of product.

Part B

The method described in Part D of Example 365 was used to treat tert-butyl 2-[7-bromo-2-(chloromethyl)-1H-imidazo[4,5-c]quinolin-1-yl]ethylcarbamate (10.0 g, 22.7 mmol) with potassium tert-butoxide (27.29 mL of a 1 M solution in THF) with the modification that the reaction was stirred overnight to provide tert-butyl 3-bromo-10,11-dihydropyrazino[1',2':1,2]imidazo[4,5-c]quinohne-9(8H)-carboxylate in a crude mixture.

Part C

A modification of the method described in Part E of Example 365 was used to treat the material from Part B with mCPBA followed by ammonium hydroxide (50 mL) and p-toluenesulfonyl chloride (4.76 g, 25.0 mmol). The mCPBA was added in three portions (1.2 equivalents, 0.2 equivalent, and 0.2 equivalent) over a period of 100 minutes. The product tert-butyl 6-amino-3-bromo-10,11-dihydropyrazino[1',2':1,2]imidazo[4,5-c]quinoline-9(8H)-carboxylate was obtained in a crude mixture.

Part D

Hydrogen chloride (50 mL of a 4 N solution in 1,4-dioxane) was added to a solution of the material from Part C in dichloromethane (50 mL) and methanol (10 mL). The reaction was stirred overnight at ambient temperature; a precipitate formed. Diethyl ether was added, and the precipitate was isolated by filtration and washed with dichloromethane and diethyl ether. The precipitate was then dissolved in hot methanol and treated with triethylamine (30 mL) to form the free base. The methanol and triethylamine were removed under reduced pressure, and the residue was diluted with dichloromethane. The resulting suspension was filtered to provide 6.47 g of 3-bromo-8,9,10,11-tetrahydropyrazino[1',2':1,2]imidazo[4,5-c]quinolin-6-amine.

Part E

Triethylamine (3.82 g, 37.7 mmol) and methanesulfonyl chloride (2.38 g, 20.7 mmol) were sequentially added to a solution of 3-bromo-8,9,10,11-tetrahydropyrazino[1',2':1,2]imidazo[4,5-c]quinolin-6-amine (6.00 g, 18.9 mmol) in DMF (50 mL), and the mixture was stirred at ambient temperature overnight. A precipitate formed and was isolated by filtration, washed with dichloromethane, and dried to provide 600 mg of 3-bromo-9-(methylsulfonyl)-8,9,10,11-tetrahydropyrazino[1',2':1,2]imidazo[4,5-c]quinolin-6-amine as a white powder, mp 315-317° C.

$^1$H NMR (300 MHz, DMSO-D6) δ 8.01 (d, J=8.7 Hz, 1H), 7.75 (s, 1H), 7.39 (dd, J=8.7, 1.9 Hz, 1H), 6.89 (s, 2H), 4.75-4.70 (m, 4H), 3.85 (t, J=5.0 Hz, 2H), 3.13 (s, 3H);

MS (APCI) m/z 397 (M+H)$^+$;

Anal. Calcd for $C_{14}H_{14}BrN_5O_2S$: C, 42.43; H, 3.56; N, 17.67. Found: C, 42.10; H, 3.45; N, 17.50.

The filtrate was concentrated under reduced pressure, and the solid residue was boiled in methanol, filtered, and washed with methanol, acetonitrile, dichloromethane, and diethyl ether to provide 906.7 mg of product. The filtrate was concentrated under reduced pressure, and the residue was triturated with dichloromethane and isolated by filtration to provide an additional 2.8 g of product as the hydrochloride salt.

Example 368

3-(Benzyloxy)-9-(methylsulfonyl)-8,9,10,11-tetrahydropyrazino[1',2':1,2]imidazo[4,5-c]quinolin-6-amine

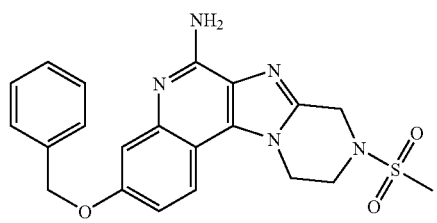

Part A

A mixture of triethyl orthoformate (92 mL, 0.55 mol) and 2,2-dimethyl-[1,3]-dioxane-4,6-dione (75.3 g, 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-[1,3]-dioxane-4,6-dione (170.65 g) was isolated as a tan, powdery solid.

¹H NMR (300 MHz, DMSO-d₆): δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H) 5.16 (s, 2H), 1.68 (s, 6H).

Part B

A mixture of 5-{[(3-benzyloxy)phenylimino]methyl}-2,2-dimethyl-[1,3]-dioxane-4,6-dione (170.65 g, 0.483 mol) and DOWTHERM A heat transfer fluid (800 mL) was heated to 100° C. and then slowly added to a flask containing DOWTHERM A heat transfer fluid (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder.

¹H NMR (300 MHz, DMSO-d₆): δ 11.53 (s, 1H), 7.99 (dd, J=2.4, 7.4 Hz, 1H), 7.79 (d, J=7.4 Hz, 1H), 7.50-7.32 (m, 5H), 7.00 (s, 1H), 6.98 (dd, J=2.5, 7.4 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

¹H NMR (300 MHz, DMSO-d₆): δ 12.77 (s, 1H), 9.12 (s, 1H), 8.17 (dd, J=3.3, 6.3 Hz, 1H), 7.51-7.33 (m, 5H), 7.21-7.17 (m, 2H), 5.25 (s, 2H).

Part D

DMF (100 mL) was cooled to 0° C., and phosphorous oxychloride (27.5 mL, 0.295 mol) was added dropwise. The resulting solution was stirred for 25 minutes and then added dropwise to a mixture of 7-benzyloxy-3-nitroquinolin-4-ol (72.87 g, 0.2459 mol) in DMF (400 mL). Following the addition, the reaction was heated at 100° C. for 5 minutes, cooled to ambient temperature, and poured into ice water with stirring. A tan precipitate formed, which was isolated by filtration and dissolved in dichloromethane. The resulting solution was dried over magnesium sulfate, filtered, and concentrated under reduced pressure to yield 72.9 g of 7-benzyloxy-4-chloro-3-nitroquinoline as a light brown solid.

¹H NMR (300 MHz, DMSO-d₆): δ 9.34 (s, 1H), 8.36 (d, J=8.7 Hz, 1H), 7.71 (d, J=2.4 Hz, 1H), 7.66 (dd, J=2.4, 9.3 Hz, 1H), 7.56-7.51 (m, 2H), 7.46-7.34 (m, 3H), 5.40 (s, 2H).

Material from a separate run was used in the next step.

Part E

Triethylamine (58.9 mL, 422.4 mmol, 1.5 eq) and tert-butyl N-(2-aminoethyl) carbamate (54.1 g, 337.9 mmol, 1.2 eq) were added sequentially to a solution of 7-benzyloxy-4-chloro-3-nitroquinoline (88.63 g, 281.6 mmol) in DMF (800 mL) and stirred for 4 hours at ambient temperature. The crude reaction mixture was poured into hot water with continuous stirring to afford bright a yellow precipitate. The yellow solid was filtered and dried under reduced pressure at 65° C. to afford 123.65 g of tert-butyl 2-[(7-benzyloxy-3-nitroquinolin-4-yl)amino]ethylcarbamate.

Part F tert-Butyl 2-[(7-benzyloxy-3-nitroquinolin-4-yl)amino]ethylcarbamate (40.0 g, 91.22 mmol) was dissolved in ethyl acetate (550 mL) and transferred to a Parr hydrogenation vessel charged with 5% platinum on carbon (10.68 g, 54.73 mmol, 0.03 eq). The vessel was purged with nitrogen gas and placed under hydrogen pressure (30 psi, $2.07 \times 10^5$ Pa) overnight. The catalyst was removed by filtration through a layer of CELITE filter aid, and the filter cake was rinsed with methanol and dichloromethane. The filtrate was concentrated under reduced pressure to provide 35.25 g tert-butyl 2-[(3-amino-7-benzyloxyquinolin-4-yl)amino]ethylcarbamate.

Part G

Triethylamine (24.0 mL, 172.58 mmol) was added to a solution of tert-butyl 2-[(3-amino-7-benzyloxyquinolin-4-yl)amino]ethylcarbamate (35.25 g, 86.29 mmol) in dichloromethane (400 mL), and the reaction was stirred at ambient temperature. Chloroacetyl chloride (6.87 mL, 86.29 mmol) was quickly added at ambient temperature, and the reaction was stirred for 10 minutes. The reaction mixture was concentrated under reduced pressure, and the residue was dissolved in ethanol (500 mL) and stirred for two days at ambient temperature. The mixture was concentrated under reduced pressure and the residue was recrystallized from dichloromethane to afford 6.23 g of tert-butyl 2-[7-benzyloxy-2-(chloromethyl)-1H-imidazo[4,5-c]quinolin-1-yl]ethylcarbamate. The mother liquor was divided into two portions which were separately purified by normal phase prep HPLC on silica gel (eluting with 2 N ammonia in methanol/chloroform in a 33-minute gradient from 0:100 to 5:95) and combined to provide an additional 24.21 g of product.

Part H

The method described in Part D of Example 365 was used to treat tert-butyl 2-[7-benzyloxy-2-(chloromethyl)-1H-imidazo[4,5-c]quinolin-1-yl]ethylcarbamate (23.55 g, 50.43 mmol) with potassium tert-butoxide (55.47 mL of a 1 M solution in THF) with the modification that crude product mixture was purified by normal phase prep HPLC on silica gel (eluting with 2 N ammonia in methanol/chloroform in a 66-minute gradient from 0:100 to 7:93) to provide 20.87 g of tert-butyl 3-benzyloxy-10,11-dihydropyrazino[1',2':1,2]imidazo[4,5-c]quinoline-9(8H)-carboxylate. Material from a different run was used in Part I.

Part I mCPBA (0.782 g of 77% purity, 3.49 mmol) was added to a solution of tert-butyl 3-benzyloxy-10,11-dihydropyrazino[1',2':1,2]imidazo[4,5-c]quinoline-9(8H)-carboxylate (1.0 g, 2.3 mmol) in chloroform (15 mL), and the reaction was stirred for 30 minutes. Ammonium hydroxide (5 mL), and the reaction was stirred for five minutes before the rapid addition of p-toluenesulfnyl chloride (0.4865 g, 2.55 mmol). The reaction was stirred overnight at ambient temperature. The organic layer was separated and concentrated under reduced pressure. The residue was purified by normal phase prep HPLC on silica gel (eluting with 2 N ammonia in methanol/chloroform in a 42-minute gradient from 0:100 to 5:95) to provide 550 mg of tert-butyl 6-amino-3-benzyloxy-10,11-dihydropyrazino[1',2':1,2]imidazo[4,5-c]quinoline-9(8H)-carboxylate.

Part J

Trifluoroacetic acid (10 mL of a 10% solution in dichloromethane) was added to tert-butyl 6-amino-3-benzyloxy-10,11-dihydropyrazino[1',2':1,2]imidazo[4,5-c]quinoline-9(8H)-carboxylate (0.550 g, 1.23 mmol), and the reaction was stirred at ambient temperature overnight. The solvent was removed under reduced pressure, and the residue was treated with hydrogen chloride (4 N in 1,4-dioxane). The solvent was removed under reduced pressure, and the residue was dissolved in methanol. Ammonia gas was bubbled through the resulting solution for 15 minutes, and then the solvent was removed under reduced pressure. The residue was dried overnight under vacuum to provide 3-benzyloxy-8,9,10,11-tetrahydropyrazino[1',2':1,2]imidazo[4,5-c]quinolin-6-amine in a crude mixture, which was used in the next step without purification.

Part K

Triethylamine (498 mg, 4.92 mmol) and methanesulfonyl chloride (156 mg, 1.36 mmol) were sequentially added to a solution of the material from Part J in DMF (5 mL), and the mixture was stirred at ambient temperature overnight. The solvent was removed under reduced pressure, and the residue was purified by normal phase prep HPLC (eluting with 10% ammonium hydroxide in methanol/dichloromethane in a gradient from 0/100 to 10/90) followed by recrystallization from acetonitrile to provide 108 mg of 3-(benzyloxy)-9-(methylsulfonyl)-8,9,10,11-tetrahydropyrazino[1',2':1,2]imidazo[4,5-c]quinolin-6-amine as a yellow powder, mp 266-268° C.

$^1$H NMR (300 MHz, DMSO-d6) δ 7.98 (d, J=9.0 Hz, 1H), 7.51-7.33 (m, 5H), 7.14 (d, J=2.6 Hz, 1H), 6.99 (dd, J=8.9, 2.6 Hz, 1H), 6.54 (s, 2H), 5.21 (s, 2H), 4.72-4.68 (m, 4H), 3.84 (t, J=5.4 Hz, 2H), 3.12 (s, 3H);

MS (APCI) ) m/z 424 (M+H)$^+$;

Anal. Calcd for $C_{21}H_{21}N_5O_3S$: C, 59.56; H, 5.00; N, 16.54. Found: C, 59.38; H, 4.88; N, 16.59.

Example 369

3-(Benzyloxy)-9-(methylsulfonyl)-9,10,11,12-tetrahydro-8H-[1,4]diazepino[1',2':1,2]imidazo[4,5-c]quinolin-6-amine

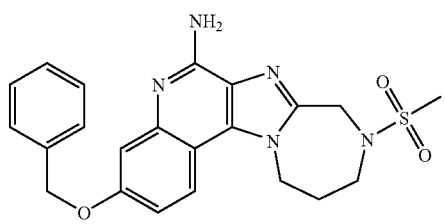

Part A

A modification of the method described in Part E of Example 367 was used to treat 7-benzyloxy-4-chloro-3-nitroquinoline (87.81 g, 279 mmol, Parts A through D of Example 367) with triethylamine (58.3 mL, 419 mmol) and tert-butyl N-(3-aminopropyl)carbamate (58.0 g, 334 mmol). The reaction was stirred overnight at ambient temperature. After filtration, the solid was washed with water and 1:1 cold 2-propanol:water. After the drying step 120.98 g of tert-butyl 3-[(7-benzyloxy-3-nitroquinolin-4-yl)amino]propylcarbamate were obtained.

Part B tert-Butyl 3-[(7-benzyloxy-3-nitroquinolin-4-yl)amino]propylcarbamate (60.0 g, 132.6 mmol) was dissolved in ethyl acetate (400 mL) and transferred to a Parr hydrogenation vessel charged with 5% platinum on carbon (15.6 g, 80 mmol, 0.03 eq). The vessel was purged with nitrogen gas and placed under hydrogen pressure (50 psi, $3.45 \times 10^5$ Pa) overnight. The catalyst was removed by filtration through a layer of CELITE filter aid, and the filter cake was rinsed with methanol and dichloromethane. The filtrate was concentrated under reduced pressure to provide 52.4 g of tert-butyl 3-[(3-amino-7-benzyloxy-quinolin-4-yl)amino]propylcarbamate.

Part C

The method described in Part G of Example 368 was used to treat tert-butyl 3-[(3-amino-7-benzyloxy-quinolin-4-yl)amino]propylcarbamate (52.4 g, 124 mmol) with triethylamine (26.0 mL, 186 mmol) and chloroacetyl chloride (10.9 mL, 136.4 mmol). After recrystallization from dichloromethane 57.2 g of tert-butyl 3-[7-benzyloxy-2-(chloromethyl)-1H-imidazo[4,5-c]quinolin-1-yl]propylcarbamate (86% pure) were obtained.

Part D

Under a nitrogen atmosphere, potassium tert-butoxide (142.7 mL of a 1 M solution in THF) was added to a solution of tert-butyl 3-[7-benzyloxy-2-(chloromethyl)-1H-imidazo[4,5-c]quinolin-1-yl]propylcarbamate (57.2 g, 118.9 mmol) in THF (142.7 mL). After the reaction was stirred at ambient temperature for ten minutes, additional potassium tert-butoxide (32 mL of a 1 M solution in THF) was added. The reaction was stirred overnight at ambient temperature and concentrated under reduced pressure. The crude reaction mixture was purified by column chromatography on silica gel (eluting with 2 N ammonia in methanol/chloroform in a 67-minute gradient from 0:100 to 3:97) and recrystallized sequentially from dichloromethane and acetonitrile to provide 26.99 g of tert-butyl 3-benzyloxy-11,12-dihydro-8H-[1,4]diazepino[1',2':1,2]imidazo[4,5-c]quinoline-9(10H)-carboxylate.

Part E

Hydrogen chloride (25 mL of a 4 N solution in 1,4-dioxane) was added to a solution of tert-butyl 3-benzyloxy-11,12-dihydro-8H-[1,4]diazepino[1',2':1,2]imidazo[4,5-c]quinoline-9(10H)-carboxylate in a 1:1 mixture of dichloromethane and diethyl ether (50 mL). The reaction was stirred overnight at ambient temperature; a precipitate formed. The precipitate was harvested via filtration and dried under reduce pressure to provide 9.66 g of 3-benzyloxy-9,10,11,12-tetrahydro-8H-[1,4]diazepino[1',2':1,2]imidazo[4,5-c]quinoline.

Part F

Triethylamine (23.4 mL, 168 mmol) and methanesulfonyl chloride (2.18 mL, 28.0 mmol) were sequentially added to a solution of the material from Part E in DMF (75 mL), and the mixture was stirred for three hours. Additional methanesulfonyl chloride (2.18 mL) was added and the mixture was stirred for one hour. The addition of sodium carbonate and heating did not increase the rate of conversion. The solvent was removed under reduced pressure, and the residue was purified by column chromatography on a COMBIFLASH system (eluting with 2 N ammonia in methanol/chloroform in a 33-minute gradient from 0:100 to 10:90) followed by recrystallization (3×) from isopropanol to provide 4.65 g of 3-(benzyloxy)-9-(methylsulfonyl)-9,10,11,12-tetrahydro-8H-[1,4]diazepino[1',2':1,2]imidazo[4,5-c]quinoline.

Part G mCPBA (2.96 g of 77% purity, 13.2 mmol) was added to a solution of 3-(benzyloxy)-9-(methylsulfonyl)-9,10,11,12-tetrahydro-8H-[1,4]diazepino[1',2':1,2]imidazo[4,5-c]quinoline (4.648 g, 11 mmol) in chloroform (20 mL), and the reaction was stirred for 10 minutes. Additional mCPBA (1.5 g) was added and the reaction was monitored for disappearance of the starting substrate by thin-layer chromatography (TLC). Ammonium hydroxide (20 mL) was then added and the reaction was stirred for five minutes before the rapid addition of p-toluenesulfonyl chloride (2.31 g, 12.1 mmol). The reaction was stirred overnight at ambient temperature. The organic layer was separated, washed with ammonium hydroxide, dried over magnesium sulfate, and concentrated under reduced pressure. The residue was purified by column chromatography on silica gel (eluting with 2 N ammonia in methanol/chloroform in a 43-minute gradient from 1:99 to 25:75) and recrystallization from isopropanol and dried in a vacuum oven at 65° C. to afford 1.1 g of 3-(benzyloxy)-9-(methylsulfonyl)-9,10,11,12-tetrahydro-8H-[1,4]diazepino[1',2':1,2]imidazo[4,5-c]quinolin-6-amine as brown crystals, mp 235-236° C.

$^1$H NMR (300 MHz, DMSO-d6) δ 8.17 (d, J=9.1 Hz, 1H), 7.50-7.32 (m, 5H), 7.13 (d, J=2.7 Hz, 1H), 6.95 (dd, J=9.0, 2.7 Hz, 1H), 6.55 (s, 2H), 5.21 (s, 2H), 4.84 (t, J=3.8 Hz, 2H), 4.79 (s, 2H), 3.71 (t, J=5.0 Hz, 2H), 2.78 (s, 3H), 2.22-2.14 (m, 2H);

$^{13}$C NMR (75 MHz, DMSO-D6) δ 157.6, 152.6, 150.0, 147.5, 137.6, 134.2, 128.8, 128.1, 127.9, 124.7, 121.7, 112.0, 109.5, 109.1, 69.4, 49.7, 46.1, 45.7, 38.3, 27.8;

MS (APCI) m/z 438 (M+H)$^+$;

Anal. Calcd for $C_{22}H_{23}N_5O_3S$: C, 60.40; H, 5.30; N, 16.01. Found: C, 60.39; H, 5.39; N, 15.98.

An additional 6.37 g of solid of 76% purity was isolated by filtration during the recrystallization and used in Examples 489-492.

Examples 370-385

A solution of 3-bromo-9-(methylsulfonyl)-9,10,11,12-tetrahydro-8H-[1,4]diazepino[1',2':1,2]imidazo[4,5-c]quinolin-6-amine (41 mg, 0.10 mmol, Example 365) in 7:3 (v/v) chloroform/methanol (2 mL) was added to a test tube. The solvent was removed by vacuum centrifugation. A boronic acid or ester selected from the table below (0.11 mmol) was added followed by n-pronanol (1.6 mL), palladium (II) acetate (0.150 mL of a 4 mg/mL solution in toluene, 0.0026 mmol), aqueous sodium carbonate (0.600 mL of 2 M, 1.2 mmol), water (0.113 mL), and triphenylphosphine (0.053 mL of a 15 mol % solution in n-propanol, 0.0078 mmol). The tube was purged with nitrogen and then heated at 80° C. overnight. Methanol (1 mL) was added followed by palladium (II) acetate, aqueous sodium carbonate, and triphenylphosphine in the amounts listed above. The tube was purged with nitrogen and then heated at 80° C. overnight.

For example 373, the solvent was removed by vacuum centrifugation. Glacial acetic acid (3 mL), THF (1 mL), and deionized water (1 mL), and the reaction was heated at 60° C. overnight. 3-Bromo-5-(tert-butyldimethylsilanyloxymethyl)pyridine was prepared according to the published procedure (Zhang, N. et al, J. Med. Chem., 45, 2832-2840 (2002)). Under a nitrogen atmosphere, a solution of 3-bromo-5-(tert-butyldimethylsilanyloxymethyl)pyridine (28.70 g, 94.94 mmol) and triisopropyl borate (26.3 mL, 114 mmol) in dry THF was cooled to −70° C. n-Butyllithium (45.6 mL, 114 mmol) was added dropwise over a period of 1.5 hours. The reaction was stirred for an additional 30 minutes and then allowed to warm to −20° C. Dilute aqueous ammonium chloride was added, and the mixture was allowed to warm to ambient temperature. The aqueous layer was separated and extracted with diethyl ether. The combined organic fractions were concentrated under reduced pressure, and methanol was added to the resulting oil. A solid formed, which was stirred with water for two days, isolated by filtration, and dried under reduced pressure to provide 18.19 g of 5-(tert-butyldimethylsilanyloxymethyl)pyridine-3-boronic acid as a white solid.

For each of Examples 370 through 385, the product from the coupling reaction was dissolved in 1N hydrochloric acid (3 mL) to adjust to pH 5-7 and passed through a Waters OASIS Sample Extractions Cartridge MCX (6 cc) optionally using light nitrogen pressure. The cartridge was washed with methanol (5 mL) optionally using light nitrogen pressure and transferred to a clean test tube. A solution of 1% ammonia in methanol (2×5 mL) was then passed through the cartridge optionally using light nitrogen pressure, and the basic solution was collected and concentrated.

Each compound was purified by prep HHLC using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the boronic acid or ester used for each example, the structure of the resulting compound, and the observed accurate mass for the isolated trifluoroacetate salt.

Examples 370-385

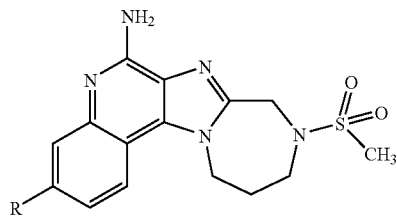

| Example | Reagent | R | Measured Mass (M + H) |
|---|---|---|---|
| 370 | Furan-3-boronic acid | 3-furyl | 398.1264 |
| 371 | (2-Hydroxyphenyl)boronic acid | 2-hydroxyphenyl | 424.1456 |
| 372 | 2-Methoxyphenylboronic acid | 2-methoxyphenyl | 438.1566 |
| 373 | 5-(tert-Butyldimethylsilanyloxymethyl)pyridine-3-boronic acid | 5-(hydroxymethyl)pyridin-3-yl | 439.1526 |
| 374 | 2-Chlorophenylboronic acid | 2-chlorophenyl | 442.1070 |
| 375 | 4-(N,N-Dimethylamino)phenylboronic acid | 4-(dimethylamino)phenyl | 451.1943 |
| 376 | 3-Ethoxyphenylboronic acid | 3-ethoxyphenyl | 452.1750 |
| 377 | (2-Acetylaminophenyl)boronic acid | 2-acetamidophenyl | 465.1722 |

-continued

| Example | Reagent | R | Measured Mass (M + H) |
|---------|---------|---|-----------------------|
| 378 | [3-(Hydroxypropyl)phenyl]boronic acid | | 466.1880 |
| 379 | 3,4-Dimethoxyphenylboronic acid | | 468.1718 |
| 380 | 3-(N,N-Dimethylaminocarbonyl)phenylboronic acid | | 479.1856 |
| 381 | 4-(4,4,5,5-Tetramethyl-1,3,2-dioxaborolan-2-yl)-1H-pyrzole | | 398.1390 |
| 382 | 4-(Cyclopropylaminocarbonyl)phenylboronic acid | | 491.1838 |
| 383 | 3-(N-Isopropylaminocarbonyl)phenylboronic acid | | 493.2057 |
| 384 | 3-(N-Propylaminocarbonyl)phenylboronic acid | | 493.1985 |
| 385 | 3-(Pyrrolidine-1-carbonyl)phenylboronic acid | | 505.1983 |

Examples 386-398

A modification of the method described in Examples 371-386 was followed using 3-bromo-9-(methylsulfonyl)-8,9,10,11-tetrahydropyrazino[1',2':1,2]imidazo[4,5-c]quinolin-6-amine (39 mg, 0.1 mmol, Example 367) in lieu of 3-bromo-9-(methylsulfonyl)-9,10,11,12-tetrahydro-8H-[1,4]diazepino[1',2':1,2]imidazo[4,5-c]quinolin-6-amine. The reactions were heated overnight only once. Each compound was purified on a Waters OASIS Sample Extractions Cartridge MCX followed by prep HPLC as described in Examples 370-385. The table below shows the boronic acid or ester used for each example, the structure of the resulting compound, and the observed accurate mass for the isolated trifluoroacetate salt.

Examples 386-398

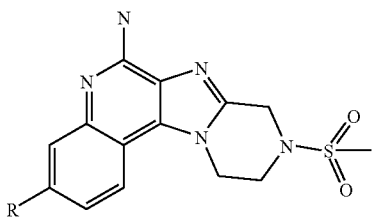

| Example | Reagent | R | Measured Mass (M + H) |
|---|---|---|---|
| 386 | Phenylboronic acid | phenyl | 394.1363 |
| 387 | Pyridine-3-boronic acid | pyridin-3-yl | 395.1311 |
| 388 | Pyridine-4-boronic acid | pyridin-4-yl | 395.1287 |
| 389 | Thiophene-3-boronic acid | thiophen-3-yl | 400.0939 |
| 390 | 3-Methylphenylboronic acid | 3-methylphenyl | 408.1512 |
| 391 | 4-Methylphenylboronic acid | 4-methylphenyl | 408.1523 |
| 392 | o-Tolylboronic acid | 2-methylphenyl | 408.1462 |
| 393 | 2,6-Dimethylphenylboronic acid | 2,6-dimethylphenyl | 422.1665 |

-continued

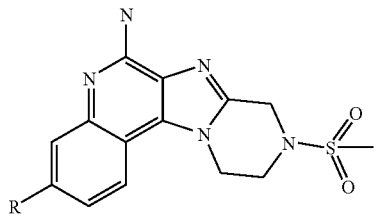

| Example | Reagent | R | Measured Mass (M + H) |
|---|---|---|---|
| 394 | 3,5-Dimethylphenylboronic acid | 3,5-dimethylphenyl | 422.1659 |
| 395 | 4-Methoxyphenylboronic acid | 4-methoxyphenyl | 424.1437 |
| 396 | (2-Hydroxymethylphenyl)boronic acid dehydrate | 2-(hydroxymethyl)phenyl | 424.1472 |
| 397 | 2-Methoxyphenylboronic acid | 2-methoxyphenyl | 424.1464 |
| 398 | 2,4-Difluorophenylboronic acid | 2,4-difluorophenyl | 430.1167 |

Examples 399-424

Hydrogen chloride (20 mL of a 4 N solution in 1,4-dioxane) and methanol (20 mL) were added to tert-butyl 6-amino-3-benzyloxy-10,11-dihydropyrazino[1',2':1,2]imidazo[4,5-c]quinoline-9(8H)-carboxylate (4.45 g, 9.98 mmol, prepared by the methods described in Example 368 Parts A through I), and the reaction was stirred at ambient temperature overnight. A precipitate was present and was isolated by filtration and washed with cold methanol. The solid was then recrystallized from methanol, isolated by filtration, washed with diethyl ether, and dried overnight under vacuum at 65° C. to provide 3.89 g of 3-benzyloxy-8,9,10,11-tetrahydropyrazino[1',2':1,2]imidazo[4,5-c]quinolin-6-amine hydrochloride as a white solid.

Part B

A reagent (0.11 mmol) indicated in the table below was added to a solution of 8,9,10,11-tetrahydropyrazino[1',2':1,2]imidazo[4,5-c]quinolin-6-amine hydrochloride (38 mg, 0.0995 mmol) and triethylamine (0.070 mL, 0.50 mmol) in pyridine (1 mL) in a test tube. The test tube was capped and shaken overnight at ambient temperature. Two drops of deionized water were added to each test tube, and the solvent was removed by vacuum centrifugation. The compounds were purified by prep HPLC according to the method described in Examples 370-385. The table below shows the acid chloride, sulfonyl chloride, isocyanate, or carbamoyl chloride used for each example, the structure of the resulting compound, and the observed accurate mass for the isolated trifluoroacetate salt.

Examples 399-424
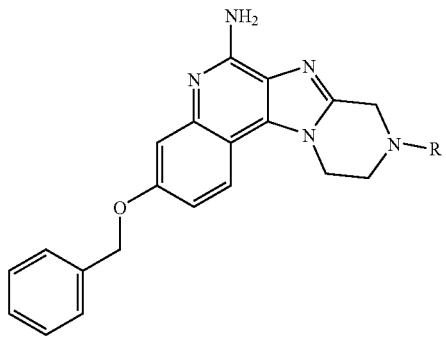
| Example | Reagent | R | Measured Mass (M + H) |
|---|---|---|---|
| 399 | None | –H | 346.1659 |
| 400 | Pentanoyl chloride | -C(O)CH₂CH₂CH₂CH₃ | 430.2242 |
| 401 | Benzoyl chloride | -C(O)Ph | 450.1914 |
| 402 | Acetyl chloride | -C(O)CH₃ | 388.1769 |
| 403 | Methyl chloroformate | -C(O)OCH₃ | 404.1718 |
| 404 | Cyclopropanecarbonyl chloride | -C(O)-cyclopropyl | 414.1932 |
| 405 | Butyryl chloride | -C(O)CH₂CH₂CH₃ | 416.2075 |
| 406 | Cyclobutanecarbonyl chloride | -C(O)-cyclobutyl | 428.2071 |

-continued
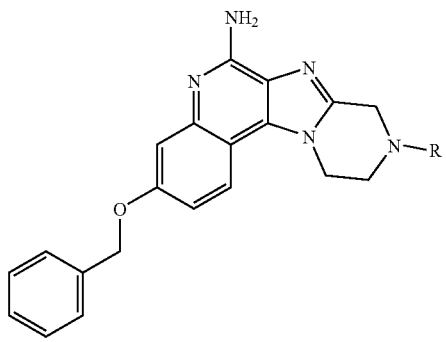
| Example | Reagent | R | Measured Mass (M + H) |
|---|---|---|---|
| 407 | 3-Chlorobenzoyl chloride | 3-chlorophenyl-C(O)– | 484.1529 |
| 408 | 4-Chlorobenzoyl chloride | 4-chlorophenyl-C(O)– | 484.1533 |
| 409 | Isonicotinoyl chloride hydrochloride | pyridin-4-yl-C(O)– | 451.1872 |
| 410 | 3-Dimethylaminobenzoyl chloride | 3-(dimethylamino)phenyl-C(O)– | 493.2340 |
| 411 | 2-Naphthoyl chloride | naphthalen-2-yl-C(O)– | 500.2072 |
| 412 | Methanesulfonyl chloride | –S(O)$_2$CH$_3$ | 424.1447 |

-continued
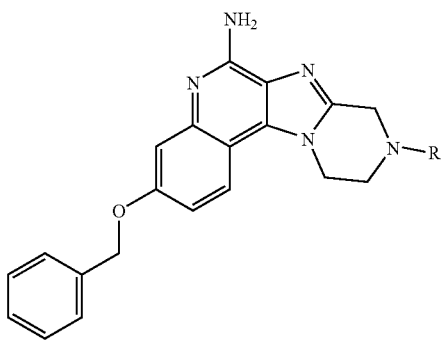
| Example | Reagent | R | Measured Mass (M + H) |
|---|---|---|---|
| 413 | Ethanesulfonyl chloride | 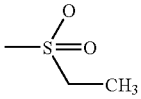 | 438.1605 |
| 414 | Methyl isocyanate | 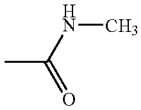 | 403.1895 |
| 415 | Ethyl isocyanate | 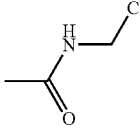 | 417.2047 |
| 416 | Isopropyl isocyanate | 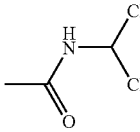 | 431.2183 |
| 417 | Phenyl isocyanate | 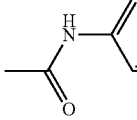 | 465.2010 |
| 418 | 3-Methoxyphenyl isocyanate | 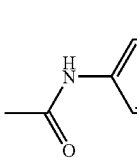 | 495.2148 |

-continued

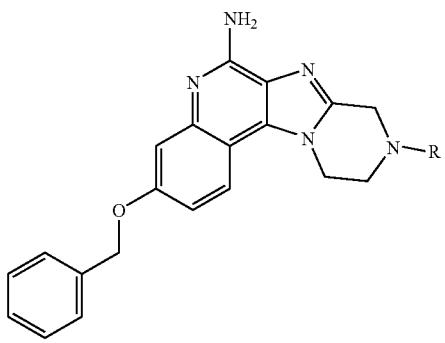

| Example | Reagent | R | Measured Mass (M + H) |
|---|---|---|---|
| 419 | 3-Chlorophenyl isocyanate | *3-chlorophenyl carbamoyl* | 499.1616 |
| 420 | 3-Acetylphenyl isocyanate | *3-acetylphenyl carbamoyl* | 507.2122 |
| 421 | N,N-Dimethylcarbamoyl chloride | *N,N-dimethylcarbamoyl* | 417.2033 |
| 422 | N,N-Dimehylthiocarbamoyl chloride | *N,N-dimethylthiocarbamoyl* | 433.1782 |
| 423 | 4-Morpholinylcarbonyl chloride | *4-morpholinylcarbonyl* | 459.2137 |
| 424 | N-Methyl-N-Phenylcarbamoyl chloride | *N-methyl-N-phenylcarbamoyl* | 479.2176 |

Examples 425-434

Potassium carbonate (55 mg, 0.40 mmol) was added to a test tube. A solution of 8,9,10,11-tetrahydropyrazino[1',2':1,2]imidazo[4,5-c]quinolin-6-amine hydrochloride (35 mg, 0.091 mmol) in anhydrous DMF (1 mL) was then added to the tube followed by an alkylating agent (0.11 mmol) from the table below. The tube was capped, shaken overnight at ambient temperature, and filtered. The filtrate was concentrated under reduced pressure, and the residue was purified by prep HPLC according to the method described in Examples 370-385. The table below shows the alkylating agent used for each example, the structure of the resulting compound, and the observed accurate mass for the isolated trifluoroacetate salt.

Examples 425-434

| Example | Reagent | R | Measured Mass (M + H) |
|---|---|---|---|
|  | None | —H | 346.1648 |
| 425 | Benzyl bromide | 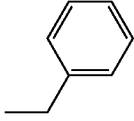 | 436.2146 |
| 426 | 1-Bromopropane | 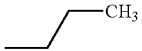—CH$_3$ | 388.2144 |
| 427 | (Bromomethyl)cyclopropane | 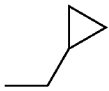 | 400.2142 |
| 428 | 2-Bromoethyl methyl ether | 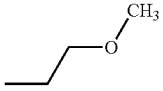 | 404.2107 |
| 429 | Iodomethane | —CH$_3$ | 360.1815 |
| 430 | alpha-Bromo-m-xylene | —CH$_3$ | 450.2265 |
| 431 | alpha-Bromo-p-xylene | 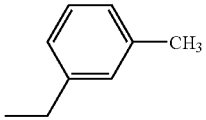 | 450.2272 |

-continued

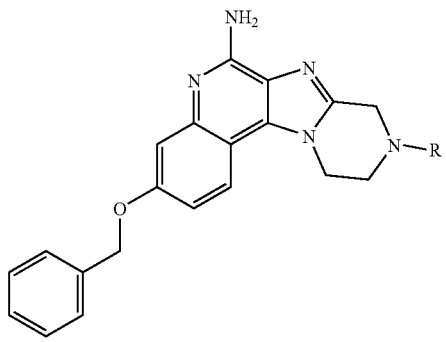

| Example | Reagent | R | Measured Mass (M + H) |
|---|---|---|---|
| 432 | 1-Iodo-3-methylbutane | —CH₂CH₂CH(CH₃)CH₃ | 416.2420 |
| 433 | 3-Methoxybenzyl bromide | 3-methoxybenzyl | 466.2237 |
| 434 | 3-(Trifluoromethoxy)benzyl bromide | 3-(trifluoromethoxy)benzyl | 520.1960 |

Examples 435-450

Part A

The methods described in Part I of Example 368 were used to treat tert-butyl 3-benzyloxy-11,12-dihydro-8H-[1,4]diazepino[1',2':1,2]imidazo[4,5-c]quinoline-9(10H)-carboxylate (5.52 g, 12.4 mmol, Example 369 Parts A through D) with mCPBA (4.17 g of 77% purity, 18.6 mmol) followed by ammonium hydroxide (25 mL) and p-toluenesulfonyl chloride (2.6 g, 13.7 mmol) and purify the final compound to provide 2.07 g of tert-butyl 6-amino-3-benzyloxy-11,12-dihydro-8H-[1,4]diazepino[1',2':1,2]imidazo[4,5-c]quinoline-9(10H)-carboxylate.

Part B

Trifluoroacetic acid (50 mL of a 10% solution in dichloromethane) was added to tert-butyl 6-amino-3-benzyloxy-11,12-dihydro-8H-[1,4]diazepino[1',2':1,2]imidazo[4,5-c]quinoline-9(10H)-carboxylate (2.07 g, 4.50 mmol), and the reaction was stirred at ambient temperature overnight. The solvent was removed under reduced pressure, and the residue was recrystallized from methanol to provide 2.2 g of 3-benzyloxy-9,10,11,12-tetrahydro-8H-[1,4]diazepino[1',2':1,2]imidazo[4,5-c]quinolin-6-amine trifluoroacetate.

Part C

A reagent (0.12 mmol) indicated in the table below was added to a solution of 3-benzyloxy-9,10,11,12-tetrahydro-8H-[1,4]diazepino[1',2':1,2]imidazo[4,5-c]quinolin-6-amine trifluoroacetate (36 mg, 0.10 mmol) and N,N-diisopropylethylamine (0.070 mL, 0.40 mmol) in anhydrous DMF (1 mL) in a test tube. The test tube was capped and shaken overnight. The solvent was removed by vacuum centrifugation. The compound was purified by prep HPLC using the method described in Examples 370-385. The table below shows the acid chloride, sulfonyl chloride, isocyanate, or carbamoyl chloride used for each example, the structure of the resulting compound, and the observed accurate mass for the isolated trifluoro acetate salt.

Examples 435-450
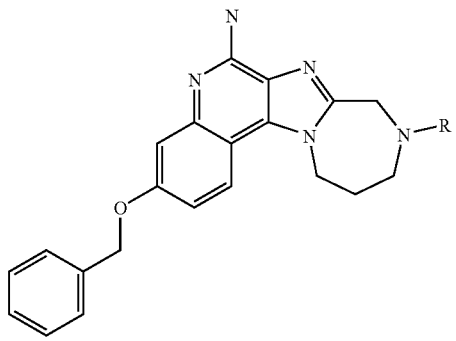
| Example | Reagent | R | Measured Mass (M + H) |
|---|---|---|---|
| 435 | None | –H | 360.1842 |
| 436 | Benzoyl chloride | ![benzoyl] | 464.2120 |
| 437 | Cyclohexanecarbonyl chloride | ![cyclohexanecarbonyl] | 470.2586 |
| 438 | Acetyl chloride | ![acetyl] | 402.1971 |
| 439 | Methyl chloroformate | ![methyl chloroformate] | 418.1903 |
| 440 | Cyclopropanecarbonyl chloride | ![cyclopropanecarbonyl] | 428.2110 |
| 441 | m-Toluoyl chloride | ![m-toluoyl] | 478.2238 |
| 442 | Hydrocinnamoyl chloride | ![hydrocinnamoyl] | 492.2409 |

-continued

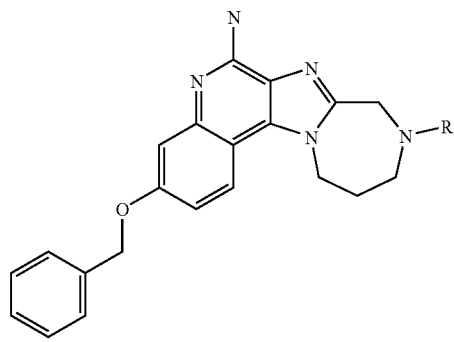

| Example | Reagent | R | Measured Mass (M + H) |
|---|---|---|---|
| 443 | 3-Methoxybenzoyl chloride | 3-methoxybenzoyl group | 494.2221 |
| 444 | 2-Naphthoyl chloride | 2-naphthoyl group | 514.2272 |
| 445 | Ethanesulfonyl chloride | ethylsulfonyl group | 452.1761 |
| 446 | Dimethylsulfamoyl chloride | N,N-dimethylsulfamoyl group | 467.1874 |
| 447 | Methyl isocyanate | N-methylcarbamoyl group | 417.2078 |
| 448 | Cyclohexyl isocyanate | N-cyclohexylcarbamoyl group | 485.2679 |
| 449 | N,N-Dimethylcarbamoyl chloride | N,N-dimethylcarbamoyl group | 431.2229 |
| 450 | N,N-Dimethylthiocarbamoyl chloride | N,N-dimethylthiocarbamoyl group | 447.1956 |

Examples 451-467

Part A

Hydrogen chloride (20 mL of 4 N in 1,4-dioxane) was added to a solution of tert-butyl 6-amino-3-benzyloxy-11,12-dihydro-8H-[1,4]diazepino[1',2':1,2]imidazo[4,5-c]quinolin-9(10H)-carboxylate (3.89 g, 8.46 mmol, prepared as described in Part A of Examples 435-450) in dichloromethane (50 mL), and the reaction was stirred at ambient temperature for one hour. Diethyl ether was added, and a precipitate formed. The precipitate was isolated by filtration and dried in a vacuum oven at 65° C. to provide 3.52 g of 3-benzyloxy-9,10,11,12-tetrahydro-8H-[1,4]diazepino[1',2':1,2]imidazo[4,5-c]quinolin-6-amine dihydrochloride.

Part B

A reagent (0.11 mmol) indicated in the table below was added to a solution of 3-benzyloxy-9,10,11,12-tetrahydro-8H-[1,4]diazepino[1',2':1,2]imidazo[4,5-c]quinolin-6-amine dihydrochloride (42 mg, 0.098 mmol) and N,N-diisopropylethylamine (0.070 mL, 0.40 mmol) in anhydrous DMF (1 mL) in a test tube. The test tube was capped and shaken overnight. Two drops of water were added, and the solvent was removed by vacuum centrifugation. The compound was purified by prep HPLC using the method described in Examples 370-385. The table below shows the acid chloride, sulfonyl chloride, isocyanate, or carbamoyl chloride used for each example, the structure of the resulting compound, and the observed accurate mass for the isolated trifluoroacetate salt.

Examples 451-467

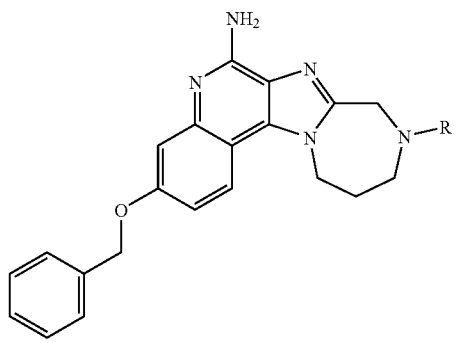

| Example | Reagent | R | Measured Mass (M + H) |
|---|---|---|---|
|  | None | —H | 360.1861 |
| 451 | Propionyl chloride | CH2CH3 | 416.2085 |
| 452 | Butyryl chloride | CH2CH2CH3 | 430.2271 |
| 453 | Ethyl chloroformate | OCH2CH3 | 432.2064 |
| 454 | Methoxyacetyl chloride | CH2OCH3 | 432.2014 |
| 455 | Cyclobutanecarbonyl chloride | -cyclobutyl | 442.2214 |

-continued
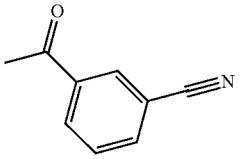
| Example | Reagent | R | Measured Mass (M + H) |
|---|---|---|---|
| 456 | 3-Cyanobenzoyl chloride | 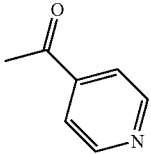 | 489.2009 |
| 457 | Isonicotinoyl chloride hydrochloride | 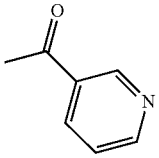 | 465.2044 |
| 458 | Nicotinoyl chloride hydrochloride | 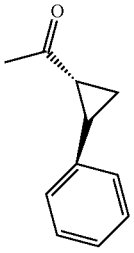 | 465.2051 |
| 459 | trans-2-Phenyl-1-cyclopropanecarbonyl chloride | 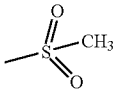 | 504.2393 |
| 460 | Methanesulfonyl chloride | 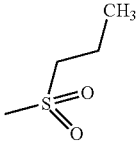 | 438.1577 |
| 461 | 1-Propanesulfonyl chloride | | 466.1910 |

-continued
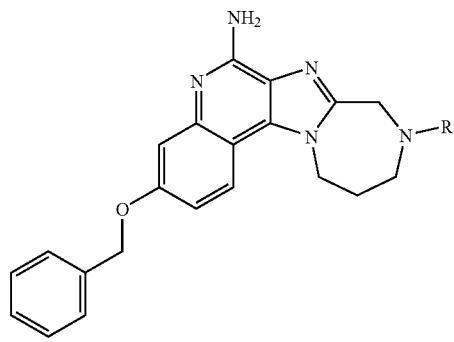
| Example | Reagent | R | Measured Mass (M + H) |
|---|---|---|---|
| 462 | 1-Butanesulfonyl chloride | -S(=O)(=O)-CH2CH2CH2-CH3 | 480.2042 |
| 463 | 3-Methoxybenzenesulfonyl chloride | 3-methoxyphenyl-S(=O)(=O)- | 530.1879 |
| 464 | 3-Chlorobenzenesulfonyl chloride | 3-chlorophenyl-S(=O)(=O)- | 534.1348 |
| 465 | Methyl isothiocyanate | -C(=S)-NH-CH3 | 433.1771 |
| 466 | Phenyl isocyanate | -C(=O)-NH-phenyl | 479.2170 |
| 467 | 4-Methyl-1-piperazinecarbonyl chloride | -C(=O)-(4-methylpiperazin-1-yl) | 486.2587 |

Examples 468-480

An aldehyde or ketone (0.12-0.13 mmol) indicated in the table below was added to a solution of 3-benzyloxy-9,10,11,12-tetrahydro-8H-[1,4]diazepino[1',2':1,2]imidazo[4,5-c]quinolin-6-amine trifluoroacetate (35.6 mg, 0.0931 mmol) in anhydrous DMF (1 mL) in a test tube. The test tube was capped and shaken for 30 minutes. Borane-pyridine complex (13 μL, 0.104 mmol) was added, and the reaction was shaken overnight.

For examples 476-480, additional ketone (0.12-0.13 mmol) was added, and the reaction was shaken for 10 minutes. Additional borane-pyridine complex (13 μL, 0.104 mmol) was added, and the reaction was shaken for six hours.

For each reaction, the solvent was removed by vacuum centrifugation. The compounds were purified by prep HPLC according to the method described in Examples 370-385. The table below shows aldehyde or ketone used for each example, the structure of the resulting compound, and the observed accurate mass for the isolated trifluoroacetate salt.

Example 468-480

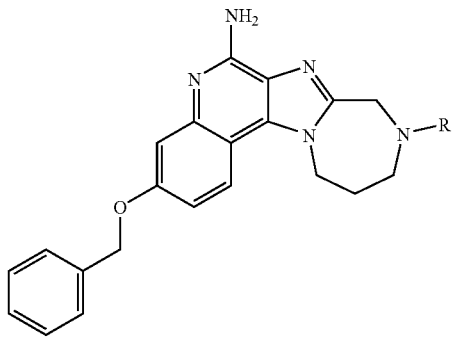

| Example | Reagent | R | Measured Mass (M + H) |
|---|---|---|---|
|  | None | —H | 360.1839 |
| 468 | 2-Hydroxyacetaldehyde | —CH₂CH₂OH | 404.2066 |
| 469 | Butyraldehyde | —CH₂CH₂CH₂CH₃ | 416.2430 |
| 470 | Isobutyraldehyde | —CH₂CH(CH₃)₂ | 416.2477 |
| 471 | Isovaleradehyde | —CH₂CH₂CH(CH₃)₂ | 430.2608 |
| 472 | Nicotinaldehyde | —CH₂(3-pyridyl) | 451.2253 |
| 473 | Phenylacetaldehyde | —CH₂CH₂Ph | 464.2458 |

-continued

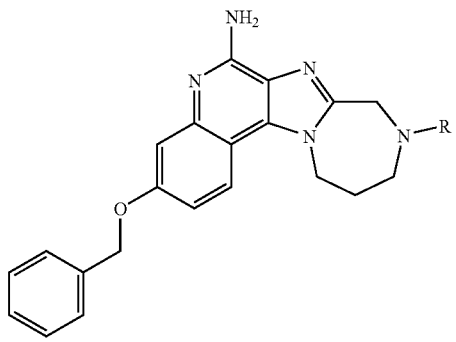

| Example | Reagent | R | Measured Mass (M + H) |
|---|---|---|---|
| 474 | 3,4-Difluorobenzaldehyde | (3,4-difluorobenzyl) | 486.2124 |
| 475 | Quinoline-3-carboxaldehyde | (quinolin-3-ylmethyl) | 501.2393 |
| 476 | Hydroxyacetone | (2-hydroxy-1-methylethyl, CH₃, OH) | 418.2253 |
| 477 | Dihydroxyacetone | (1,3-dihydroxypropan-2-yl) | 434.2203 |
| 478 | 1-Methyl-4-piperidone | (1-methylpiperidin-4-yl) | 457.2745 |
| 479 | 1-Acetyl-4-piperidone | (1-acetylpiperidin-4-yl) | 485.2658 |
| 480 | 1-Benzyl-4-piperidone | (1-benzylpiperidin-4-yl) | 533.3030 |

Examples 481-488

The methods described in Examples 425-434 were used to treat 3-benzyloxy-9,10,11,12-tetrahydro-8H-[1,4]diazepino[1',2':1,2]imidazo[4,5-c]quinolin-6-amine dihydrochloride (43 mg, 0.10 mmol) with potassium carbonate (55 mg, 0.40 mmol) and an alkylating agent (0.11 mmol) from the table below and purify the final compound. The table below shows the alkylating agent used for each example, the structure of the resulting compound, and the observed accurate mass for the isolated trifluoroacetate salt.

Examples 481-488

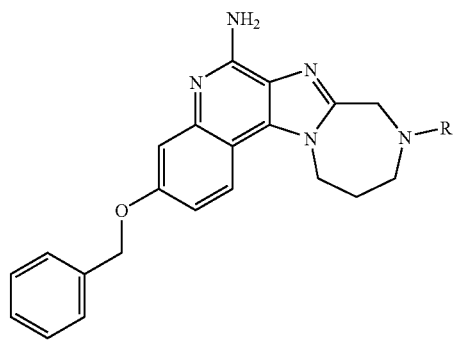

| Example | Reagent | R | Measured Mass (M + H) |
|---|---|---|---|
| 481 | (Bromomethyl)cyclopropane | cyclopropylmethyl | 414.2291 |
| 482 | 4-(Bromomethyl)pyridine hydrobromide | 4-pyridylmethyl | 451.2216 |
| 483 | 1-(3-Bromopropyl)pyrrole | 3-(pyrrol-1-yl)propyl | 467.2535 |
| 484 | Benzyl 3-bromopropyl ether | 3-(benzyloxy)propyl | 508.2660 |
| 485 | Benzyl bromide | benzyl | 450.2270 |
| 486 | 3-Chlorobenzyl bromide | 3-chlorobenzyl | 484.1869 |
| 487 | 4-Chlorobenzyl bromide | 4-chlorobenzyl | 484.1877 |
| 488 | 2-(Bromomethyl)naphthalene | naphthalen-2-ylmethyl | 500.2404 |

Examples 489-492

Part A 3-(Benzyloxy)-9-(methylsulfonyl)-9,10,11,12-tetrahydro-8H-[1,4]diazepino[1',2':1,2]imidazo[4,5-c]quinolin-6-amine, (6.37 g, 14.56 mmol) prepared as described in Example 369, was dissolved in methanol (150 mL) and transferred to a hydrogenation vessel charged with 10% palladium on carbon (12.4 g, 116 mmol). The vessel was purged with nitrogen gas and placed under hydrogen pressure (50 psi, $3.45 \times 10^5$ Pa) and shaken for 3 days at ambient temperature. The catalyst was removed by filtration. The filtrate was concentrated under reduced pressure, and the residue crystallized from isopropanol. The material was purified by column chromatography on silica gel (eluting with 2 N ammonia in methanol/chloroform in a 47-minute gradient from 5:95 to 50:50) and crystallized from isopropanol to provide 1.15 g of 6-amino-9-(methylsulfonyl)-9,10,11,12-tetrahydro-8H-[1,4]diazepino[1',2':1,2]imidazo[4,5-c]quinolin-3-ol.

Part B

Potassium carbonate (55 mg, 0.40 mmol) was added to a test tube. A solution of 6-amino-9-(methylsulfonyl)-9,10,11,12-tetrahydro-8H-[1,4]diazepino[1∝,2':1,2]imidazo[4,5-c]quinolin-3-ol (36 mg, 0.10 mmol) in anhydrous N,N-dimethylacetamide (DMA) (1 mL) was then added to the tube followed by an alkylating agent (0.15 mmol) from the table below. The tube was capped, shaken overnight at ambient temperature, heated at 50° C. over a second night, and filtered. The filtrate was concentrated under reduced pressure, and the residue was purified by prep HPLC according to the method described in Examples 370-385. The table below shows the alkylating agent used for each example, the structure of the resulting compound, and the observed accurate mass for the isolated trifluoroacetate salt.

Examples 493-494

Part A 3-(Benzyloxy)-9-(methylsulfonyl)-8,9,10,11-tetrahydropyrazino[1',2':1,2]imidazo[4,5-c]quinolin-6-amine, (3.34 g, 10.0 mmol) prepared as described in Example 368, was dissolved in a mixture of methanol (100 mL) and dichloromethane (100 mL) and transferred to a hydrogenation vessel charged with 10% palladium on carbon (5 g, 47 mmol). The vessel was placed under hydrogen pressure (50 psi, $3.45 \times 10^5$ Pa) and shaken for two days at ambient temperature. An analysis by LC/MS indicated the presence of starting material. The catalyst was removed by filtration through a layer of CELITE filter aid, and the filtrate was placed under hydrogen pressure (50 psi, $3.45 \times 10^5$ Pa) again for two days in the presence of 10% palladium on carbon (5 g, 47 mmol). The catalyst was removed by filtration through a layer of CELITE filter aid, and the filtrate was concentrated under reduced pressure. The residue (560 mg) was combined with material from another run to provide 1.19 g of 6-amino-9-(methylsulfonyl)-8,9,10,11-tetrahydropyrazino[1',2':1,2]imidazo[4,5-c]quinolin-3-ol.

Part B

A modification of the method described in Examples 489-492 was used to treat 6-amino-9-(methylsulfonyl)-8,9,10,11-tetrahydropyrazino[1',2':1,2]imidazo[4,5-c]quinolin-3-ol (33 mg, 0.10 mmol) with potassium carbonate (55 mg, 0.40 mmol) and an alkylating agent (0.13 mmol) from the table below. DMF was used as in lieu of DMA, and heating at 50° C. was carried out for four hours. Each product was purified by prep HPLC according to the method described in Examples 370-385. The table below shows the alkylating agent used for each example, the structure of the resulting compound, and the observed accurate mass for the isolated trifluoroacetate salt.

Examples 489-492

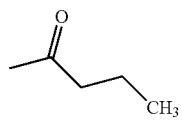

| Example | Reagent | R | Measured Mass (M + H) |
|---|---|---|---|
| 489 | None | H— | 348.1132 |
| 490 | Iodomethane | H₃C— | 362.1277 |
| 491 | 1-(3-Bromopropyl)pyrrole | (pyrrol-1-yl)propyl— | 455.1890 |
| 492 | 4-Chlorobenzyl bromide | 4-chlorobenzyl— | 472.1219 |

Examples 493-494

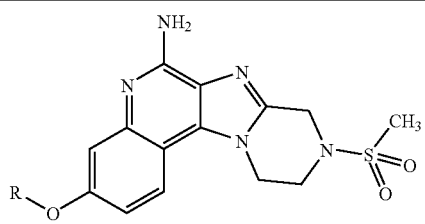

| Example | Reagent | R | Measured Mass (M + H) |
|---|---|---|---|
| 493 | 2-Bromo-4'-Methoxyacetophenone | H₃C−O−C₆H₄−C(=O)−CH₂− | 482.1505 |
| 494 | 4-(Trifluoromethyl)benzyl Bromide | 4-CF₃−C₆H₄−CH₂− | 492.1306 |

Example 495

3,4-Dimethyl-9-(methylsulfonyl)-7,8,9,10-tetrahydro-6H-pyrido[3',4':4,5]imidazo[1,2-a][1,4]diazepin-1-amine

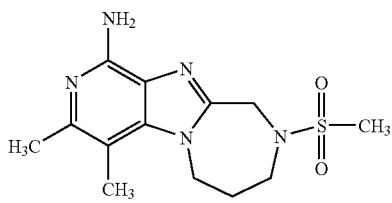

Part A tert-Butyl 3-[(3-amino-5,6-dimethyl-2-phenoxypyridin-4-yl)amino]propylcarbamate (68.8 g, 178 mmol), prepared as described in U.S. Pat. No. 6,545,016, Example 17, Parts A through C, was dissolved in chloroform (600 mL). Ethyl 2-chloroacetimidate hydrochloride (56.0 g, 354 mmol) was added to the solution and the reaction mixture was stirred at 60° C. for 72 hours. The reaction mixture was diluted with chloroform (200 mL), washed with brine (2×600 mL), and the layers were separated. The combined organics were dried over magnesium sulfate, filtered through CELITE filter aid, and concentrated under reduced pressure to afford 91.62 g of tert-butyl 3-[2-(chloromethyl)-6,7-dimethyl-4-phenoxy-1H-imidazo[4,5-c]pyridin-1-yl]propylcarbamate.

Part B tert-Butyl 3-[2-(chloromethyl)-6,7-dimethyl-4-phenoxy-1H-imidazo[4,5-c]pyridin-1-yl]propylcarbamate (90.0 g, 202 mmol) was dissolved in THF (800 mL) and dichloromethane (800 mL) and cooled to 0° C. Potassium tert-butoxide (30.0 mL of a 1 M solution in THF) was added and the reaction mixture was stirred overnight at ambient temperature and at 60° C. for two hours. Additional potassium tert-butoxide solution (30.0 mL) was added to the reaction mixture and heated at 60° C. for three hours. Additional potassium tert-butoxide solution (30.0 mL) was added to the reaction mixture and heated at 60° C. overnight. Addition of 250 mL of potassium tert-butoxide solution to the reaction mixture followed. The reaction mixture was stirred for 2.5 hours and the reaction mixture was concentrated under reduced pressure. The residue was dissolved in 800 mL of ethyl acetate and washed with brine (5×500 mL). The combined organic layers were dried over magnesium sulfate, filtered through CELITE filter aid, and concentrated under reduced pressure to afford 75.0 g of a dark brown solid. A portion of the material (44.0 g) was subjected to column chromatography on silica gel (eluting with a gradient of 1:2000 methanol in dichloromethane to 2:1:97 methanol:ammonium hydroxide:dichloromethane). The resulting material was further subjected to column chromatography on silica gel (eluting with 0.5-1:1:97.5-98 methanol:ammonium hydroxide:dichloromethane) four additional times and concentrated under reduced pressure to afford 28.92 g of tert-butyl 3,4-dimethyl-1-phenoxy-7,8-dihydro-6H-pyrido[3',4':4,5]imidazo[1,2-a][1,4]diazepine-9(10 B)-carboxylate as a light brown solid.

Part C

Ammonia (260 mL of a 7 N solution in methanol) and tert-butyl 3,4-dimethyl-1-phenoxy-7,8-dihydro-6H-pyrido[3',4':4,5]imidazo[1,2-a][1,4]diazepine-9(10H)-carboxylate (8.61 g, 21.0 mmol) were placed in a sealed glass container and heated to 170° C. overnight. The reaction mixture was cooled to ambient temperature and dissolved in ethanol (100 ml). Hydrochloric acid (45 mL, 12 M) was added to the reaction mixture and stirred at 90° C. and stirred overnight. The mixture was cooled to ambient temperature and concentrated under reduced pressure to afford 8.01 g of a dark brown material. The material was rinsed with diethyl ether and dissolved with methanol. The mixture was treated with hydrogen chloride (a 4 N solution in 1,4-dioxane) and concentrated under reduced pressure. The resulting material was slurried with diethyl ether and filtered. The filter cake was washed with diethyl ether, and the resulting solid was dried under reduced pressure. The material was slurried with hot acetonitrile and filtered to afford 6.55 g of 3,4-dimethyl-7,8,9,10-tetrahydro-6H-pyrido[3',4':4,5]imidazo[1,2-a][1,4]diazepin-1-amine dihydrochloride. Material from a separate run was used in the next step.

Part D

Methanesulfonyl chloride (198 mg, 1.73 mmol) was added to a solution of 3,4-dimethyl-7,8,9,10-tetrahydro-6H-pyrido[3',4':4,5]imidazo[1,2-a][1,4]diazepin-1-amine dihydrochloride (400 mg, 1.31 mmol) and triethylamine (350 mg, 3.46 mmol) in DMF (250 mL) and stirred overnight at ambient temperature. The reaction mixture was concentrated under reduced pressure and adsorbed onto silica gel. The material was purified by column chromatography on silica gel, concentrated under reduced pressure, dissolved in dimethyl sulfoxide (DMSO), and purified by reverse phase prep HPLC (eluting with 0.5% formic acid in water/0.5% formic acid in acetonitrile in a 10-minute gradient from 5:95 to 95:5) using a HPLC purification system obtained from Shimadzu corporation (based in Kyoto, Japan) to afford 135 mg of 3,4-dimethyl-9-(methylsulfonyl)-7,8,9,10-tetrahydro-6H-pyrido[3',4':4,5]imidazo[1,2-a][1,4]diazepin-1-amine. HRMS (EI) calcd for $C_{13}H_{19}N_5O_2S$ 310.1338, found 310.1346.

Examples 496-565

The methods described in Part C of Examples 435-450 were used to treat 3,4-dimethyl-7,8,9,10-tetrahydro-6H-pyrido[3',4':4,5]imidazo[1,2-a][1,4]diazepin-1-amine dihydrochloride (31 mg, 0.10 mmol) with N,N-diisopropylethylamine (0.057 mL, 0.33 mmol) and a reagent (0.12 mmol) indicated in the table below and purify the final compound. The table below shows the acid chloride, sulfonyl chloride, isocyanate, or carbamoyl chloride used for each example, the structure of the resulting compound, and the observed accurate mass for the isolated trifluoroacetate salt.

Examples 496-565

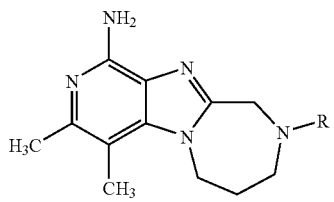

| Example | Reagent | R | Measured Mass (M + H) |
|---|---|---|---|
| 496 | Acetyl chloride | ![CH3-C(=O)-] | 274.1660 |
| 497 | Cyclopropanecarbonyl chloride | ![cyclopropyl-C(=O)-] | 300.1826 |
| 498 | Butyryl chloride | ![CH3CH2CH2-C(=O)-] | 302.1972 |
| 499 | Ethyl chloroformate | ![CH3CH2-O-C(=O)-] | 304.1783 |

-continued

| Example | Reagent | R | Measured Mass (M + H) |
|---------|---------|---|-----------------------|
| 500 | Pivaloyl chloride | | 316.2132 |
| 501 | m-Toluoyl chloride | | 350.1996 |
| 502 | 2-Thiopheneacetyl chloride | | 356.1564 |
| 503 | 3-Cyanobenzoyl chloride | | 361.1768 |
| 504 | Cinnamoyl chloride | | 362.1962 |
| 505 | Hydrocinnamoyl chloride | | 364.2146 |
| 506 | 3-Methoxybenzoyl chloride | | 366.1923 |

-continued

| Example | Reagent | R | Measured Mass (M + H) |
|---|---|---|---|
| 507 | p-Anisoyl chloride | 4-methoxybenzoyl | 366.1917 |
| 508 | 3-Chlorobenzoyl chloride | 3-chlorobenzoyl | 370.1443 |
| 509 | 4-Chlorobenzoyl chloride | 4-chlorobenzoyl | 370.1463 |
| 510 | Nicotinoyl chloride hydrochloride | nicotinoyl (pyridin-3-ylcarbonyl) | 337.1793 |
| 511 | trans-2-Phenyl-1-cyclopropanecarbonyl chloride | trans-2-phenylcyclopropanecarbonyl | 376.2150 |
| 512 | 3-Dimethylaminobenzoyl chloride | 3-(dimethylamino)benzoyl | 379.2267 |

-continued

| Example | Reagent | R | Measured Mass (M + H) |
|---|---|---|---|
| 513 | 2-Naphthoyl chloride | 2-naphthoyl | 386.1989 |
| 514 | Methyl 4-Chlorocarbonylbenzoate | 4-(methoxycarbonyl)benzoyl | 394.1897 |
| 515 | 3,4-Dimethoxybenzoyl chloride | 3,4-dimethoxybenzoyl | 396.2018 |
| 516 | 3-(Trifluoromethyl)benzoyl chloride | 3-(trifluoromethyl)benzoyl | 404.1696 |
| 517 | 3,4-Dichlorobenzoyl chloride | 3,4-dichlorobenzoyl | 404.1085 |
| 518 | 4-Biphenylcarbonyl chloride | 4-biphenylcarbonyl | 412.2153 |

-continued

| Example | Reagent | R | Measured Mass (M + H) |
|---|---|---|---|
| 519 | 3-(Trifluoromethoxy)benzoyl chloride | 3-(trifluoromethoxy)benzoyl group | 420.1664 |
| 520 | Ethanesulfonyl chloride | ethylsulfonyl | 324.1501 |
| 521 | 1-Propanesulfonyl chloride | propylsulfonyl | 338.1653 |
| 522 | Dimethylsulfamoyl chloride | dimethylsulfamoyl | 339.1638 |
| 523 | 1-Butanesulfonyl chloride | butylsulfonyl | 352.1808 |
| 524 | Trifluoromethanesulfonyl chloride | trifluoromethylsulfonyl | 364.1060 |
| 525 | Benzenesulfonyl chloride | phenylsulfonyl | 372.1515 |
| 526 | 1-Methylimidazole-4-sulfonyl chloride | 1-methylimidazol-4-ylsulfonyl | 376.1573 |

-continued

| Example | Reagent | R | Measured Mass (M + H) |
|---|---|---|---|
| 527 | 2,2,2-Trifluoroethanesulfonyl chloride | -S(O)₂-CH₂-CF₃ | 378.1219 |
| 528 | 2-Thiophenesulfonyl chloride | -S(O)₂-(2-thienyl) | 378.1049 |
| 529 | 3-Methylbenzenesulfonyl chloride | -S(O)₂-(3-methylphenyl) | 386.1676 |
| 530 | alpha-Toluenesulfonyl chloride | -S(O)₂-CH₂-phenyl | 386.1669 |
| 531 | 3-Cyanobenzenesulfonyl chloride | -S(O)₂-(3-cyanophenyl) | 397.1472 |
| 532 | beta-Styrenesulfonyl chloride | -S(O)₂-CH=CH-phenyl | 398.1616 |
| 533 | 3-Methoxybenzenesulfonyl chloride | -S(O)₂-(3-methoxyphenyl) | 402.1617 |

-continued
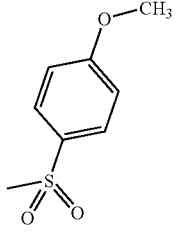
| Example | Reagent | R | Measured Mass (M + H) |
|---|---|---|---|
| 534 | 4-Methoxybenzenesulfonyl chloride | 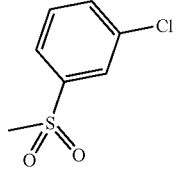 | 402.1595 |
| 535 | 3-Chlorobenzenesulfonyl chloride | 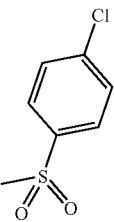 | 406.1125 |
| 536 | 4-Chlorobenzenesulfonyl chloride | 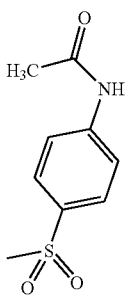 | 406.1129 |
| 537 | N-Acetylsulfanilyl chloride | 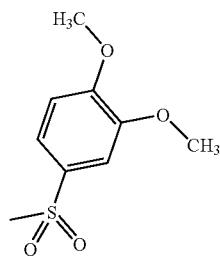 | 429.1713 |
| 538 | 3,4-Dimethoxybenzenesulfonyl chloride | | 432.1721 |

-continued

| Example | Reagent | R | Measured Mass (M + H) |
|---|---|---|---|
| 539 | 3-(Trifluoromethyl)benzenesulfonyl chloride | 3-(trifluoromethyl)phenylsulfonyl group | 440.1339 |
| 540 | 10-Camphorsulfonyl chloride | camphorsulfonyl group | 446.2263 |
| 541 | 3-(Trifluoromethoxy)benzenesulfonyl chloride | 3-(trifluoromethoxy)phenylsulfonyl group | 456.1322 |
| 542 | Methyl isocyanate | -C(=O)NH-CH$_3$ | 289.1754 |
| 543 | Ethyl isocyanate | -C(=O)NH-CH$_2$CH$_3$ | 303.1916 |
| 544 | Methyl isothiocyanate | -C(=O)NH-CH$_3$ | 305.1573 |
| 545 | Ethyl isothiocyanate | -C(=S)NH-CH$_2$CH$_3$ | 319.1732 |

-continued
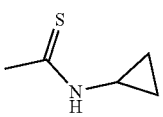
| Example | Reagent | R | Measured Mass (M + H) |
|---|---|---|---|
| 546 | Cyclopropyl isothiocyanate | 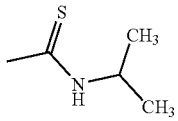 | 331.1716 |
| 547 | Isopropyl isothiocyanate | 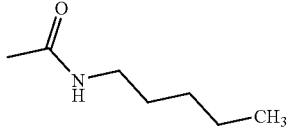 | 333.1890 |
| 548 | Pentyl isocyanate | 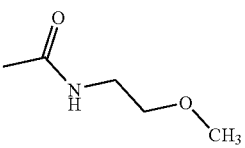 | 345.2412 |
| 549 | 2-Methoxyethyl isothiocyanate | 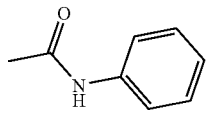 | 349.1807 |
| 550 | Phenyl isocyanate | 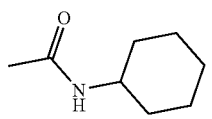 | 351.1964 |
| 551 | Cyclohexyl isocyanate | 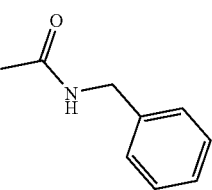 | 357.2403 |
| 552 | Benzyl isocyanate | | 365.2083 |

-continued

| Example | Reagent | R | Measured Mass (M + H) |
|---|---|---|---|
| 553 | 3-Pyridyl isothiocyanate | | 368.1655 |
| 554 | Benzoyl isocyanate | | 379.1888 |
| 555 | 2-Phenyl ethylisocyanate | | 379.2258 |
| 556 | 3-Methoxyphenyl isocyanate | | 381.2032 |
| 557 | 4-Methoxyphenyl isocyanate | | 381.2055 |
| 558 | 2-(Thien-2-yl)ethyl isocyanate | | 385.1847 |
| 559 | trans-2-Phenylcyclopropyl isocyanate | | 391.2245 |
| 560 | 3-Acetylphenyl isocyanate | | 393.2043 |

-continued

[Structure: pyrido-imidazo-diazepine core with NH2, H3C, CH3 substituents and N-R group]

| Example | Reagent | R | Measured Mass (M + H) |
|---------|---------|---|----------------------|
| 561 | 2-Morpholinoethyl isothiocyanate | -C(=S)-NH-CH2CH2-morpholine | 404.2240 |
| 562 | 3-Carbomethoxyphenyl isocyanate | -C(=O)-NH-(3-carbomethoxyphenyl) | 409.1996 |
| 563 | 3,4-Dimethoxyphenyl isocyanate | -C(=O)-NH-(3,4-dimethoxyphenyl) | 411.2150 |
| 564 | 2-Oxo-1-imidazolidinecarbonyl chloride | -C(=O)-(2-oxoimidazolidin-1-yl) | 344.1848 |
| 565 | 4-Methyl-1-piperazinecarbonyl chloride | -C(=O)-(4-methylpiperazin-1-yl) | 358.2361 |

Examples 566-610

An aldehyde or ketone (0.12 mmol) indicated in the table below was added to a solution of 3,4-dimethyl-7,8,9,10-tetrahydro-6H-pyrido[3',4':4,5]imidazo[1,2-a][1,4]diazepin-1-amine dihydrochloride (30 mg, 0.10 mmol) and N,N-diisopropylethylamine (0.052 mL, 0.30 mmol) in anhydrous DMF (2 mL) in a test tube. The test tube was capped and shaken for 30 minutes. Borane-pyridine complex (13 µL, 0.104 mmol) was added, and the reaction was shaken overnight. The solvent was removed by vacuum centrifugation. The compounds were purified by prep HPLC according to the method described in Examples 370-385. The table below shows the aldehyde or ketone used for each example, the structure of the resulting compound, and the observed accurate mass for the isolated trifluoroacetate salt.

Examples 566-610
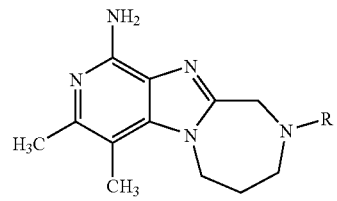
| Example | Reagent | R | Measured Mass (M + H) |
|---|---|---|---|
| 566 | Cyclopropanecarboxaldehyde | ![cyclopropylmethyl] | 286.2057 |
| 567 | Isovaleraldehyde | ![isopentyl] | 302.2336 |
| 568 | Furfural | ![furfuryl] | 312.1828 |
| 569 | Methional | ![3-(methylthio)propyl] | 320.1927 |
| 570 | Benzaldehyde | ![benzyl] | 322.2043 |
| 571 | Isonicotinaldehyde | ![4-pyridylmethyl] | 323.1975 |
| 572 | Nicotinaldehyde | ![3-pyridylmethyl] | 323.1997 |
| 573 | 1-Methyl-2-imidazolecarboxaldehyde | ![(1-methylimidazol-2-yl)methyl] | 326.2094 |

-continued
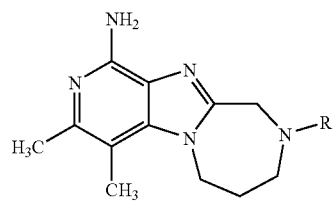
| Example | Reagent | R | Measured Mass (M + H) |
|---|---|---|---|
| 574 | 3-Cyclohexene-1-carboxaldehyde | | 326.2329 |
| 575 | 3-Thiophenecarboxaldehyde | | 328.1612 |
| 576 | Cyclohexanecarboxaldehyde | | 328.2493 |
| 577 | 2-Thiazolecarboxaldehyde | | 329.1556 |
| 578 | m-Tolualdehyde | | 336.2208 |
| 579 | o-Tolualdehyde | | 336.2192 |
| 580 | 3-Phenylpropionaldehyde | | 350.2344 |
| 581 | p-Anisaldehyde | | 352.2136 |

-continued
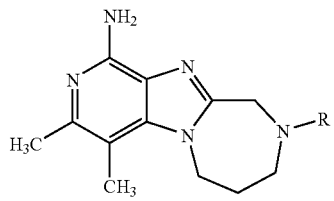
| Example | Reagent | R | Measured Mass (M + H) |
|---|---|---|---|
| 582 | 3-Methoxybenzaldehyde | 3-methoxybenzyl | 352.2128 |
| 583 | o-Anisaldehyde | 2-methoxybenzyl | 352.2133 |
| 584 | 2-Chlorobenzaldehyde | 2-chlorobenzyl | 356.1648 |
| 585 | 3-Chlorobenzaldehyde | 3-chlorobenzyl | 356.1658 |
| 586 | 4-Chlorobenzaldehyde | 4-chlorobenzyl | 356.1665 |
| 587 | Ethyl 2-formyl-1-cyclopropanecarboxylate | (2-ethoxycarbonyl-cyclopropyl)methyl | 358.2217 |
| 588 | Cuminaldehyde | 4-isopropylbenzyl | 364.2509 |

-continued
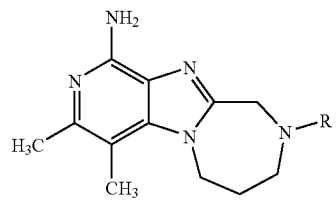
| Example | Reagent | R | Measured Mass (M + H) |
|---|---|---|---|
| 589 | 3-Phenyl butanal | (1-methyl-3-phenylpropyl) | 364.2505 |
| 590 | 3-Hydroxy-4-methoxybenzaldehyde | (3-hydroxy-4-methoxybenzyl) | 368.2104 |
| 591 | 2-Naphthaldehyde | (2-naphthylmethyl) | 372.2210 |
| 592 | 2-Quinolinecarboxaldehyde | (quinolin-2-ylmethyl) | 373.2148 |
| 593 | Quinoline-3-carboxaldehyde | (quinolin-3-ylmethyl) | 373.2153 |
| 594 | 3-Chloro-4-fluorobenzaldehyde | (3-chloro-4-fluorobenzyl) | 374.1564 |

-continued
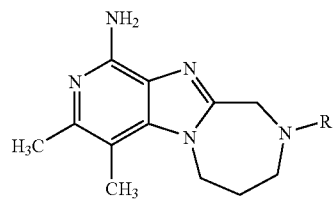
| Example | Reagent | R | Measured Mass (M + H) |
|---|---|---|---|
| 595 | 1-Methylindole-2-carboxaldehyde | 2-(1-methylindol-2-yl)ethyl | 375.2305 |
| 596 | 1-Benzothiophene-3-carbaldehyde | 2-(benzothiophen-3-yl)ethyl | 378.1757 |
| 597 | Methyl 4-formylbenzoate | 2-(4-methoxycarbonylphenyl)ethyl | 380.2109 |
| 598 | 2,4-Dimethoxybenzaldehyde | 2-(2,4-dimethoxyphenyl)ethyl | 382.2269 |
| 599 | 2,5-Dimethoxybenzaldehyde | 2-(2,5-dimethoxyphenyl)ethyl | 382.2254 |
| 600 | 2,6-Dimethoxybenzaldehyde | 2-(2,6-dimethoxyphenyl)ethyl | 382.2229 |

-continued
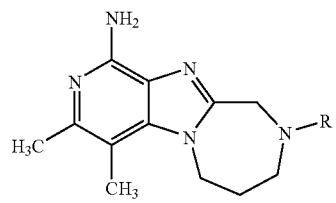
| Example | Reagent | R | Measured Mass (M + H) |
|---|---|---|---|
| 601 | 3,4-Dimethoxybenzaldehyde | 3,4-dimethoxybenzyl | 382.2260 |
| 602 | 3,5-Dimethoxybenzaldehyde | 3,5-dimethoxybenzyl | 382.2259 |
| 603 | 3,5-Dichlorobenzaldehyde | 3,5-dichlorobenzyl | 390.1262 |
| 604 | 2,3-Dichlorobenzaldehyde | 2,3-dichlorobenzyl | 390.1270 |
| 605 | 2,4-Dichlorobenzaldehyde | 2,4-dichlorobenzyl | 390.1254 |
| 606 | 2,6-Dichlorobenzaldehyde | 2,6-dichlorobenzyl | 390.1268 |
| 607 | 3,4-Dichlorobenzaldehyde | 3,4-dichlorobenzyl | 390.1260 |

-continued

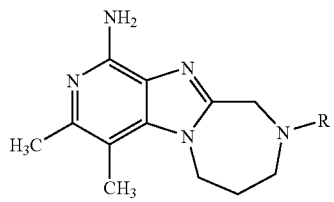

| Example | Reagent | R | Measured Mass (M + H) |
|---|---|---|---|
| 608 | Diphenylacetaldehyde | | 412.2508 |
| 609 | 4-Phenoxybenzaldehyde | | 414.2299 |
| 610 | 4-Phenylcyclohexanone | | 390.2678 |

Examples 611-644

Part A tert-Butyl 2-[(3-amino-5,6-dimethyl-2-phenoxypyridin-4-yl)amino]ethylcarbamate (17.9 g, 48.1 mmol), prepared as described in U.S. Pat. No. 6,545,016 Example 23, Parts A through C, was dissolved in chloroform (250 mL). Ethyl 2-chloroacetimidate hydrochloride (15.2 g, 96 mmol) was added to the solution and the reaction mixture was stirred at 60° C. for 5 hours. Additional ethyl 2-chloroacetimidate hydrochloride (1.9 g) was added to the reaction mixture and stirred for 0.5 hours. The reaction mixture was cooled and filtered. The filtrate was diluted with chloroform (250 mL), washed with brine (2×300 mL), and the layers were separated. The combined organics were dried over magnesium sulfate, filtered with CELITE filter aid, and concentrated under reduced pressure. The material was recrystallized and filtered from acetonitrile to yield 13.28 g of tert-butyl 2-[2-(chloromethyl)-6,7-dimethyl-4-phenoxy-1H-imidazo[4,5-c]pyridin-1-yl]ethylcarbamate as a white solid.

Part B tert-Butyl 2-[2-(chloromethyl)-6,7-dimethyl-4-phenoxy-1H-imidazo[4,5-c]pyridin-1-yl]ethylcarbamate (5.0 g, 11.6 mmol) was dissolved in THF (50 mL) and dichloromethane (50 mL) and cooled to 0° C. Potassium tert-butoxide (17.0 mL of a 1 M solution in THF) was added and the reaction mixture was heated to 60° C. and stirred for two hours. The reaction mixture was concentrated under reduced pressure to afford 6.38 g of a light brown solid. The material was purified by column chromatography on silica gel (eluting with 98:2 methanol:dichloromethane) to afford 3.7 g of material.

Part C

The material from Part B and ammonium acetate (28.1 g, 365 mmol) were placed in a sealed glass container and heated to 150° C. for 48 hours. The reaction mixture was cooled and dissolved in ethanol (100 mL). Hydrochloric acid (45 mL, 12 M) was added to the reaction mixture and stirred at 90° C. and stirred overnight. The mixture was cooled to ambient temperature and filtered. The filtrate was concentrated under reduced pressure to afford 8.8 g of an orange solid. The solid was washed with acetone and the filtrate was concentrated under reduced pressure to afford 3.32 of 3,4-dimethyl-6,7,8,9-tetrahydropyrido[3',4':4,5]imidazo[1,2-a]pyrazin-1-amine dihydrochloride as a yellow solid.

Part D

A reagent (0.11 mmol) from the table below was added to a test tube containing 3,4-dimethyl-6,7,8,9-tetrahydropyrido[3',4':4,5]imidazo[1,2-a]pyrazin-1-amine dihydrochloride (29 mg, 0.10 mmol) and N,N-diisopropylethylamine (0.058 mL, 0.33 mmol) in DMF (1 mL). The test tubes were capped and shaken overnight at ambient temperature. The reaction mixture was then purified using a Waters OASIS Sample Extractions Cartridge MCX followed by prep HPLC according to the methods described in Examples 370-385. The table below shows the reagent added to each test tube, the structure of the resulting compound, and the observed accurate mass for the isolated product.

Example 611-644
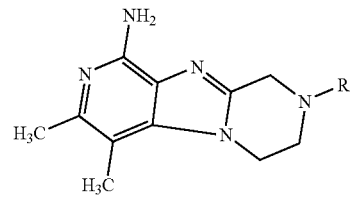
| Example | Reagent | R | Measured Mass (M + H) |
|---|---|---|---|
| 611 | None | H | 218.1400 |
| 612 | Methyl chloroformate | —C(O)OCH₃ | 276.1437 |
| 613 | Cyclopropanecarbonyl chloride | —C(O)-cyclopropyl | 286.1640 |
| 614 | Ethyl chloroformate | —C(O)OCH₂CH₃ | 290.1594 |
| 615 | Cyclobutanecarbonyl chloride | —C(O)-cyclobutyl | 300.1812 |
| 616 | 3-Furoyl chloride | —C(O)-(3-furyl) | 312.1445 |
| 617 | Benzoyl chloride | —C(O)-phenyl | 322.1657 |
| 618 | Cyclohexanecarbonyl chloride | —C(O)-cyclohexyl | 328.2118 |

-continued
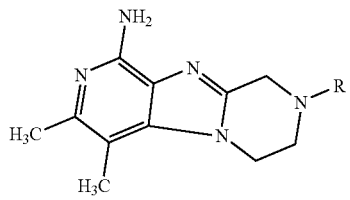
| Example | Reagent | R | Measured Mass (M + H) |
|---|---|---|---|
| 619 | Hydrocinnamoyl chloride | | 350.1960 |
| 620 | 3-Chlorobenzoyl chloride | | 356.1270 |
| 621 | Dimethylsulfamoyl chloride | | 325.1447 |
| 622 | 1-Butanesulfonyl chloride | | 338.1628 |
| 623 | Benzenesulfonyl chloride | | 358.1319 |
| 624 | 2-Thiophenesulfonyl chloride | | 364.0906 |
| 625 | 3-Methylbenzenesulfonyl chloride | | 372.1490 |
| 626 | alpha-Toluenesulfonyl chloride | | 372.1510 |

-continued

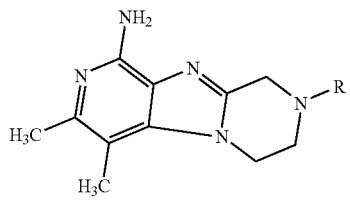

| Example | Reagent | R | Measured Mass (M + H) |
|---|---|---|---|
| 627 | 3-Cyanobenzenesulfonyl chloride | (3-cyanophenylsulfonyl) | 383.1274 |
| 628 | beta-Styrenesulfonyl chloride | (styrylsulfonyl) | 384.1471 |
| 629 | 3-Chlorobenzenesulfonyl chloride | (3-chlorophenylsulfonyl) | 392.0962 |
| 630 | 2-Naphthalenesulfonyl chloride | (2-naphthylsulfonyl) | 408.1496 |
| 631 | 8-Quinolinesulfonyl chloride | (8-quinolinylsulfonyl) | 409.1413 |
| 632 | 3-(Trifluoromethyl)benzenesulfonyl chloride | (3-trifluoromethylphenylsulfonyl) | 426.1242 |
| 633 | Methyl isothiocyanate | (N-methylthiocarbamoyl) | 291.1377 |
| 634 | Ethyl isothiocyanate | (N-ethylthiocarbamoyl) | 305.1537 |

-continued
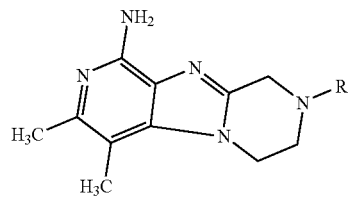
| Example | Reagent | R | Measured Mass (M + H) |
|---|---|---|---|
| 635 | Cyclopropyl isothiocyanate | HN-cyclopropyl, C(=S)- | 317.1536 |
| 636 | n-Propyl isothiocyanate | HN-CH2CH2CH3, C(=S)- | 319.1671 |
| 637 | N,N-Dimethylcarbamoyl chloride | (CH3)2N-C(=O)- | 289.1757 |
| 638 | Phenyl isocyanate | HN-Ph, C(=O)- | 337.1766 |
| 639 | Dimethylthiocarbamoyl chloride | (CH3)2N-C(=S)- | 305.1553 |
| 640 | Cyclohexyl isocyanate | HN-cyclohexyl, C(=O)- | 343.2225 |
| 641 | Benzyl isocyanate | HN-CH2Ph, C(=O)- | 351.1924 |

-continued

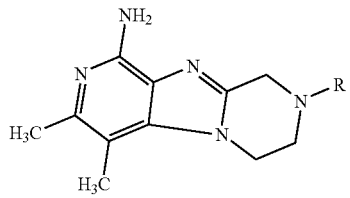

| Example | Reagent | R | Measured Mass (M + H) |
|---|---|---|---|
| 642 | Phenyl isothiocyanate | *N-phenyl thioamide group* | 353.1539 |
| 643 | 3-Pyridyl isothiocyanate | *N-(3-pyridyl) thioamide group* | 354.1503 |
| 644 | Ethyl 3-isocyanatopropionate | *ethyl N-propanoate amide group* | 361.1996 |

Example 645

9-[(Trifluoromethyl)sulfonyl]-9,10,11,12-tetrahydro-8H-[1,4]diazepino[1',2':1,2]imidazo[4,5-c]quinolin-6-amine

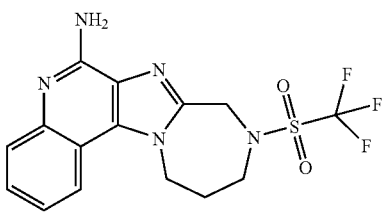

The methods described in Example 8 can be used to prepare 9-[(trifluoromethyl)sulfonyl]-9,10,11,12-tetrahydro-8H-[1,4]diazepino[1',2':1,2]imidazo[4,5-c]quinolin-6-amine from tert-butyl 11,12-dihydro-8H-[1,4]diazepino[1',2':1,2]imidazo[4,5-c]quinoline-9(10H)-carboxylate using trifluoromethanesulfonyl chloride in lieu of methanesulfonyl chloride in Part C.

Example 646

9-[(Trifluoromethyl)sulfonyl]-8,9,10,11-tetrahydropyrazino[1',2':1,2]imidazo[4,5-c]quinolin-6-amine

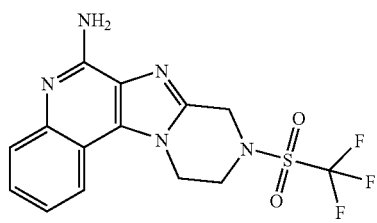

A modification of the methods described in Example 5 can be used to prepare 9-[(trifluoromethyl)sulfonyl]-8,9,10,11-tetrahydropyrazino[1',2':1,2]imidazo[4,5-c]quinolin-6-amine from tert-butyl 6-amino-10,11-dihydropyrazino[1',2':1,2]imidazo[4,5-c]quinoline-9(8H)-carboxylate using trifluoromethanesulfonyl chloride in lieu of methanesulfonyl chloride in Part B. Normal phase prep HPLC may be used in Part B to purify the product.

Example 647

3-Fluoro-9-(methylsulfonyl)-9,10,11,12-tetrahydro-8H-[1,4]diazepino[1',2':1,2]imidazo[4,5-c]quinolin-6-amine

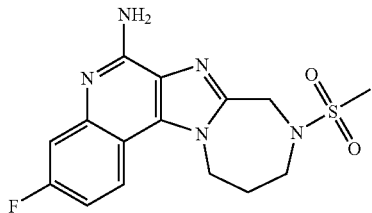

The methods described in Parts A through D of Example 368 and Parts A through G of Example 369 can be used to prepare 3-fluoro-9-(methylsulfonyl)-9,10,11,12-tetrahydro-8H-[1,4]diazepino[1',2':1,2]imidazo[4,5-c]quinolin-6-amine using 3-fluoroaniline in lieu of 3-benzyloxyaniline in Part A of Example 368.

Example 648

3-Fluoro-9-(methylsulfonyl)-8,9,10,11-tetrahydropyrazino[1',2':1,2]imidazo[4,5-c]quinolin-6-amine

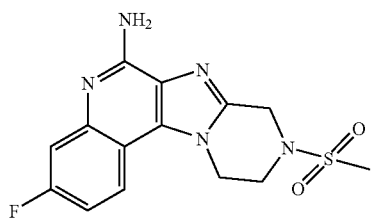

The methods described in Parts A through K of Example 368 can be used to prepare 3-fluoro-9-(methylsulfonyl)-8,9,10,11-tetrahydropyrazino[1',2':1,2]imidazo[4,5-c]quinolin-6-amine using 3-fluoroaniline in lieu of 3-benzyloxyaniline in Part A of Example 368.

Example 649

11,11-Difluoro-9-(methylsulfonyl)-9,10,11,12-tetrahydro-8H-[1,4]diazepino[1',2':1,2]imidazo[4,5-c]quinolin-6-amine

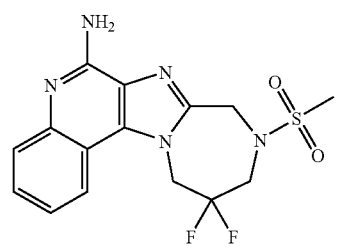

Part A

The method described in Part B of Example 364 can be used to prepare tert-butyl 3-amino-2,2-difluoropropylcarbamate from 2,2-difluropropane-1,3-diamine, which is available from the literature procedure: Nanjappan, P. et al., *Tetrahedron* 50(29), pp. 8617-8632, (1994).

Part B

The methods described in Parts A through D of Example 6 can be used to prepare tert-butyl 11,11-difluoro-11,12-dihydro-8H-[1,4]diazepino[1',2':1,2]imidazo[4,5-c]quinoline-9(10H)-carboxylate, using tert-butyl 3-amino-2,2-difluoropropylcarbamate in lieu of tert-butyl 3-aminopropylcarbamate in Part A.

Part C

The methods described in Example 364 can be used to prepare 11,11-difluoro-9-(methylsulfonyl)-9,10,11,12-tetrahydro-8H-[1,4]diazepino[1',2':1,2]imidazo[4,5-c]quinolin-6-amine using tert-butyl 11,11-difluoro-11,12-dihydro-8H-[1,4]diazepino[1',2':1,2]imidazo[4,5-c]quinoline-9(10H)-carboxylate in lieu of tert-butyl 11,12-dihydro-8H-[1,4]diazepino[1',2':1,2]imidazo[4,5-c]quinoline-9(10H)-carboxylate in Part A.

Compounds of the invention were found to induce or inhibit cytokine biosynthesis when tested using the methods described below.

Cytokine Induction in Human Cells

Compounds of the invention have been found to modulate cytokine biosynthesis by inducing the production of interferon α and/or tumor necrosis factor α when tested using the method described below. Particular examples include, but are not limited to, the compounds of Examples 1-5, 7-10, 12-14, 16, 19, 20, 22, 24-26, 28, 34, 37, 39, 41, 43, 44, 46, 74, 77-79, 81-84, 87, 92, 93, 97-100, 103, 106, 109, 112, 114, 115, 117, 121, 123, 125, 127-133, 135, 136, 138, 140, 147, 153, 157, 159, 160, 189-191, 193, 195-198, 200, 202-205, 208, 216, 217, 223, 230, 231, 239, 264, 266, 282, 283, 285-289, 296, 297, 302, 308, 309, 313, 345, 362-369, 386, 388, 389, 391-394, 396, 399, 404, 412, 413, 439, 440, 470, 485, 488-491, 493, 497, 498, 500, 567, 612, 625, 626, 631, 635-639, 641, and 644.

An in vitro human blood cell system is used to assess cytokine induction. Activity is based on the measurement of interferon (α) and tumor necrosis factor (α) (IFN and TNF, respectively) secreted into culture media as described by Testerman et al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4 \times 10^6$ cells/mL in RPMI complete. The PBMC suspension is added to 48 well flat bottom sterile tissue culture plates (Costar, Cambridge, Mass.

or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (30-0.014 µM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

TNF-α Inhibition in Mouse Cells

Certain compounds of the invention may modulate cytokine biosynthesis by inhibiting production of tumor necrosis factor α (TNF-α) when tested using the method described below. Particular examples, include but are not limited to, the compounds of Examples 74-76, 79, 81, 92, 94, 95, 103, 104, 108-110, 200, 210, 212-218, 220-226, 230, 232-234, 236-240, 242-244, 283, 285-290, 293, 299, 301-305, 308, 310-312, 314, 315, 317, 321, 323, 324, and 326-328.

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4\times10^5$ cells/mL in RPMI with 10% FBS. Cell suspension (250 µL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimuriumn*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 µL, $EC_{70}$ concentration~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be under-

What we claim is:

1. A compound of the Formula II:

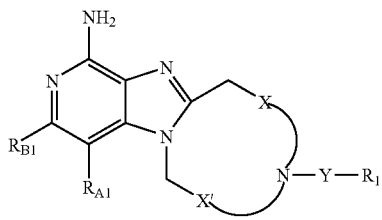

wherein:
$R_{A1}$ and $R_{B1}$ are
taken together to form a fused aryl ring, wherein the aryl ring is unsubstituted or substituted by one or more R groups, or substituted by one $R_3$ group, or substituted by one $R_3$ group and one R group;

X is a bond;
X' is —(CH$_2$)$_2$—
Y is selected from the group consisting of:
  a bond,
  —S(O)$_2$—,
  —S(O)$_2$—N(R$_8$)—,
  —C(R$_6$)—,
  —C(R$_6$)—O—, —C(R$_6$)—N(R$_8$)—,
  —C(R$_6$)—N(R$_8$)—C(R$_6$)—, and
  —C(R$_6$)—N(R$_8$)—S(O)$_2$—;

$R_1$ is selected from the group consisting of: hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of aryl, methylenedioxy; further with the proviso that when $R_{A1}$ and $R_{B1}$, together form a fused benzene ring that is unsubstituted or substituted by C$_{1-4}$ alkyl, C$_{1-4}$ alkoxy, or halogen, and Y is a bond, $R_1$ is not hydrogen or C$_{1-4}$ alkyl;

R is selected from the group consisting of:
  halogen,
  hydroxy,
  alkyl,
  alkenyl,
  haloalkyl,
  alkoxy,
  alkylthio, and
  —N(R$_9$)$_2$;

$R_3$ is selected from the group consisting of:
  —Z—R$_4$,
  —Z—X"—R$_4$,
  —Z—X"—Y'—R$_4$,
  —Z—X"—Y'—X"—Y'—R$_4$, and
  —Z—X"—R$_5$;

X" is selected from the group consisting of alkylene, alkenylene, alkynylene, arylene, heteroarylene, and heterocyclylene wherein the alkylene, alkenylene, and alkenylene groups can be optionally interrupted or terminated by arylene, heteroarylene or heterocyclylene and optionally interrupted by one or more —O— groups;

Y' is selected from the group consisting of:
  —S(O)$_{0-2}$—,
  —S(O)$_2$—N(R$_8$)—,
  —C(R$_6$)—,
  —C(R$_6$)—O—,
  —O—C(R$_6$)—,
  —O—C(O)—O—,
  —N(R$_8$)-Q-,
  —C(R$_6$)—N(R$_8$)—,
  —O—C(R$_6$)—N(R$_8$)—,
  —C(R$_6$)—N(OR$_9$)—,

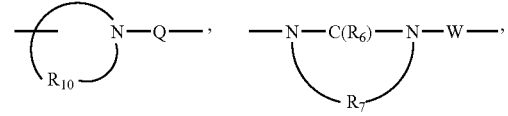

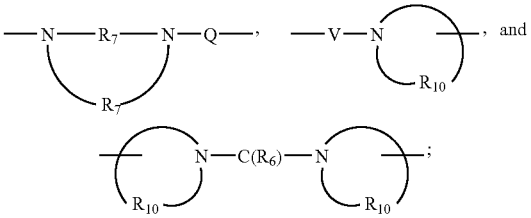

Z is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents selected from the group consisting of alkyl, alkoxy, hydroxyalkyl, haloalkyl, haloalkoxy, halogen, nitro, hydroxy, mercapto, cyan, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

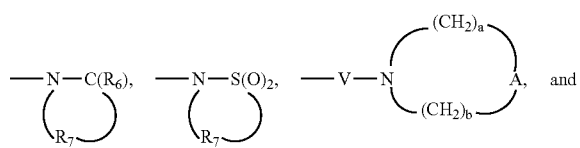

-continued

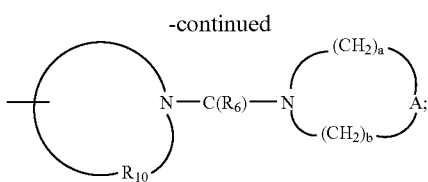

$R_6$ is selected from the group consisting of =O and =S;
$R_7$ is $C_{2-7}$ alkyene;
$R_8$ is selected from the group consisting of hydrogen, $C_{1-10}$ alkyl, $C_{2-10}$ alkenyl, $C_{1-10}$ alkoxy-$C_1$ alkylenyl, and aryl-$C_{1-10}$ alkylenyl;
$R_9$ is selected from the group consisting of hydrogen and alkyl;
$R_{10}$ is $C_{3-8}$ alkylene;
$R_{11}$ is selected from the group consisting of $C_{1-6}$ alkyl and —Si($C_{1-6}$ alkyl)$_3$;
A is selected from the group consisting of —CH$_2$—, —O—, —C(O)—, —S(O)$_{0-2}$—, and N(R$_4$)—,
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

2. A compound or salt of claim 1 wherein Y is selected from the group consisting of —C(O)—, —S(O)$_2$—, or —C(O)—NH—, and $R_1$ is $C_{1-3}$ alkyl.

3. A compound or salt of claim 2 wherein Y is —S(O)$_2$—, and $R_1$ is methyl.

4. A pharmaceutical composition comprising a therapeutically effective amount of a compound or salt of claim 1 in combination with a pharmaceutically acceptable carrier.

5. A compound of the Formula IV:

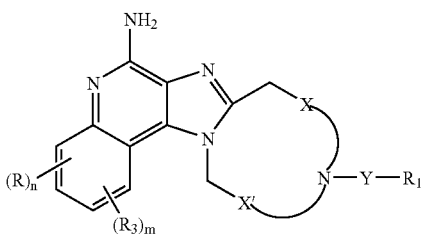

IV wherein:
X is a bond;
X' is —(CH$_2$)$_2$—;
Y is selected from the group consisting of:
  a bond,
  —S(O)$_2$—,
  —S(O)$_2$—N(R$_8$)—,
  —C(R$_6$)—O—,
  —C(R$_6$)—N(R$_8$)—,
  —C(R$_6$)—N(R$_8$)—C(R$_6$)—, and
  —C(R$_6$)—N(R$_8$)—S(O)$_2$—;
$R_1$ is selected from the group consisting of hydrogen, alkyl, alkenyl, alkenyl, aryl, arylalkylenyl, aryloxyalkylenyl, alkylarylenyl, heteroaryl, heteroarylalkylenyl, heteroaryloxyalkylenyl, alkylheteroaryienyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyano, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkenyl, and heterocyclyl, oxo, and in the case of aryl, methylenedioxy;
R is selected from the group consisting of:
  halogen,
  hydroxy,
  alkyl,
  alkenyl,
  haloalkyl,
  alkoxy,
  alkylthio, and
  N(R$_9$)$_2$;
$R_3$ is selected from the group consisting of:
  —Z—R$_4$,
  —Z—X"—R$_4$,
  —Z—X"—Y'—R$_4$,
  —Z—X"—Y'—X"—Y'—R$_4$, and
  —Z—X"—R$_5$;
m is 0 or 1; with the proviso that when m is 1, then n is 0 or 1;
n is an integer from 0 to 4;
X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y' is selected from the group consisting of:
  —S(O)$_{0-2}$—,
  —S(O)$_2$—N(R$_8$)—,
  —C(R$_6$)—,
  —C(R$_6$)—O—,
  —O—C(R$_6$)—,
  —O—C(O)—O—,
  —N(R$_8$)-Q-,
  —C(R$_6$)—N(R$_8$)—,
  —O—C(R$_6$)—N(R$_8$)—,
  —C(R$_6$)—N(OR$_9$)—,

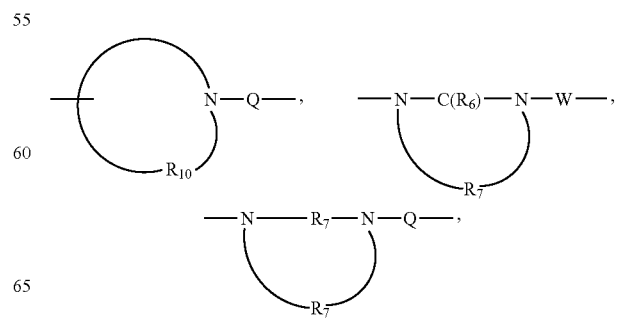

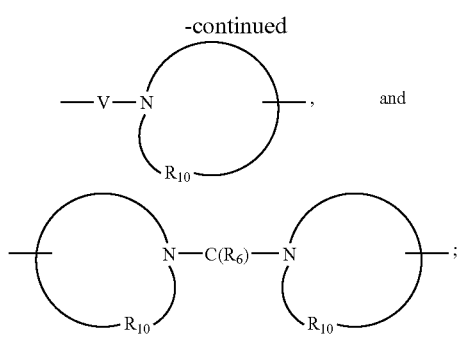

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents selected from the group consisting of alkyl, alkoxy, hydroxyalkyl, haloalkyl, haloalkoxy, halogen, nitro, hydroxy, mercapto, cyan, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

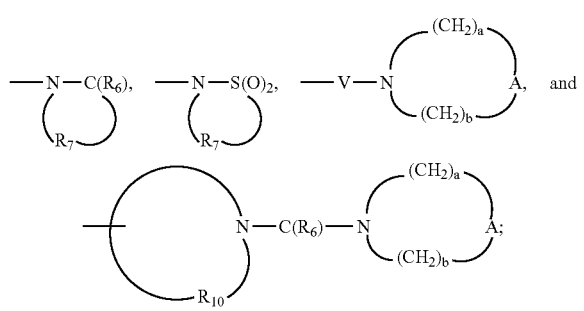

R$_6$ is selected from the group consisting of =O and =S;

R$_7$ is C$_{2-7}$ alkylene;

R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

R$_9$ is selected from the group consisting of hydrogen and alkyl;

R$_{10}$ is C$_{3-8}$ alkylene;

R$_{11}$ is selected from the group consisting of C$_{1-6}$ alkyl and —Si(C$_{1-6}$ alkyl)$_3$;

A is selected from the group consisting of —CH$_2$—, —O—, —C(O)—, —S(O)$_{0-2}$—, and N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(O)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that R, is not hydrogen or C$_{1-4}$ alkyl when Y is a bond, and:
n and m are both 0, or
m is 0, n is 1, and R is selected from the group consisting of C$_{1-4}$ alkyl, C$_{1-4}$ alkoxy, and halogen;

or a pharmaceutically acceptable salt thereof.

6. A compound of the Formula IV:

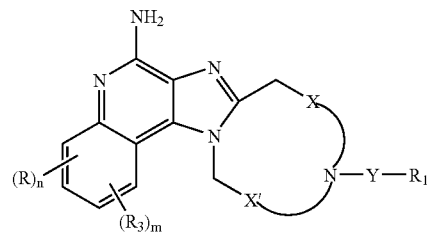

wherein:
X is a bond;
X' is —(CH$_2$)$_2$—;
Y is selected from the group consisting of:
a bond,
—S(O)$_2$—,
—S(O)$_2$—N(R$_8$)—,
—C(R$_6$)—,
—C(R$_6$)—N(R$_8$)—,
—C(R$_6$)—N(R$_8$)—C(R$_6$)—, and
—C(R$_6$)—N(R$_8$)—S(O)$_2$—;

R$_1$ is selected from the group consisting of: hydrogen, alkyl, alkenyl, alkenyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkenyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, alkylthio, alkanoyl, alkanoyloxy, alkoxycarbonyl, hydroxyalkyl, haloalkyl, haloalkoxy, halogen, nitro, hydroxy, mercapto, cyan, aryl, aryloxy, arylthio, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkenyl, and heterocyclyl, oxo, and in the case of aryl, methylenedioxy; further with the proviso that when Y is a bond, R$_1$ is not hydrogen or C$_{1-4}$ alkyl;

R is selected from the group consisting of:
halogen,
hydroxy,
alkyl,
alkenyl,
haloalkyl,
alkoxy,
alkylthio, and
—N(R$_9$)$_2$;

R$_3$ is selected from the group consisting of:
—Z—R$_4$,
—Z—X'—R$_4$,
—Z—X"—Y'—R$_4$, —Z—X"—Y'—X"—Y'—R$_4$, and
—Z—X"—R$_5$;

m is 0 or 1; with the proviso that when m is 1, then n is 0 or 1;

n is an integer from 0 to 4;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

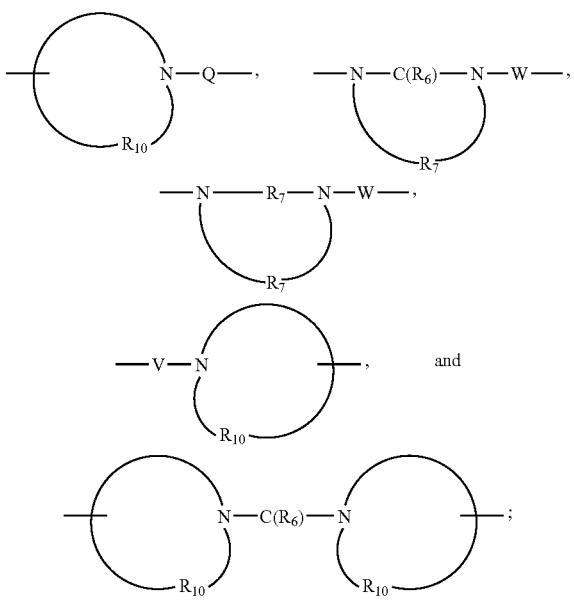

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyan, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

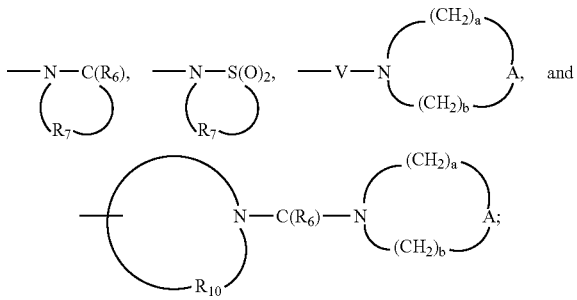

R$_6$ is selected from the group consisting of =O and =S;
R$_7$ is C$_{2-7}$ alkylene;
R$_8$ is selected from the group consisting of hydrogen, C$_{10}$ alkyl, C$_{2-10}$ alkynyl, C$_{1-10}$ alkoxy-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;
A is selected from the group consisting of —CH$_2$—, —O—, —C(O)—, —S(O)$_{0-2}$—, and N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);
V is selected from the group consisting of —C(R$_6$)—, —O—C(R$_6$)—, —N(R$_8$)—C(R$_6$)—, and —S(O)$_2$;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

7. A compound or salt of claim 5 wherein m is 0 and n is 0.

8. A compound or salt of claim 5 wherein the compound is 9-(methylsulfonyl)-9,10,11,12-tetrahydro-8H-[1,4]diazepino[1',2':1,2]imidazo[4,5-c]quinolin-6-amine or a pharmaceutically acceptable salt thereof.

9. A compound or salt of claim 5 wherein Y is selected from the group consisting of C(O)—, —S(O)$_2$—, —C(O)—NH—, and R$_1$ is C$_{1-3}$ alkyl.

10. A compound or salt of claim 9 wherein Y is —S(O)$_2$, and R$_1$ is methyl.

11. A pharmaceutical composition comprising a therapeutically effective amount of a compound or salt of claim 5 in combination with a pharmaceutically acceptable carrier.

12. A pharmaceutical composition comprising a therapeutically effective amount of a compound or salt of claim 8 in combination with a pharmaceutically acceptable carrier.

* * * * *

UNITED STATES PATENT AND TRADEMARK OFFICE
CERTIFICATE OF CORRECTION

PATENT NO. : 7,888,349 B2  
APPLICATION NO. : 10/596895  
DATED : February 15, 2011  
INVENTOR(S) : Tushar Ashok Kshirsagar Page 1 of 8

It is certified that error appears in the above-identified patent and that said Letters Patent is hereby corrected as shown below:

Column 4  
Line 46, delete "—($R_6$)—" and insert -- —C($R_6$)— --, therefor.  
Line 63, delete "heteroarylalkylenyl" and insert -- heteroarylalkylenyl, --, therefor.

Column 5  
Lines 6-7, delete "methylenedioxy," and insert -- methylenedioxy; --, therefor.  
Line 12, delete "group-consisting" and insert -- group consisting --, therefor.  
Line 37, delete "$R_{B1}$," and insert -- $R_{B1}$ --, therefor.  
Line 41, below "halogen," insert -- alkyl, --.

Column 6  
Lines 21-22, delete "methyleneoxy; fuirther" and insert -- methylenedioxy; further --, therefor.

Column 8  
Line 67, delete "thereof" and insert -- thereof. --, therefor.

Column 11  
Line 7, after "and" insert -- —N($R_4$)—; --.  
Line 11, delete "—C($R_8$)—" and insert -- —C($R_6$)— --, therefor.

Signed and Sealed this  
Eighth Day of November, 2011

David J. Kappos  
*Director of the United States Patent and Trademark Office*

Lines 26-38, delete " 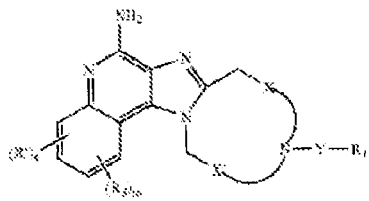 " and insert

-- 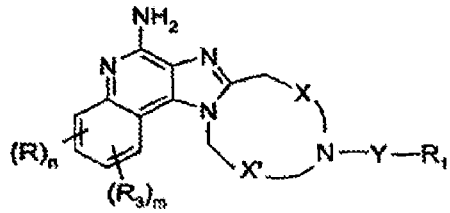
IV
--, therefor.

Column 19
Line 32, delete "substitutent." and insert -- substituent. --, therefor.
Lines 42-43, delete "—X'—Y'—X'—" and insert -- —X"—Y'—X"— --, therefor.

Column 20
Line 1, delete "I-VU" and insert -- I-VII --, therefor.
Line 11, delete "heteroatom:" and insert -- heteroatom --, therefor.

Column 21
Line 47, delete "—(O)—" and insert -- —C(O)— --, therefor.

Column 22
Line 62, delete "allylarylenyl," and insert -- alkylarylenyl, --, therefor.

Column 24
Lines 12-13, delete "irnmunomodulator" and insert -- immunomodulator --, therefor.

Column 26
Line 45, delete "R$_1$S(O)$_2$Cl" and insert -- R$_1$S(O)$_2$Cl, --, therefor.
Line 49, delete "R$_1$S(O)$_2$Cl" and insert -- R$_1$S(O)$_2$Cl, --, therefor.

Column 30
Line 36, delete "XXII," and insert -- XXIII, --, therefor.

Column 32
Line 26, delete "XX." and insert -- XXXI. --, therefor.
Line 27, delete "X," and insert -- XXXI, --, therefor.

CERTIFICATE OF CORRECTION (continued)
U.S. Pat. No. 7,888,349 B2

Column 33
Line 22, delete "X'," and insert -- X", --, therefor.
Line 24, delete "XXXIII" and insert -- XXXII --, therefor.
Lines 34-35, delete "X Iundergoes" and insert -- XXXIII undergoes --, therefor.
Line 62, delete "XVIII." and insert -- XXXVII. --, therefor.

Column 34
Line 40, delete "XXVII" and insert -- XXXVII --, therefor.

Column 35
Line 27, delete "X'—" and insert -- X"— --, therefor.

Column 36
Line 31, delete "tetrahydrofliran" and insert -- tetrahydrofuran --, therefor.

Columns 37-38
Line 3, delete

" and insert

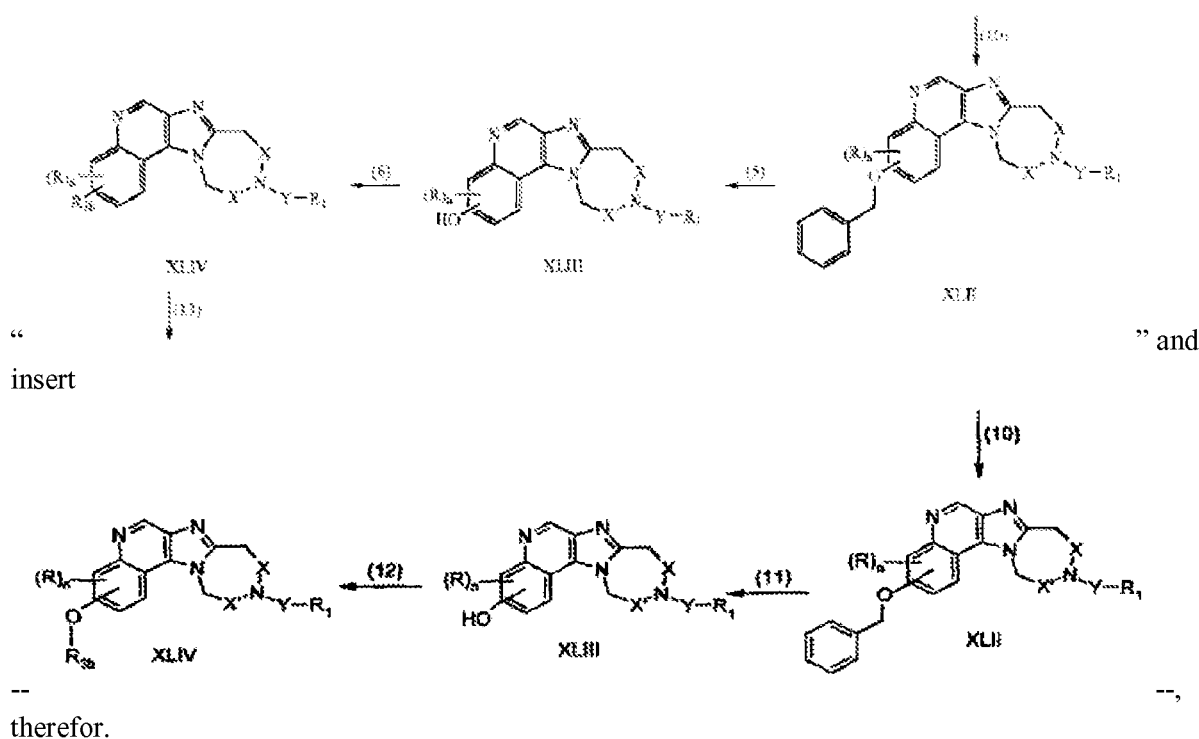

--, therefor.

Line 4, delete " 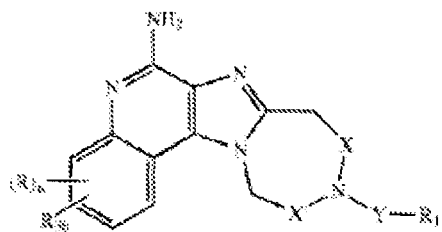 " and insert
-- 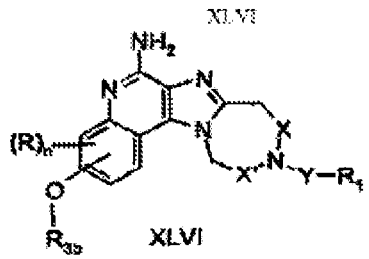 --, therefor.

Column 37
Line 60, delete "XLVI" and insert -- XLVIII --, therefor.

Column 42
Line 60, delete "LVII" and insert -- LVIII --, therefor.

Column 44
Line 61, delete "hetereogeneous" and insert -- heterogeneous --, therefor.

Column 45
Lines 27-28, delete "[1,5]naphthyridin" and insert -- quinolin --, therefor.
Line 67, delete "substitued" and insert -- substituted --, therefor.

Column 47
Lines 55-56, delete "hepadnavirns" and insert -- hepadnavirus --, therefor.

Column 48
Line 4, delete "carnii" and insert -- carinii --, therefor.
Line 11, delete "myelogeous" and insert -- myelogenous --, therefor.
Line 19, delete "thrombocythaemia," and insert -- thrombocythemia, --, therefor.
Line 38, delete "hemophilus" and insert -- haemophilus --, therefor.

Column 50
Line 53, delete "carbatnate" and insert -- carbamate --, therefor.
Line 61, delete "mnmol)" and insert -- mmol) --, therefor.
Line 64, delete "and," and insert -- and --, therefor.

CERTIFICATE OF CORRECTION (continued)
U.S. Pat. No. 7,888,349 B2

Column 54
Line 48, delete "iridazo" and insert -- imidazo --, therefor.
Line 66, delete "N." and insert -- N, --, therefor.

Column 57
Line 66, delete "amninopropyl)" and insert -- aminopropyl) --, therefor.

Column 58
Line 26, delete "mnL)." and insert -- mL). --, therefor.

Column 93
Line 32, delete "(32.2" and insert -- (32.3 --, therefor.

Columns 95-96
Line 8, delete "imidazolecaboxaldehyde" and insert -- imidazolecarboxaldehyde --, therefor.

Column 113
Line 40, delete "NN" and insert -- N,N --, therefor.

Columns 127-128 (Example 233)
Line 6, after "Butylbenzoyl" insert -- chloride --.

Columns 129-130 (Example 240)
Line 8, delete "Dichlorobenozyl" and insert -- Dichlorobenzoyl --, therefor.

Columns 133-134 (Example 253)
Line 7, delete "Thiosulfonyl" and insert -- Thiophenesulfonyl --, therefor.

Column 153
Line 56, after "mol" insert -- in --.

Column 154
Line 58, delete "amnino" and insert -- amino --, therefor.

Column 155
Line 8, delete "(1 L)" and insert -- (1 mL) --, therefor.

Column 166
Line 34, delete "CEL1TE" and insert -- CELITE --, therefor.

Column 167
Line 27, delete "dichlormethane" and insert -- dichloromethane --, therefor.
Line 43, delete "dichlormethane" and insert -- dichloromethane --, therefor.
Lines 50-51, delete "naphthyridin" and insert -- naphthyridine --, therefor.

Column 169
Line 57, delete "-etrahydro" and insert -- tetrahydro --, therefor.

Column 171
Line 44, delete "quinohne" and insert -- quinoline --, therefor.

Column 173
Line 3, delete "1H)" and insert -- 1H), --, therefor.

Column 174
Line 64, delete "p-toluenesulfnyl" and insert -- p-toluenesulfonyl --, therefor.

Column 178
Line 5, delete "n-pronanol" and insert -- n-propanol --, therefor.
Line 45, delete "Sarnple" and insert -- Sample --, therefor.
Line 53, delete "HHLC" and insert -- HPLC --, therefor.

Columns 181-182 (Example 381)
Line 12, delete "pyrzole" and insert -- pyrazole --, therefor.

Columns 193-194 (Example 422)
Line 13, delete "Dimehylthiocarbamoyl" and insert -- Dimethylthiocarbamoyl --, therefor.

Column 210
Line 11, delete "Example" and insert -- Examples --, therefor.

Columns 209-210 (Example 471)
Line 17, delete "Isovaleradehyde" and insert -- Isovaleraldehyde --, therefor.

Column 215
Line 26, delete "[1∝," and insert -- [1', --, therefor.

Columns 215-216

Line 41, delete " 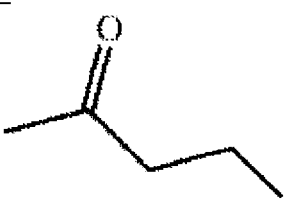 " and insert

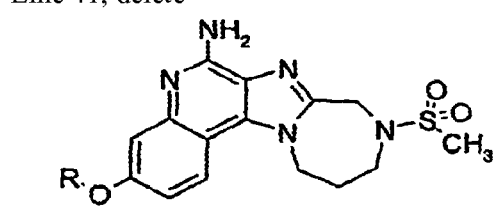

-- --, therefor.

Column 218
Line 66, delete "(10 B)" and insert -- (10H) --, therefor.

Column 219
Line 9, delete "ml)." and insert -- mL). --, therefor.

Columns 233-234 (Example 542)

Line 9, delete " 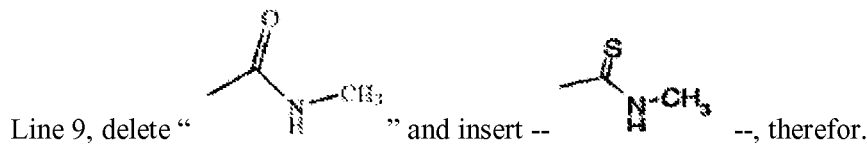 " and insert -- --, therefor.

Columns 235-236 (Example 549)

Line 9, delete " 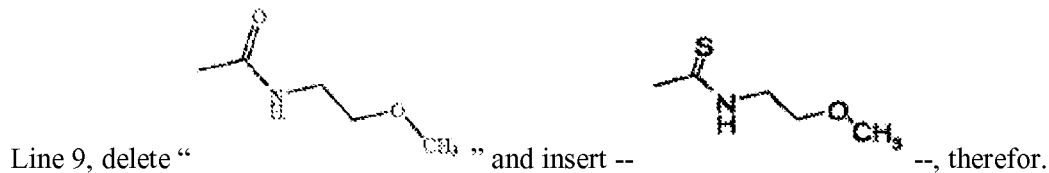 " and insert -- --, therefor.

Column 266
Line 5, delete "difluropropane" and insert -- difluoropropane --, therefor.

Column 268
Line 9, delete "Lipopolysaccaride" and insert -- Lipopolysaccharide --, therefor.
Line 44, delete "Lipopolysaccaride" and insert -- Lipopolysaccharide --, therefor.
Line 44, delete "typhimuriumn," and insert -- typhimurium, --, therefor.

Column 269
Line 27, in Claim 1, delete "—(CH$_2$)$_2$—" and insert -- —(CH$_2$)$_2$—; --, therefor.
Lines 34-35, in Claim 1, delete "—C(R$_6$)—O—, —C(R$_6$)—N(R$_8$)—," and insert
-- —C(R$_6$)—O—, —C(R$_6$)—N(R$_8$)—, --, therefor.

Column 271
Line 11, in Claim 1, delete "alkyene;" and insert -- alkylene; --, therefor.
Line 13, in Claim 1, delete "alkoxy-C$_1$" and insert -- alkoxy-C$_{1-10}$ --, therefor.
Line 67, in Claim 5, delete "alkenyl, alkenyl," and insert -- alkenyl, alkynyl, --,
therefor.

Column 272
Line 2, in Claim 5, delete "alkylheteroaryienyl," and insert -- alkylheteroarylenyl, --, therefor.
Lines 14-15, in Claim 5, delete "alkenyl, alkenyl," and insert -- alkenyl, alkynyl, --, therefor.

Column 274
Line 37, in Claim 6, delete "alkenyl, alkenyl," and insert -- alkenyl, alkynyl, --, therefor.
Line 40, in Claim 6, delete "alkenyl, alkenyl," and insert -- alkenyl, alkynyl, --, therefor.
Lines 51-52, in Claim 6, delete "alkenyl, alkenyl," and insert -- alkenyl, alkynyl, --, therefor.

Column 276
Line 25, in Claim 6, delete "$C_{10}$" and insert -- $C_{1-10}$ --, therefor.
Line 38, in Claim 6, delete "—$S(O)_2$;" and insert -- —$S(O)_2$—; --, therefor.
Line 50, in Claim 9, delete "C(O)—," and insert -- —C(O)—, --, therefor.
Line 52, in Claim 10, delete "—$S(O)_2$," and insert -- —$S(O)_2$—, --, therefor.